United States Patent [19]

Moschel et al.

[11] Patent Number: 5,691,307

[45] Date of Patent: Nov. 25, 1997

[54] $O^6$-SUBSTITUTED GUANINE COMPOSITIONS AND METHODS FOR DEPLETING $O^6$-ALKYLGUANINE-DNA ALKYLTRANSFERASE

[75] Inventors: Robert C. Moschel, Frederick, Md.; M. Eileen Dolan, Oak Park, Ill.; Anthony E. Pegg, Hershey, Pa.; Mark G. McDougall, Cleveland, Ohio; Mi-Young Chae, Frederick, Md.

[73] Assignees: The United States of America as represented by the Department of Health and Human Services, Washington, D.C.; The Penn State Research Foundation, University Park, Pa.; Arch Development Corporation, Chicago, Ill.

[21] Appl. No.: 255,190

[22] Filed: Jun. 7, 1994

Related U.S. Application Data

[63] Continuation-in-part of Ser. No. 875,438, Apr. 29, 1992, abandoned, Ser. No. 616,913, Nov. 21, 1990, Pat. No. 5,352,669, and Ser. No. 805,634, Dec. 12, 1991, Pat. No. 5,358,952, which is a division of Ser. No. 492,468, Mar. 13, 1990, Pat. No. 5,091,430.

[51] Int. Cl.$^6$ ............ A61K 31/54; A61K 31/535; A61K 31/52; A61K 31/70; C07D 403/02; C07D 403/12; C07D 473/18; C07D 413/18

[52] U.S. Cl. .................. 514/12; 514/13; 514/14; 514/15; 514/16; 514/18; 514/19; 514/20; 514/262; 514/26; 514/27; 514/44; 514/45; 514/48; 514/950; 514/81; 514/245; 514/183; 514/589; 514/256; 514/771; 514/417; 514/414; 544/276; 536/5; 536/17.3; 536/24.1; 530/324; 530/325; 530/326; 530/327; 530/328; 530/329; 530/330; 530/278

[58] Field of Search ............... 514/262, 12, 13, 514/14, 15, 16, 17, 18, 19, 20, 26, 27, 44, 45, 48, 950, 81, 245, 183, 589, 256, 771, 417, 414; 544/276; 536/5, 17.3, 24.1; 530/324, 325, 326, 327, 328, 329, 330, 27.8

[56] References Cited

U.S. PATENT DOCUMENTS

| | | | |
|---|---|---|---|
| 4,199,574 | 4/1980 | Schaeffer | 424/200 |
| 5,091,430 | 2/1992 | Moschel et al. | 514/262 |
| 5,352,669 | 10/1994 | Moschel et al. | 514/45 |
| 5,358,952 | 10/1994 | Moschel et al. | 514/262 |

FOREIGN PATENT DOCUMENTS

| | | |
|---|---|---|
| 184473 | 8/1986 | European Pat. Off. |
| 335355 | 10/1989 | European Pat. Off. |

OTHER PUBLICATIONS

Kjellberg et al., Tet. Lett., 27(7), 877–880, 1986.
Stein et al., Biochem. Pharmacol., 36(8), 1237–1244, 1987.
Ramzaeva et al., Synth. Commun., 19(18), 3121–3128, 1989.
Moschel et al., J. Org. Chem., 51, 4180–4185 (1986).
Beaman et al., in Zorbach and Tipson, Synthetic Procedures in Nucleic Acid Chemistry, vol. 1, 41–43 (John Wiley & Sons, New York, NY, 1968).
Boon et al., J. Chem. Soc., 96–102 (1951).
Brix et al., J. Cancer Res. Clin. Oncol., 116, 538–549 (1990).
Carbon, J. Org. Chem., 25, 1731–1734 (1960).
Chae et al., J. Med. Chem., 37, 342–347 (1994).
Daves et al., J. Am. Chem. Soc., 82, 2633–2640 (1960).
Delia et al., Heterocycles, 20, 1805–1809 (1983).
Dolan et al., Cancer Chemother. Pharmacol., 32, 221–225 (1993).
Dolan et al., Biochem. Pharmacol., 46, 285–290 (1993).
Dolan et al., Cancer Res., 51, 3367–3372 (1991).
Dolan et al., Cancer Communications, 2, 371–377 (1990).
Dorr et al., in Cancer Chemotherapy Handbook, 715–742 (Elsevier Science Publishing, New York, NY, 1980).
Felker et al., Cancer Chemother. Pharmacol, 32, 471–476 (1993).
Fischer et al., in The Cancer Chemotherapy Handbook, 3rd ed., pp. 4–9, 60–61, 164–165, 171 (Year Book Medical Publishers, Inc., Chicago, IL, 1989).
Fondy et al., J. Med. Chem., 21, 1222–1225 (1978).
Friedman et al., J. Natl. Cancer Inst., 84, 1926–1931 (1992).
Gerson et al., Biochem. Pharmacol., 45, 483–491 (1993).
Holmes et al., J. Org. Chem., 43, 516–518 (1978).
House, in Modern Synthetic Reactions, pp. 536–541 and pp. 602–603 (W. A. Benjamin, 1972).
Jones et al., J. Am. Chem. Soc., 82, 3773–3779 (1960).
Kosary et al., Acta Pharm. Hungarica, 59, 241–247 (1989).
Leonard et al., J. Am. Chem. Soc., 96, 5894–5903 (1974).
March, in Advanced Organic Chemistry, 3rd ed., pp. 358–359, pp. 574–575, pp. 802–803, and pp. 982–985 (John Wiley & Sons, 1985).
Moschel et al., J. Med. Chem., 35, 4486–4491 (1992).
Murray, Chem. Rev., 89, 1187–1201 (1989).
O'Brien et al., J. Med. Chem., 9, 573–575 (1966).
Pansare et al., Organic Syntheses, 70, 1–9 (1992).
Pansare et al., Organic Syntheses, 70, 10–17 (1992).
Pauly et al., Biochemistry, 30, 11700–11706 (1991).
Pegg, Cancer Res., 50, 6119–6129 (1990).
Phillips et al., J. Org. Chem., 28, 1488–1490 (1963).
Shealy et al., J. Org. Chem., 27, 4518–4523 (1962).
Skinner, J. Org. Chem., 25, 149–151 (1960).
Wakabashi et al., Nippon Dojo–Hiryyogaku Zasshi, 41, 193–200 (1970).
Wallace, Aldrichimica Acta, 13, 3–11 (1980).
Wilson, Pigment Cell Research, 2, 297–303 (1989).
Winograd et al., In Vivo, 1, 1–14 (1987).

Primary Examiner—Matthew V. Grumbling
Attorney, Agent, or Firm—Leydig, Voit & Mayer, Ltd.

[57] ABSTRACT

Novel $O^6$-substituted guanine compounds and pharmaceutical compositions thereof are useful for effectively reducing $O^6$-alkylguanine-DNA alkyltransferase (AGT). The novel compounds are useful for treating tumors and when used with anti-neoplastic alkylating agents enhance the chemotherapeutic treatment of tumor cells in a host.

76 Claims, No Drawings

$O^6$-SUBSTITUTED GUANINE COMPOSITIONS AND METHODS FOR DEPLETING $O^6$-ALKYLGUANINE-DNA ALKYLTRANSFERASE

BACKGROUND OF THE INVENTION

The present application is a continuation-in-part application of U.S. application Ser. No. 07/875,438 filed Apr. 29, 1992, now abandoned U.S. application Ser. No. 07/616,913 filed Nov. 21, 1990, now U.S. Pat. No. 5,352,669, issued Oct. 4, 1994, and U.S. application Ser. No. 07/805,634, filed on Dec. 12, 1991, now U.S. Pat. No. 5,358,952 issued Oct. 25, 1994, which is a divisional of U.S. application Ser. No. 07/492,468 filed Mar. 13, 1990 now U.S. Pat. No. 5,091,430, all of these applications and patents being expressly incorporated by reference herein.

FIELD OF THE INVENTION

The present invention relates to $O^6$-substituted guanine derivatives which possess the ability to deplete $O^6$-alkylguanine-DNA alkyltransferase (AGT) activity in vitro and in vivo and to methods for the administration thereof to enhance the chemotherapeutic treatment of tumor cells in a host. More specifically the present invention relates to 9-substituted $O^6$-benzylguanine derivatives wherein the benzene ring of the benzyl group may be substituted at the ortho, meta, or para position and the 9-position of the purine may be substituted with a wide variety of groups of diverse chemical structure. The present invention also relates to $O^6$-allylguanine derivatives wherein the allyl substituent may be substituted at either the alpha, beta, or gamma carbon. In addition, the present invention relates to methods for administering compositions containing these compounds to a host in order to reduce AGT activity in the host and thereby increase the host's responsiveness to anti-neoplastic alkylating agents such as chloroethylating agents (e.g. chloroethylnitrosoureas or chloroethyltriazenes) or monofunctional alkylating agents such as Streptozotocin, Procarbazine, Dacarbazine and Temozolomide when these are simultaneously or subsequently administered to a host. This invention is applicable to all classes of anti-neoplastic alkylating agents whose mechanism of action involves modification of the $O^6$ position of DNA-guanine residues.

Among the chloroethylating agents, the most frequently used chemotherapeutic drugs in this series are 1-(2-chloroethyl)-3-cyclohexyl-1-nitrosourea (CCNU, lomustine), 1,3-bis(2-chloroethyl)-1-nitrosourea (BCNU, carmustine), 1-(2-chloroethyl)-3-(4-methylcyclohexyl)-1-nitrosourea (MeCCNU, semustine), and. 1-(2-chloroethyl)-3-(4-amino-2-methyl-5-pyrimidinyl) methyl-1-nitrosourea (ACNU). These agents have been used clinically against tumors of the central nervous system, multiple myeloma, melanoma lymphoma, gastrointestinal tumors, and other solid tumors (Colvin and Chabner, Alkylating Agents. In: *Cancer Chemotherapy: Principles and Practice* Edited by B. A. Chabner and J. M. Collins, Lippincott, Philadelphia, pp. 276–313 (1990); McCormick and McElhinney, *Eur. J. Cancer,* 26, 207–221 (1990)). Chloroethylating agents currently under development with fewer side effects are 1-(2-chloroethyl)-3-(2-hydroxyethyl)-1-nitrosourea (HECNU), 2-chloroethylmethylsulfonylmethanesulfonate (Clomesone), and 1-[N-(2-chloroethyl)-N-nitrosoureido] ethylphosphonic acid diethyl ester (Fotemustine) (Colvin and Chabner, Alkylating Agents. In: *Cancer Chemotherapy: Principles and Practice* Edited by B. A. Chabner and J. M. Collins, Lippincott, Philadelphia, pp. 276–313 (1990); McCormick and McElhinney, *Eur. J. Cancer,* 26, 207–221 (1990)). Methylating chemotherapeutic agents include Streptozotocin [2-deoxy-2-(3-methyl-3-nitrosoureido)-D-glucopyranose], Procarbazine {N-(1-methylethyl)-4-[(2-methylhydrazino) methyl] benzamide}, and Dacarbazine or DTIC [5-(3,3-dimethyl-1-triazenyl)-1H-imidazole-4-carboxamide], and Temozolomide {8-carbamoyl-3-methylimidazo[5,1-d]-1,2,3,5-tetrazin-4-(3H)-one}. Temozolomide is active against malignant melanomas, brain tumors and mycosis fungoides. Streptozotocin is effective against pancreatic tumors. Procarbazine is used to treat Hodgkin's disease and brain tumors, and DTIC is used in treatment of melanoma and lymphomas (Colvin and Cabner, Alkylatingg Agents. In: *Cancer Chemotherapy: Principles and Practice,* Edited by B. A. Chabner and J. M. Collins, Lippincott, Philadelphia, pp. 276–313 (1990); Longo, *Semin. Concol.,* 17, 716–735 (1990)).

DESCRIPTION OF RELATED ART

Chemotherapeutic alkylating agents (e.g.) chloroethylating nitrosoureas) have some clinical utility against a number of neoplasms but in general have only limited effectiveness in killing tumor cells. This is due in part to the protective effect in tumor cells brought about by the DNA repair protein, $O^6$ alkylguanines-alkyltransferase, which repairs alkylation damage to the $O^6$ position of DNA guanine residues. AGT brings about a stoichiometric transfer of the group attached to the $O^6$ position of the modified guanines to a cysteine residue within the alkyltransferase protein (Pegg, *Cancer Research,* 50, pp. 6119–6129, 1990). The resulting alkylated AGT molecule is inactivated for subsequent dealkylation reactions. Since the repair displacement is a bimolecular reaction leading to inactivation of the protein, a cell's repair capacity by this mechanism is dependent on the number of AGT molecules present. Cells with higher AGT content are able to repair greater amounts of damage to the $O^6$ position of DNA guanines than are cells of low AGT content.

Chloroethylating nitrosoureas react with the $O^6$ position of guanine residues and this leads to subsequent formation of cytotoxic interstrand cross-links in the tumor cell DNA. The removal of the initial adduct at guanine $O^6$ by AGT prevents formation of the lethal cross-link lesion. Consequently, cell lines with high levels of AGT exhibit resistance to $O^6$-alkylating anti-tumor drugs while depletion of AGT activity in these cells renders them more sensitive to these alkylating agents (Dolan et al., *Cancer Research,* 51, pp. 3367–3372, (1991)).

Alkyltransferase activity in cells can be depleted either indirectly, by methylation of cellular DNA (Futscher et al., *Cancer Commun.,* 1. pp. 65–73 (1989)) or directly, by exposing cells to alternative substrates for the protein such as $O^6$-benzylguanine (Dolan et al., *Proc. Natl. Acad. Sci. USA,* 87, pp. 5368–5372 (1990)). This agent produces a dramatic and rapid depletion of cellular alkyltransferase activity and has been used to increase the sensitivity of human colon cancer cells (HT29), malignant glioma cells (SF767), and melanoma cells (M19-mel) to the cytotoxic effects of a number of chloroethylating and methylating anti-tumor drugs in vitro (Dolan et al., *Cancer Research,* 51, pp. 3367–3372 (1991)). In addition $O^6$-benzylguanine pretreatment of nude mice bearing human tumor xenografts has been shown to lead to a dramatic increase in the therapeutic effectiveness of chloroethylating nitrosoureas in vivo (Dolan et al., *Cancer Commun.,* 2, pp. 371–377, (1990); Mitchell et al., *Cancer Research,* 52, pp. 1171–1175 (1992)).

Other known $O^6$-benzylguanine derivatives have already been shown to be effective in depleting AGT. These include the $O^6$-benzylguanine of formula A below (Z=H, X=H) (Bowles et al., *J. Med. Chem.*, 6, pp. 471–480 (1963); Frihart and Leonard, *J. Am. Chem. Soc.*, 95, pp. 7174–7175 (1973)), $O^6$-(p-methylbenzyl)guanine (Z=H, X-p-$CH_3$) and $O^6$-(p-chlorobenzyl) guanine (Z=H, X=p-Cl) (Dolan et al., *Proc. Natl. Acad. Sci. USA*, 87, pp. 5368–5372 (1990)), $O^6$-(p-fluorobenzyl) guanine (Z=H, X=p-F) (Moschel et al., *J. Med. Chem.* 35, pp. 4486–4491 (1992)), $O^6$-benzyl-2'-deoxyguanosine (Z=1-β-D-2-deoxyribofuranosyl-, X=H) (Pauly et al., *Chem. Res. Toxicol.*, 1, pp. 391–397 (1988)), $O^6$-benzylguanosine (Z=1-β-D-ribofuranosyl-, X=H) (Gerster and Robins, *J. Am. Chem. Soc.*, 87, pp. 3752–3759 (1965)), $O^6$- (p-methylbenzyl)guanosine (Z=1-β-D-ribofuranosyl-, X=p-$C_3$) and $O^6$-(p-chlorobenzyl)guanosine (Z=1-β-D-ribofuranosyl-, X=p-Cl (Moschel et al., *J. Org. Chem.*, 49, pp. 363–372 (1984).)

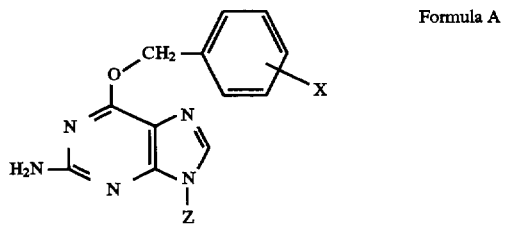

Formula A $O^6$-Allylguanine of formula B below ($X_1=X_2=X_3=X_4=Z_1=H$), $O^6$-(2-butenyl)guanine (formula B, $X_1=X_2=X_3=Z_1=H$, $X_4=CH_3$) (Leonard and Frihart, *J. Am. Chem. Soc.*, 96, pp. 5894–5903 (1974)), $O^6$-cinnamylguanine (formula B, $X_1=X_2=X_3=Z_1=H$, $X_4=C_6H_5$), $O^6$-(m-trifluoromethylcinnamyl)guanine (formula B, $X_1=X_2=X_3=Z_1=H$, $X_4=m$-$CF_3C_6H_4$) and $O^6$-(3-methyl-2-butenyl) guanosine (formula B, $X_1=X_2=H$, $X_3=X_4=CH_3$, $Z_1=1$-β-D-ribofuranosyl) (Holmes and Leonard, *J. Org. Chem.*, 43, pp. 516–518 (1976)) are the only known $O^6$-allylguanine derivatives.

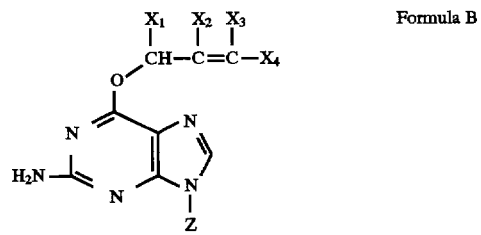

Formula B

SUMMARY OF THE INVENTION

Therefore, it is an object of the present invention to provide additional novel compounds useful for effectively reducing AGT levels in tumor cells.

Another object of the present invention is to provide pharmaceutical compositions containing compounds which effectively reduce AGT levels in tumor cells.

Yet a further object of the present invention is to provide methods for depleting AGT levels in tumor cells.

Still another object of the present invention is to provide methods for increasing host responsiveness to anti-neoplastic chloroethylating agents or other alkylating anti-tumor drugs whose mechanism of action involves modification of the $O^6$ position of DNA guanine residues by administering to the host compositions containing compounds which deplete AGT levels in the tumor cells of the host.

These and other objects of the invention are accomplished by providing novel $O^6$-benzylated guanine derivatives and novel pharmaceutical compositions containing $O^6$-benzylated guanine derivatives. In another aspect, the present invention provides novel $O^6$-allyl guanine derivatives and novel pharmaceutical compositions containing $O^6$-allyl guanine derivatives.

In keeping with the invention, the above described pharmaceutical compositions may, and preferably do, include a pharmaceutically suitable anti-neoplastic alkylating agent and an excipient.

Several of the $O^6$-benzyl and $O^6$-allyl guanine derivatives have been found to be effective in reducing AGT levels in tumor cells and in enhancing the effectiveness of anti-neoplastic alkylating agents.

Further scope of the applicability of the present invention will become apparent from the detailed description and formulas provided below. However, it should be understood that the detailed description and specific examples while indicating preferred embodiments of the invention are given by way of illustration only since various changes and modificatons within the spirit and scope of the invention will become apparent to those skilled in the art from this detailed description.

DETAILED DESCRIPTION OF THIS INVENTION

Compounds encompassed by and useful in the present invention include compounds of the following types as illustrated by formula 1.

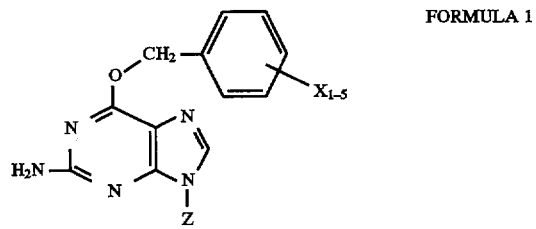

FORMULA 1 wherein each of $X_1$-$X_5$ is selected from the group consisting of hydrogen, halogen, hydroxy, aryl, a $C_1$-$C_8$ alkyl substituted aryl, nitro, a polycyclic aromatic alkyl containing 2–4 aromatic rings wherein the alkyl is a $C_1$-$C_6$, a $C_3$-$C_8$ cycloalkyl, a $C_2$-$C_6$ alkenyl, a $C_2$-$C_6$ alkynyl, a $C_1$-$C_6$ hydroxyalkyl, a $C_1$-$C_8$ alkoxy, a $C_2$-$C_8$ alkoxyalkyl, aryloxy, aryloxy, an acyloxyalkyl wherein the alkyl is $C_1$-$C_6$, amino, a monoalkylamino wherein the alkyl is $C_1$-$C_6$, a dialkylamino wherein the alkyl is $C_1$-$C_6$, acylamino, ureido, thioureido, carboxy, a carboxyalkyl wherein the alkyl is $C_1$-$C_6$, cyano, a cyanoalkyl wherein the alkyl is $C_1$-$C_6$, C-formyl, C-acyl, a dialkoxymethyl wherein the alkoxy is $C_1$-$C_6$, an aminoalkyl wherein the alkyl is $C_1$-$C_6$, and $SO_nR_1$ wherein n=0, 1, 2 or 3, $R_1$ is H, a $C_1$-$C_6$ alkyl or aryl; and wherein Z is selected from the group consisting of methyl, aryl, a substituted aryl wherein the aryl substituents are selected from the group consisting of $C_1$-$C_6$ alkyls, nitro and halo, a polycyclic aromatic alkyl containing 2–4 aromatic rings, $C_1$-$C_6$ alkyl, $C_2$-$C_6$ alkenyl, $C_6$ alkynyl, halomethyl, $C_3$-$C_6$ haloalkyl, $C_1$-$C_3$ hydroxyalkyl, $C_1$-$C_6$ halohydroxy alkyl, acyloxy, an acyloxyalkyl wherein the alkyl is $C_1$-$C_3$, carboxy, the acid and salt forms of carboxyalkyl wherein the alkyl is $C_1$-$C_6$, $C_1$-$C_8$ alkoxy, carbonyl, carbamoyl, a carbamoylalkyl wherein the alkyl is $C_1$-$C_6$, hydrazinocarbonyl, chlorocarbonyl, cyano, $C_2$-$C_9$ cyanoalkyl, C-formyl, a dialkoxymethyl wherein the alkoxy is $C_1$-$C_6$, C-acyl, an alkoxy hydroxyalkyl wherein the alkyl and the alkoxy are $C_1$–$C_4$, carboxymethyl thio, a carboalkoxy alkyl wherein the alkoxy and alkyl are $C_1$–$C_6$, a monoalkylamino hydroxyalkyl wherein the alkyl is $C_1$–$C_6$, a dialkylamino hydroxyalkyl wherein the alkyl is $C_1$–$C_6$, amino hydroxyalkyl wherein the alkyl is $C_1$–$C_6$, a peptide containing the β-lactone of L-serine, a monosaccharide selected from the group consisting of aldotetroses, aldopentoses and aldohexoses, a polysaccharide selected from the group consisting of sucrose, lactose, maltose and cellobiose, a nucleic acid segment selected from the group consisting of 5'-d(AACAGCCATATG*GCCC)-3', 5'-d(GTGGGCGCTG*GAGGCG)-3', 5'-d(GTGGGCGCTGG*GAGGCG)-3', and 5'-d(GTGGGCGCTG*G*AGGCG)-3' wherein G* is $O^6$-benzyl-2'-deoxyguanosine residue, a steroid selected from the group consisting of testosterone, nortestosterone, and dihydrotestosterone, and $SO_nR_1$ wherein n is 0, 1, 2, or 3 and $R_1$ is H, $C_1$–$C_6$ alkyl or aryl.

This invention further provides compounds of the formula 1 wherein Z is 1-β-D-ribofuranoside or 1-β-D-2-deoxyribofuranoside and $X_1$–$X_5$ is each independently selected from the group consisting of $C_2$–$C_8$ alkoxyalkyl, aryloxy, acyloxy, acyloxyalkyl wherein the alkyl is $C_1$–$C_6$, acylamino, and nitro.

This invention also provides compounds of formula 1 where $X_1$–$X_5$ is hydrogen and Z is carboethoxymethyl, the conjugate acid form of a carboxymethyl group, the carboxylate anion of a carboxymethyl group as sodium salt, carbamoyl methyl, 2-hydroxybutyl, cyanomethyl, pivaloyloxymethyl, 3-amino-2-hydroxypropyl, 3-alkylamino-2-hydroxypropyl, and 3-dialkylamino-2-hydroxypropyl.

The present invention also provides compounds of the formula 2:

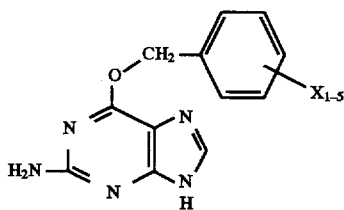

FORMULA 2 wherein $X_1$–$X_5$ are each independently selected from the group consisting of $C_2$–$C_8$ alkoxyalkyl, aryloxy, acyloxy, acyloxyalkyl wherein the alkyl is $C_1$–$C_3$, hydrazino, hydroxyamino, acylamino, nitro at o, m-positions, bromine, m-methyl, $C_1$–$C_3$ hydroxy alkyl, $C_2$–$C_6$ alkyl, C-formyl, and aryl.

This invention also provides compounds of the formula 3:

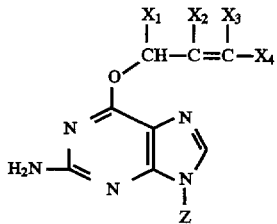

FORMULA 3 wherein $X_1$–$X_4$ are each independently selected from the group consisting of hydrogen, halogen, nitro, aryl, substituted aryl where substituents are selected from the group consisting of $C_1$–$C_6$ alkyl, nitro and halo, polycyclic aromatic containing up to 4 aromatic rings, $C_1$–$C_6$ alkyl, $C_3$–$C_8$ cycloalkyl, $C_2$–$C_8$ alkenyl, $C_1$–$C_6$ haloalkyl, $C_1$–$C_6$ hydroxyalkyl, $C_1$–$C_9$ alkoxy, $C_2$–$C_9$ alkoxyalkyl, aryloxy, acyloxy, acyloxyalkyl wherein the alkyl is $C_1$–$C_6$, amino, monoalkylamino wherein the alkyl is $C_1$–$C_6$, dialkylamino wherein the alkyl is $C_1$–$C_6$, acylamino, carboxy, carboxyalkyl wherein the alkyl is $C_1$–$C_6$, alkoxycarbonyl wherein the alkyl is $C_1$–$C_6$, carbamoyl, cyano, carboxymethylthio, aminocarboxyalkyl wherein the alkyl is $C_1$–$C_6$ and $SO_nR_1$ wherein n=0, 1, 2 or 3 and $R_1$ is H, $C_1$–$C_6$ alkyl or aryl; and Z is selected from the group consisting of aryl, substituted aryl wherein substituents include halogen and nitro, arylalkyl wherein the alkyl is $C_1$–$C_6$, polycyclic aromatic containing up to 4 aromatic rings, $C_2$–$C_6$ alkenyl, $C_2$–$C_6$ alkynyl, $C_1$–$C_6$ haloalkyl, $C_1$–$C_6$ hydroxyalkyl, acyloxy, acyloxyalkyl wherein the alkyl is $C_1$–$C_3$, carboxy, the acid and salt forms a carboxyalkyl wherein the alkyl is $C_1$–$C_3$, $C_2$–$C_6$ alkoxycarbonyl, carbamoyl, carbamoylalkyl wherein the alkyl is $C_1$–$C_6$, hydrazinocarbonyl, chlorocarbonyl, cyano, cyanoalkyl wherein the alkyl is $C_1$–$C_6$, C-formyl, dialkoxymethyl wherein the the alkoxy is $C_1$–$C_6$, C-acyl, carboxymethylthio, $C_3$–$C_{10}$ carboalkoxy alkyl, monoalkylamino hydroxyalkyl wherein the alkyl is $C_1$–$C_6$, and dialkylamino hydroxyalkyl wherein the alkyl is $C_1$–$C_6$, and amino hydroxyalkyl wherein the alkyl is $C_1$–$C_6$.

This invention further provides compounds represented by formula 3 wherein Z is 1-β-D-ribofuranosyl, and $X_1$ and $X_2$ are each independently selected from the group consisting of hydrogen, $C_1$–$C_6$ alkyl, aromatic, polycyclic aromatic of up to 4 rings, substituted aromatic wherein the substituents are selected from group consisting of $C_1$–$C_6$ alkyl, nitro, halo, aryloxy, $C_1$–$C_6$ alkoxy, $C_1$–$C_6$ hydroxyalkyl, acyloxy, $C_3$–$C_8$ cycloalkyl, nitro, halogen, amino, monoalkylamino wherein the alkyl is $C_1$–$C_6$, dialkylamino wherein the alkyl is $C_1$–$C_6$, carboxy, carboxyalkyl wherein the alkyl is $C_1$–$C_6$, alkoxycarbonyl wherein the alkyl is $C_1$–$C_6$, carbamoyl, cyano, carboxymethyl thio, aminocarboxyalkyl wherein the alkyl is $C_1$–$C_6$, and $SO_nR_1$ wherein n=o, 1, 2 or 3 and $R_1$=H, $C_1$–$C_6$ alkyl or aryl, and $X_3$ and $X_4$ are selected from the group consisting of $C_2$–$C_6$ alkyl aromatic, substituted aromatic wherein the substituents chosen from the group consisting of $C_1$–$C_6$ alkyl, nitro and halo, polycyclic aromatic of up to 4 rings, aryloxy, $C_1$–$C_6$ alkoxy, $C_1$–$C_6$ hydroxyalkyl, acyloxy, $C_3$–$C_8$ cycloalkyl, nitro, halogen, amino, monoalkylamino wherein the alkyl is $C_1$–$C_6$, dialkylamino wherein the alkyl is $C_1$–$C_6$, carboxy, carboxyalkyl wherein the alkyl is $C_1$–$C_6$, alkoxycarbonyl wherein the alkyl is $C_1$–$C_6$, cyano, carboxymethyl thio, aminocarboxyalkyl wherein the alkyl is $C_1$–$C_6$, and $SO_nR_1$ wherein n=0, 1, 2 or 3 and $R_1$=H, $C_1$–$C_6$ alkyl or aryl.

In addition, this invention provides compounds represented by formula 4:

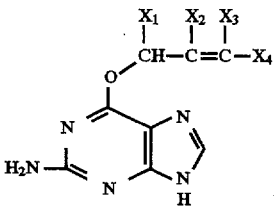

FORMULA 4 wherein $X_1$, $X_2$ and $X_3$ are hydrogen; and $X_4$ is $C_2$–$C_6$, alkyl, nitro, halo, aryl, o, p-substituted aromatic wherein substituents are selected from the group consisting of $C_1$–$C_6$ alkyl, nitro and halo, aryloxy, $C_1$–$C_6$ alkoxy, $C_1$–$C_6$ hydroxyalkyl, acyloxy, $C_3$–$C_8$ cycloalkyl, nitro, halogen, amino, monoalkylamino wherein the alkyl is $C_1$–$C_6$, dialkylamino wherein the alkyl is $C_1-C_6$, carboxy, carboxyalkyl wherein the alkyl is $C_1-C_6$, alkoxycarbonyl wherein the alkyl is $C_1-C_6$, carbamoyl, cyano, carboxymethyl thio, aminocarboxyalkyl wherein the alkyl is $C_1-C_6$, $SO_nR_1$, wherein n=0, 1, 2 or 3 and $R_1$=H, $C_1-C_6$ alkyl or aryl, and meta substituted phenyl wherein the substituent is selected from the group consisting of $C_1-C_6$ alkyl, $C_1-C_6$ chloroalkyl, $C_1-C_6$ bromoalkyl, $C_1-C_6$ iodoalkyl and $C_1-C_6$ fluoroalkyl.

Pharmaceutical compositions comprising the compounds described herein above may also be prepared for reducing AGT levels in tumor cells. Pharmaceutical compositions thus comprise the compound or compounds and a pharmaceutically acceptable excipient.

In keeping with the invention, the above pharmacetical compositions may, and preferably do, contain, in addition, an anti-neoplastic alkylating agent.

In consonance with this invention, a method is disclosed for treating tumor cells in a host which comprises administering to the host an amount effective to reduce AGT activity in this host of a composition containing one or more of the compounds as described above.

In addition, this invention provides a method of enhancing the chemotherapeutic treatment of tumor cells in a host with an anti-neoplastic alkylating agent, which method comprises administering to the host an effective amount of a composition containing the above disclosed $O^6$-substituted guanine compounds and an anti-neoplastic alkylating agent.

This invention further provides a method for treating tumor cells in a host which comprises administering to the host an amount effective to reduce AGT activity in the host of a compound of the formula:

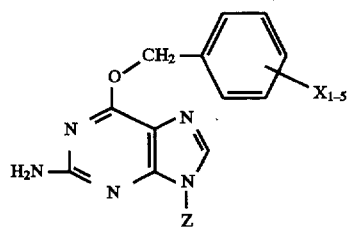

wherein Z is 1-β-D-ribofuranoside or 1-β-D-2-deoxy ribofuranoside and wherein $X_1-X_5$ is selected from the group consisting of $C_2-C_8$ alkoxyalkyl, aryloxy, acyloxy, an acyloxyalkyl wherein the alkyl is $C_1-C_6$, acylamino, and nitro.

This invention additionally provides a method of enhancing the chemotherapeutic treatment of tumor cells in a host with an anti-neoplastic alkylating agent whose mechanism of action involves modification of the $O^6$ position of DNA-guanine residue, which method comprises administering to the host an effective amount of a composition containing an $O^6$-substituted guanine compounds disclosed above, and administering to the host an effective amount of a composition containing an anti-neoplastic alkylating agent whose mechanism of action involves modification of the $O^6$ position of DNA-guanine residue.

In keeping with this invention, a method is provided for treating tumor cells in a host which comprises administering to the host an amount effective to reduce AGT activity in the host of a compound represented by the formula

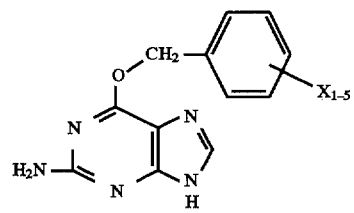

wherein $X_1-X_5$ are each independently selected from the group consisting of halogen, nitro, phenyl, $C_1-C_4$ alkyl substituted phenyl, a $C_1-C_4$ alkyl, a $C_1-C_4$ alkoxy, a $C_2-C_4$ alkenyl, a $C_2-C_4$ alkynyl, an amino, a $C_1-C_4$ monoalkylamino, a $C_1-C_4$ dialkylamino, a trifluoromethyl, hydroxy, hydroxymethyl, and $SO_nR_1$ wherein n is 0, 1, 2, or 3 and $R_1$ is hydrogen, a $C_1-C_4$ alkyl, phenyl, or a $C_1-C_4$ alkyl substituted phenyl.

This invention also provides a method of enhancing the chemotherapeutic treatment of tumor cells in a host with an anti-neoplastic alkylating agent whose mechanism of action involves modification of the $O^6$ position of DNA-guanine residue, which method comprises administering to the host an effective amount of a composition containing an $O^6$-substituted guanine compounds disclosed above, and administering to the host an effective amount of a composition containing an anti-neoplastic alkylating agent whose mechanism of action involves modification of the $O^6$ position of DNA-guanine residue.

Examples of 9-substituted $O^6$-benzylguanine compound derivatives include 2-amino-6-benzyloxy-9-carboethyoxymethylpurine (formula 1, $X_{1-5}$=H, Z=$CH_2CO_2CH_2CH_3$), 2-amino-6-benzyloxy-9-carboxymethylpurine, sodium salt (formula 1, $X_{1-5}$=H, Z=$CH_2CO_2^-Na^+$), 2-amino-6-benzyloxy-9-carbamoylmethylpurine (formula 1, $X_{1-5}$=H, Z=$CH_2CONH_2$), 2-amino-6-benzyloxy-9-(2-hydroxybutyl) purine (formula 1, $X_{1-5}$=H, Z=$CH_2CH(OH) CH_2CH_3$), 2-amino-6-benzyloxy-9-cyanomethylpurine (formula 1, $X_{1-5}$=H, Z=$CH_2CN$), 2-amino-6-benzyloxy-9-pivaloyloxymethylpurine (formula 1, $X_{1-5}$=H, Z=$CH_2OCOC(CH_3)_3$), 2-amino-6-benzyloxy-9-{N-[2-deoxy-2-(1, 3,4,6-tetra-O-acetyl)-D-glucopyranosyl] carbamoylmethyl}purine (formula 1, $X_{1-5}$=H, Z=$C_{16}H_{22}NO_{10}$). All such compounds exhibit AGT depletion characteristics and can be synthesized using appropriate adaptations known to those skilled in the art of the general description presented below.

$O^6$-Benzylguanine or $O^6$-benzylguanine substituted on the benzyl group at either the ortho, meta or para position are the starting materials for the synthesis of the 9-substituted analogs described herein and these starting materials are prepared by treating 2-amino-6-chloropurine with the alkoxide of benzyl alcohol or a substituted benzyl alcohol bearing the desired ortho, meta or para substituent. $O^6$-Benzylguanine was prepared previously by this method (Bowles et al., *J. Med. Chem.*, 6, pp. 471–480 (1963)); Frihart and Leonard, *J. Am. Chem. Soc.*, 95, pp. 7144–7175 (1973)) and related procedures were used to prepare substituted analogs such as $O^6$-(p-methylbenzyl)guanine and $O^6$-(p-chlorobenzyl)guanine (Dolan et al., *Proc. Natl. Acad. Sci. USA*, 87, pp. 5368–5372 (1990)). Treatment of these $O^6$-benzylated guanines in their anionic or neutral forms with alkylating agents such as ethyl bromoacetate, 2-bromoacetamide, 1,2-epoxybutane, bromoacetonitrile, or 1,3,4,6-tetra-O-acetyl-2-deoxy-2-(chloroacetamido)-β-D-glucose (Fondy et al., *J. Med. Chem.*, 21, pp. 1222–1225

(1978)) affords mixtures of both the isomeric 7- and 9-substituted $O^6$-benzylguanine derivative. Since the 9-isomers exhibit greater AGT depleting activity than the corresponding 7-substituted isomer (see below), the former isomers are regarded as more preferred compounds in the context of the present invention.

The synthetic examples provided below indicate that $O^6$-benzylguanine derivatives react readily at both the 7 or 9 positions with a variety of alkylating agents and the two isomeric products are readily separated and purified. It is therefore possible to link a large number of diverse chemical structures to the 7 or 9 position and isolate the more active 9-substituted isomer. Derivatives such as α-amino acid adducts of $O^6$-benzylguanine would be available through nucleophilic displacement by $O^6$-benzylguanine or its anion on selected reagents such as the protected β-lactone of L-serine (Pansare et al., *Org. Syn.*, 70, pp. 1–9 (1991)) or (S)-3-amino-2-oxetanone (Pansare et al., *Org. Syn.*, 70, pp. 10–17 (1991)).

Examples of carbohydrate groups which may be linked to the $O^6$-benzylguanine moiety include, but are not limited to, galactopyranosyl, arabinopyranosyl and mannopyranosyl groups. An example of the synthesis of a glucopyranosyl type carbohydrate $O^6$-benzylguanine derivative is described below. Linkage of $O^6$-benzylguanine to an aromatic heterocycle would be possible by reaction of $O^6$-benzylguanine or its anion with a 5-haloalkylpyrimidine such as 5-bromomethyl- or 5-chloromethyluracil (Carbon, *J. Org. Chem.*, 25, pp. 1731–1734 (1960); Skinner et al., *J. Org. Chem.*, 25., pp. 149–151 (1960)). The attachment of $O^6$-benzylguanine through a linker to a hydroxyl group at a terminal carbohydrate residue of a nucleic acid segment could be accomplished, for example, by reacting 2-amino-6-benzyloxy-9-carboethoxymethylpurine with the hydroxyl group of the terminal carbohydrate residue. The incorporation of $O^6$-benzylguanine in a DNA segment wherein $O^6$-benzylguanine is present as a modified base has already been accomplished as noted above (Pauly et al., *Biochemistry*, 30, pp. 11700–11706 (1991)). The attachment of $O^6$-benzylguanine through a linker to asteroid could be readily accomplished by reacting 2-amino-6-benzyloxy-9-carboethoxymethylpurine (formula 1, $X_{1-5}=H$, $Z\text{-}CH_2CO_2CH_2CH_3$) with the hydroxyl group at position 17 of androgens such as testosterone or dihydrotestosterone (Brix et al., *J. Cancer Res. Clin. Oncol.*, 116, pp. 538–549 (1990)). All such modifications to $O^6$-benzylguanine would be expected to produce an AGT. depleter whose solubility, cellular uptake and metabolism might differ from that of the parent compound $O^6$-benzylguanine. Exploitation of these differences will lead to development of agents that are capable of depleting AGT selectively in tumor cells in preference to normal cells or in particular tumor types.

$O^6$-Allylguanine (formula B, $X_1=X_2=X_3=X_4=Z=H$), $O^6$-(2-butenyl)guanine (formula B, $X_1=X_2=X_3=Z=H$, $X_4=CH_3$) (Leonard and Frihart, *J. Am. Chem. Soc.*, 96, pp. 5894–5903 (1974)), $O^6$-cinnamylguanine (formula B, $X_1=X_2=X_3=Z=H$, $X_4=C_6H_5$), $O^6$-(m-trifluoromethylcinnamyl)guanine (formula B, $X_1=X_2=X_3=Z=H$, $X_4=m\text{---}CF_3C_6H_4$) and $O^6$-(3-methyl-2-butenyl) guanosine (formula B, $X_1=X_2=H$, $X_3=X_4=CH_3$, $Z=1\text{-}\beta\text{-D-ribofuranosyl}$) (Holmes and Leonard, *J. Org. Chem.*, 43, pp. 516–518 (1976)) are known compounds that have been synthesized through reaction of the alkoxide of the appropriate allylic alcohol with 2-amino-6-chloropurine or 2-amino-6-chloropurine riboside. Therefore, by varying substitution on an allylic alcohol for reaction with 2-amino-6-chloropurine, a wide variety of compounds of the type represented by formula B (Z=H) are possible. Subsequent reaction of these with selected alkylating agents will provide 7- and 9-substituted $O^6$-allylguanine or substituted $O^6$-benzylated guanine compounds.

In the methods according to the present invention, pharmaceutical compositions containing compounds according to the present invention are administered to a host in an amount effective to deplete AGT levels in tumor cells of the host thereby increasing host responsiveness to antineoplastic chloroethylating agents or other alkylating antitumor agents. Thus, subsequent or simultaneous administration of anti-neoplastic agents to the host results in effective chemotherapeutic treatment for killing tumor cells. The compounds described herein in accordance with the present invention may be used to reduce AGT levels in the treatment of various neoplasms, such as prostate tumors, brain tumors, lymphomas, leukemias, breast tumors, ovarian tumors, lung tumors, Wilms' tumor, rhabdomyosarcoma, multiplemyeloma, stomach tumors, soft-tissue sarcomas, Hodgkin's disease and non-Hodgkin's lymphomas.

The following Examples illustrate various analytical methods employed to characterize the compounds of the present invention and their AGT depletion activity. The Examples also illustrate the synthesis of many compounds in accordance with the invention.

EXAMPLE 1

Analytical Methods

Proton nuclear magnetic resonance ($^1$H—HMR) and carbon-13 nuclear magnetic resonance ($^{13}$C—NMR) spectra were recorded on a Varian VXR 500S Spectrometer equipped with Sun 4/110 data stations or a Varian XL 200 instrument interfaced to an Advanced data system. Samples were dissolved in dimethyl-$d_6$ sulfoxide with tetramethylsilane as an internal standard. Electron impact (EI) and positive ion (+re) fast atom bombardment (FAB) mass spectra (ms) were obtained with a reversed geometry VG Micromass ZAB-2F spectrometer interfaced to a VG 2035 data system. A mixture of dithiothreitol and dithioerythritol (1:1) was used as FAB matrix. Elemental analyses were performed by Galbraith Laboratories, Inc., Knoxville, Tenn.

EXAMPLE 2

ACT Depletion Experiments

Stock solutions of $O^6$-substituted guanine derivatives were prepared at a concentration of 100 mM in dimethyl sulfoxide (DMSO). Crude extracts from HT29 cells were prepared as described (Domoradzki et al., *Carcinogenesis*, 5, pp. 1641–1647 (1984)) and were incubated for 30 minutes with concentrations between 0 and 400 μm $O^6$-substituted guanine derivative in buffer containing 50 mM Tris-HCl, pH 7.5, 0.1 mM EDTA, 5 mM dithiothreitol. For cell exposure experiments, cells were plated at a density of $5 \times 10^6$ cells/T75 flask and were allowed to grow for 3 days at which time medium was replaced with medium containing increasing concentrations of $O^6$-substituted guanine derivative. After four hours, cells were harvested and frozen at $-80°$ C. until analysis for AGT. Alkyltransferase activity remaining was determined by measuring loss of $O^6$-[$^3$H]methylguanine from a [$^3$H]methylated DNA substrate which was prepared by reacting [$^3$H]methylnitrosourea (21.5 Ci/mmol) with calf thymus DNA as described previously (Domoradzki et al., *Carcinogenesis*, 5, pp. 1641–1647 (1984); Dolan et al., *Proc. Natl. Acad. Sci. USA*, 87, 5368–5372 (1990)).

EXAMPLE 3

2-Amino-6-benzyloxy-7-carboethoxymethylpurine·gl/ $2H_2O$ and 2-amino-6-benzyloxy-9- carboethoxlmethylpurine; (formula 1, $X_{1-5}$=H, Z=$CH_2CO_2CH_3$)

To a 15-mL two-necked flask charged with 0.24 g (1 mmol) of $O^6$-benzylguanine under argon was added 1 mL of a 1M solution of sodium ethoxide in ethanol. The solid dissolved within one minute with stirring. The reaction mixture was kept stirring for an additional 10 minutes. The ethanol was removed under reduced pressure. The resulting solid was redissolved in 2 mL of dry N,N-dimethylformamide (DMF) and the solution was cooled to 0° C. on ice. Ethyl bromoacetate (0.11 mL, 1 mmol) was added dropwise by syringe to the stirring solution and the reaction was allowed to proceed for 30 minutes. The ice bath was then removed and the DMF was removed under vacuum. Separation of the two isomers was achieved by treating the resulting solid with a minimum volume of 5% ethanol in $CHCl_3$ (NaBr does not dissolve in this mixture) and loading the solution on a 2.5×17 cm silica gel column (Davisil grade 633, 200–425 mesh, 60 Å). The 9-substituted isomer was eluted from the column with 5% ethanol in $CHCl_3$, while the 7-substituted isomer was subsequently eluted with 15% ethanol in $CHCl_3$. The recovered solids were precipitated from $CH_2Cl_2$ with hexane.

EXAMPLE 3a

2-Amino-6-benzyloxy-7-carboethoxymethylpurine•½ $H_2O$: Yield, 87 mg (26%); mp 175°–177° C.; $^1$H NMR δ1.04 (t, 3 H, $CH_3$, J=7.1 Hz), 3.97 (q, 2 H, $CH_3CH_2$, J=7.1 Hz), 5.08 (s, 2 H, $CH_2N$<), 5.42 (s, 2 H, $BzlCH_2$), 6.21 (s, 2 H, $NH_2$, exchange with $D_2O$), 7.38 (cm, 1. H, p-ArH), 7.394 (cm, 2 H, m-ArH), 7.436 (cm, 2 H, o-ArH), 8.05 (s, 1, H-8); $^{13}$C NMR δ 13.77 ($CH_3$), 47.59 ($CH_2N$<, 61.09 ($CH_2O_2C$), 66.94 ($BzlCH_2$), 106.07 (C-5), 127.80 (2 o-Ar), 127.95 (p-Ar), 128.32 (2 m-Ar), 136.22 (ipso-Ar), 145.91 (C-8), 156.47 (c-6), 159.74 (C-2), 163.86 (C-4), 168.11 ($CO_2$); MS (EI) Calcd. m/z for $C_{16}H_{17}N_5O_3$: 328.1409. Found: 328.1428 (5 ppm error). Anal. Calcd. for $C_{16}H_{17}N_5O_3$·½ $H_2O$: C, 57.14; H, 5.39; N, 20.46.

2-Amino-6-benzyloxy-7-carboxymethylpurine, sodium salt. A suspension of 0.12 g of 2-amino-6-benzyloxy-7-carboethoxymethylpurine in 5 mL of $H_2O$ containing 0.015 g NaOH was stirred and warmed until all suspended solid dissolved. The solution was then evaporated to dryness and the resulting solid was triturated with ethanol and dried under vacuum to afford 2-amino-6-benzyloxy-7-carboxymethylpurine, sodium salt: UV ($H_2O$) $λ_{max}$ 240 nm (sh), 289 nm; $^1$H NMR (DMSO-$d_6$D$_2$O) δ 4.79 (s, 2 H, $CH_2N$<), 5.54 (s, 2 H, $BzlCH_2$), 7.34–7.61 (cm, 5 H, ArH), 7.98 (s, 1 H, H-8); +ve FAB MS m/z 322 [$C_{14}H_{12}N_5O_3Na$+H]$^+$.

EXAMPLE 3b

2-Amino-6-benzyloxy-9-carboethoxymethylpurine: Yield, 138 mg (42%); mp 163°–164° C.; $^1$H NMR δ 1.21 (t, 3 H, $CH_3CH_2$, J=7.1 Hz), 4.16 (q, 2 H, $CH_3CH_2$, J=7.1 Hz), 4.93 (s, 2 H, $CH_2N$<), 5.50 (s, 2 H, $BzlCH_2$), 6.51 (s, 2, $NH_2$, exchange with $D_2O$), 7.35 (cm, 1 H, p-ArH), 7.40 (cm, 2 H, m-ArH), 7.51 (cm, 2 H, o-ArH0, 7.84 (s, 1 H, H-8); $_{13}$C NMR δ13.96 ($CH_3$), 43.68 ($CH_2N$<), 61.26 ($CH_2O_2C$), 66.86 ($BzlCH_2$), 113.17 (C-5), 128.00 (p-Ar), 128.36 (2 m-Ar), 128.41 (2 o-Ar), 136.60 (ipso-Ar), 140.12 (C-8), 154.54 (C-4), 159.80 (C-2), 160.01 (–6), 167.93 ($CO_2$); MS (EI) Calcd. m/z for $C_{16}H_{17}N_5O_3$: 328.1409. Found: 328.1400 (3 ppm error). Anal. Calcd. for $C_{16}H_{17}N_5O_3$: C, 58.71; H, 5.23; N, 21.40. Found: C, 58.70; H, 5.23; N, 21.25.

2-Amino-6-benzyloxy-9-carboxymethylpurine, sodium salt (formula 1, $X_{1-5}$=H, Z=$CH_2CO_2^-Na^+$). A suspension of 2-amino-6-benzyloxy-9-carboethoxymethylpurine was treated as described above for the 7-substituted isomer to afford 2-amino-6-benzyloxy-9-carboxymethylpurine, sodium salt: UV ($H_2O$) $λ_{max}$ 250 nm, 281 nm; $^1$H NMR (DMSO-$d_6$/$D_2O$) δ4.52 (s, 2 H, $CH_2N$<), 5.59 (s, 2 H, $BzlCH_2$), 7.36–7.59 (cm, 5 H, ArH), 7.81 (s, 1 H, H-8); +ve FAB MS m/z 322 [$C_{14}H_{12}N_5O_3Na$+H]$^+$.

EXAMPLE 4

2-Amino-6-benzyloxy-7-carbamoylmethylpurine•½ $H_2O$ and 2-amino-6-benzyloxy-9-carbamoylmethylpurine; (formula 1, $X_{1-5}$=H, Z=$CH_2CONH_2$)

To 0.5 g (2.1 mmol) of $O^6$-benzylguanine under argon was added 2.2 mL of a 1M solution of sodium ethoxide in ethanol. The solid dissolved within 1 minute. After an additional 10 minutes of stirring the ethanol was removed under vacuum. The remaining solid was dissolved in 10 mL of dry dioxane and the solution was kept at 20° C. in a water bath. 2-Bromoacetamide (0.286 g, 2.2 mmol) was added dropwise to the stirring solution and this was allowed to react for one hour. Dioxane was then removed under vacuum. Separation of the two isomers was achieved by dissolving the resulting solid in 50% aqueous methanol (100 mg/25 mL) and loading this on a 3×80 cm Sephadex LH-20 column eluted with 50% aqueous methanol at 1 mL/min. Column eluent was continuously monitored at 280 nm and fractions (10 mL) were collected. The 7-substituted isomer eluted from the column in fractions 45–57, while the 9-substituted isomer eluted in fractions 65–80. Solid material was recovered after removal of solvent from the respective pooled fractions. Both compounds can be further purified by recrystallization from $CH_3CN$/$H_2O$ through slow evaporation of the solvent.

EXAMPLE 4a

2-Amino-6-benzyloxy-7-carbamoylmethylpurine•½ $H_2O$: Yield, 256 mg (40%); mp 227°–228° C. (decomposition); $^1$H NMR δ4.86 (s, 2 H, $CH_2N$<), 5.46 (s, 2 H, $BzlCH_2$), 6.12 (s, 2 H, $NH_2$, exchange with $D_2O$), 7.26 (bs, 1 H, $H_a$NHCO), 7.32 (cm, 1 H, p-ArH), 7.38 (cm, 2 H, 2 m-ArH), 7.47 (cm, 2 H, 2 o-ArH), 7.60 (bs, 1 H, $H_b$NHCO), 8.01 (s, 1 H, H-8); $^{13}$C NMR δ 48.49 ($CH_2N$<), 66.59 ($BzlCH_2$), 106.48 (C-5), 127.46 (2 o-Ar), 127.69 (p-Ar), 128.31 (2 m-Ar), 136.49 (ipso-Ar), 146.50 (C-8), 156.42 (C-6), 159.44 (C-2), 163.81 (C-4), 168.58 ($CONH_2$); MS (EI) Calcd. m/z for $C_{14}H_{14}N_6O_2$: 298.1178. Found: 298.1169 (3 ppm error). Anal. Calcd. for $C_{14}H_{14}M_6O_2$•½ $H_2O$ C, 54.72; H, 4.92; N, 27.35. Found: C, 54.98; H, 4.97; N, 27.50.

EXAMPLE 4b

2-Amino-6-benzyloxy-9-carbamoylmethylpurine: Yield, 239 mg (38%); mp 243°–244.5° C. (decomposition); $^1$H NMR δ 4.67 (s, 1 H, $CH_2N$<), 5.50 (s, 1 H, $BzlCH_2$), 6.43 (s, 2 H, $NH_2$), 7.26 (bs, 1 H, $H_a$NHCO), 7.35 (cm, 1 H, p-ArH), 7.40 (cm, 2 H, 2 m-ArH), 7.50 (cm, 2 H, 2 o-ArH), 7.63 (bs, 1 H, $H_b$NHCO), 7.78 (s, 1 H, 8-H); $^{13}$C NMR δ 44.59 ($CH_2N$<), 66.75 ($BzlCH_2$), 113.28 (C-5), 127.96 (p-Ar), 128.34 (2 m-Ar), 128.36 (2 o-Ar), 136.72 (ipso-Ar), 140.79 (C-8), 154.70 (C-4), 159.63 (C-2), 159.93 (C-6), 168.30 ($CONH_2$); MS (EI) Calcd. m/z for $C_{14}H_{14}N_6O_2$: C, 56.37; H, 4.73; N, 28.17. Found: C, 56.77; H, 4.83; N, 28.34.

EXAMPLE 5

2-Amino-6-benzyloxy-7-(2-hydroxybutyl) purine and 2-amino-6-benzyloxy-9-(2-hydroxybutyl)purine; (formula 1, $X_{1-5}$=H, Z=$CH_2CH(OH)CH_2CH_3$)

To 0.24 g (1 mmol) of O$^6$-benzylguanine, in 3 mL of ethanol was added 0.14 g of potassium carbonate (1 mmol) and 0.85 mL (10 mmol) 1,2-epoxybutane. The reaction mixture was heated to reflux with stirring for 1.5 hours. The solution was filtered, and solvent and excess epoxide were removed under vacuum. The isomeric 7- and 9-substituted derivatives were separated by treating the solid residue with a minimum volume of 7% ethanol in CHCl$_3$ and loading the soluble material on a 2.5×17 cm silica gel column (Davisil grade 633, 200–425 mesh, 60 Å). The 9-substituted isomer eluted from the column with 7% ethanol in CHCl$_3$, while the 7-substituted isomer was subsequently eluted with 15% ethanol in CHCl$_3$. The 9-substituted isomer was further purified by precipitation from CH$_2$Cl$_2$ with hexane.

EXAMPLE 5a

2-Amino-6-benzyloxy-7-(2-hydroxybutyl)purine: Yield, 64 mg (20%); mp 200°–202° C.; $^1$H NMR δ 0.74 (t, 3 H, CH$_3$, J=7.5 Hz), 1.25 (cm, 2 H, CH$_2$CH$_3$), 3.58 (cm, 1 H, CHOH), 3.90 (dd, 1 H, H$_a$CH<N, $^2$J=13.8 Hz, $^3$J=8.8 Hz), 4.14 (dd, 1 H, H$_b$CH<N, $^2$J=13.8 Hz, $^3$J=3.1 Hz), 4.84 (d, 1 H, CHOH, J=5.8 Hz), 5.40 (d, 1 H, BzlH$_a$CH, $^2$J=12.2 Hz), 5.53 (d, 1 H, BzlH$_b$CH, $^2$J=12.2 Hz), 6.12 (s, 2 H, NH$_2$), 7.34–7.42 (cm, 3 H, p,m-ARH), 7.51 (cm, 2 H, 2 o-ArH), 7.97 (s, 1 H, H-8); $^{13}$C NMR δ9.44 (CH$_3$), 27.18 (CH$_2$CH$_3$), 52.42 (CH$_2$N<), 66.91 (BzlCH$_2$), 70.28 (CHOH), 105.73 (C-5), 127.93 (2 o-Ar), 128.10 (p-Ar), 128.24 (2 m-Ar), 136.29 (ipso-Ar), 146.11 (s, C-8), 156.24 (C-6), 159.25 (C-2), 163.94 (C-4); MS (EI) Calcd. m/z for C$_{16}$H$_{19}$N$_5$O$_2$: C, 61.33; H, 6.11; N, 22.35. Found: C, 61.69; H, 6.12; N, 22.41.

EXAMPLE 5b

2-Amino-6-benzyloxy-9-(2-hydroxybutyl)purine: Yield, 44 mg (14.0%); mp 178°–180° C.; $^1$H NMR δ 0.90 (t, 3 H, CH$_3$, J=7.3 Hz), 1.29 (cm, 1 H, CH$_a$HCH$_3$, $^3$J=7.4 Hz, $^3$J =7.4 Hz, $^2$J=13.8 Hz) 1.39 (cm, 1 H, CH$_b$HCH$_3$, $^3$J=4.2 Hz, $^3$J=7.4 Hz, $^2$J=13.8 Hz), 3.72 (cm, 1 H, CHOH), 3.88 (dd, 1 H, CH$_a$HN<, $^3$J=7.9 Hz, $^2$J=13.8 Hz), 4.00 (dd, 1 H, CH$_b$HN<, $^3$J=3.9 Hz, $^2$J=13.9 Hz), 4.98 (bs, 1 H, CHOH), 5.49 (d, 1 H, BzlCH$_a$H, $^2$J-12.3 Hz), 5.50 (d, 1 H, BzlCH$_b$H, $^2$J-12.3 Hz), 6.42 (s, 2 H, NH$_2$), 7.35 (t, 1 H, p-ArH, J=7.3 Hz), 7.40 (t, 2 H, m-ArH, J=7.4 Hz), 7.50 (d, 2 H, o-ArH, J=7.0 Hz), 7.79 (s, 1 H, H-8); $^{13}$C NMR δ9.74 (CH$_3$), 27.27 (CH$_2$CH$_3$), 48.58 (CH$_2$N<), 66.78 (BzlCH$_2$), 69.44 (CHOH), 113.19 (C-5), 127.98 (p-Ar), 128.36 (2 m-Ar), 128.41 (2 o-At), 136.68 (ipso-Ar), 140.58 (C-8), 154.47 (C-4), 159.56 (C-2), 159.85 (C-6); MS (EI) Calcd. m/z for C$_{16}$H$_{19}$N$_5$O$_2$: 313.1538. Found: 313.1516 (7 ppm error). Anal. Calcd. for C$_{16}$H$_{19}$N$_5$O$_2$: C, 61.33; H, 6.11; N, 22.35. Found: C, 61.11; H, 6.24; N, 22.10.

EXAMPLE 6

2-Amino-6-benzyloxy-7-cyanomethylpurine and 2-amino-6-benzyloxy-9-cyanomethylpurine; (formula 1, X$_{1-5}$=H, Z=CH$_2$CN)

To 0.24 g (1 mmol) of O$^6$-benzylguanine under argon was added 1 mL of a 1M solution of sodium ethoxide in ethanol. The solid dissolved within one minute with stirring. The reaction mixture was stirred for an additional 10 minutes and the ethanol was removed under vacuum. The remaining solid was dissolved in 2 mL of dry DMF and the solution cooled to 0° C. on ice. Bromoacetonitrile (0.07 ml, 1 mmol) was added dropwise to the stirring solution by syringe and this mixture was allowed to react for 30 minutes. At this point, the ice bath was removed and the DMF was removed under vacuum. The 7- and 9-substituted isomers were separated by treating the solid residue with a minimum volume of 5% ethanol in CHCl$_3$ and loading the soluble material on a 4×38 cm silica gel column (Davisil grade 633, 200–425 mesh, 60 Å). The 9-substituted isomer eluted from the column with 15% ethanol in CHCl$_3$, while the 7-substituted isomer was subsequently eluted with 20% ethanol in CHCl$_3$. Both compounds were precipitated from CH$_2$Cl$_2$ with hexane.

EXAMPLE 6a

2-Amino-6-benzyloxy-7-cyanomethylpurine: Yield, 98 mg (35%); mp 188°–189° C.; $^1$H NMR δ 5.43 (s, 2 H, CH$_2$N<), 5.52 (s, 2 H, BzlCH$_2$), 6.33 (s, 2 H, NH$_2$), 7.33 (cm, 1 H, p-ArH), 7.39 (cm, 2 H, 2 m-ArH), 7.56 (cm, 2 H, 2 o-ArH), 8.17 (s, 1 H, H-8); $^{13}$C NMR δ34.71 (CH$_2$N<), 67.19 (BzlCH$_2$), 105.07 (C-5), 115.94 (CN), 127.91 (2 o-Ar), 127.93 (p-Ar), 128.34 (2 m-Ar), 136.20 (ipso-Ar), 145.57 (C-8), 156.44 (C-6), 160.11 (C-2), 164.10 (C-4); MS (EI) Calcd. m/z for C$_{14}$H$_{12}$N$_5$O: 280.1072. Found: 280.1088 (5.7 ppm error). Anal. Calcd. for C$_{14}$H$_{12}$N$_5$O: C, 59.99; H, 4.32, 29.98. Found: C, 59.75; H, 4.43; N, 29.61.

EXAMPLE 6b

2-Amino-6-benzyloxy-9-cyanomethylpurine: Yield, 114 mg (41%); mp 191° C. (decomposition); $^1$H NMR δ5.28 (s, 2 H, CH$_2$N<), 5.51 (s, 2 H, BzlCH$_2$), 6.69 (s, 2 H, NH$_2$), 7.35 (cm, 1 H, p-ArH), 7.40 (cm, 2 H, 2 m-ArH), 7.50 (cm, 2 H, 2 o-ArH), 7.93 (s, 1 H, 8-H); $^{13}$C NMR δ30.75 (CH$_2$N<), 67.00 (BzlCH$_2$), 113.20 (C-5), 115.73 (CN), 128.05 (p-Ar), 128.38 (2 m-Ar), 128.43 (2 o-Ar), 136.47 (ipso-Ar), 138.82 (C-8), 153.92 (C-4), 160.08 (C-2), 160.18 (C-6); MS (EI) Calcd. m/z for C$_{14}$H$_{12}$N$_6$O: C, 59.99; H, 4.32, 29.98. Found: C, 59.76; H, 4.37; N, 29.88.

EXAMPLE 7

2-Amino-6-benzyloxy-9-pivaloyloxymethylpurine (formula 1, X$_{1-5}$=H, Z=CH$_2$OCOC(CH$_3$)$_3$)

To 0.24 g (1 mmol) of O$^6$-benzylguanine under argon was added 1 mL of a 1M solution of sodium ethoxide in ethanol. The homogeneous solution was stirred for 10 minutes. The ethanol was then removed under vacuum. The remaining solid was dissolved in 2 mL of dry DMF. Chloromethyl pivalate (0.145 ml, 1 mmol) was added dropwise to the stirred solution. The mixture was allowed to react for 30 minutes at room temperature. The DMF was removed under vacuum. The residue was triturated with a small volume of 10% ethanol in CHCl$_3$ and the soluble material was loaded on a 2.5×17 cm silica gel column (Davisil grade 633, 200–425 mesh, 60 Å). The product was eluted with 10% ethanol in CHCl$_3$. Yield, 257 mg (72%); mp 161°–162° C.; $^1$H NMR δ1.09 (s, 9 H, (CH$_3$)$_3$), 5.48 (s, 2 H, CH$_2$N<), 5.96 (s, 2 H, BzlCH$_2$), 6.64 (s, 2 H, NH$_2$), 7.34 (cm, 1 H, p-ArH), 7.39 (cm, 2 H, 2 m-ArH), 7.50 (cm, 2 H, 2 o-ArH), 7.92 (s, 1 H, 8-H); $^{13}$C NMR δ26.51 ((CH$_3$)$_3$), 38.20 (C(CH$_3$)$_3$), 65.13 (CH$_2$N), 66.94 (BzlCH$_2$), 113.11 (C-5), 128.05 (p-Ar), 128.38 (2 m-Ar), 128.47 (2 o-Ar), 136.50 (ipso-Ar), 139.96 (C-8), 154.30 (C-4), 160.11 (C-2), 160.18 (C-6), 176.96 (CO$_2$); MS (EI) Calcd. m/z for C$_{18}$H$_{21}$N$_5$O$_3$: 355.1644. Found: 355.1660 (5 ppm error). Anal. Calcd. for C$_{18}$H$_{21}$N$_5$O$_3$: C, 60.83; H, 5.96; N, 19.71. Found: C, 61.11; H, 6.07; N, 19.64.

EXAMPLE 8

2-Amino-6-benzyloxy-9-{N-[2-deoxy-2-(1,3,4,6-tetra-O-acetyl)-D-glucopyranosyl]carbamoylmethyl}purine (formula 1, X$_{1-5}$=H, Z=C$_{16}$H$_{22}$NO$_{10}$)

To 0.24 g 1 mmol of $O^6$-benzylguanine under argon was added 1 mL of a 1M solution of sodium ethoxide in ethanol. The solid dissolved within a minute with stirring and the solution was kept stirring for an additional 10 minutes. The ethanol was then removed under vacuum. The remaining solid was dissolved in 2 mL of dry DMF. 1,3,4,6-Tetra-O-acetyl-2-deoxy-2-(chloroacetamido)-β-D-glucose (0.42 g, 1 mmol) (Fondy et al., *J. Med. Chem.*, 21, pp. 1222–1225 (1978)) was added. The mixture was allowed to react overnight at room temperature. The DMF was then evaporated under vacuum. The 9-substituted isomer was purified by treating the solid residue with a minimum volume of 10% ethanol in $CHCl_3$ and loading the soluble material on a 2.5×25 cm silica gel column (Davisil grade 633, 200–425 mesh, 60 Å). The product eluted with 10% ethanol in $CHCl_3$. After removal of solvents, the resulting solid was dissolved in ≈3 mL of $CH_2Cl_2$ and 10 mL of diethylether was carefully layered on top. Crystallization of the product occurred as the solvents slowly mixed overnight. Yield, 200 mg (32%). Based on the $^1H$ NMR data (see below) the ratio of α:β anomer was 1:4. Mp 160–161, 170°–173° C. (decomposition); $^1H$ NMR (for the β anomer) δ1.94 (s, 3 H, $CH_3CO_2$), 1.97 (s, 3 H, $CH_3CO_2$), 2.00 (s, 3 H, $CH_3CO_2$), 2.05 (s, 3 H, $CH_3CO_2$), 3.98 (ddd, 1 H, H-2', J=8.8, 9.3, 10.6 Hz), 3.99 (dd, 1 H, $H_a$-6', J=2.2, 12.4 Hz), 4.03 (ddd, 1 H, 3 H, $CH_3CO_2$), 2.00 (s, 3 H, $CH_3CO_2$), 2.21 (s, 3 H, $CH_3CO_2$), 4.00 (dd, 1 H, $H_a$-6', J=2.2, 12.4 Hz), 4.14 (ddd, 1 H, H-5', J=2.2, 3.9, 10.0 Hz), 4.18 (dd, 1 H, $H_b$-6', J=4.5, 12.4 Hz), 4.29 (ddd, 1 H, H-2', J=3.6, 8.0, 11.0 Hz), 4.67 (d, 1 H, $H_a$CHN<, J=17.0 Hz), 4.71 (d, 1 H, $H_b$CHN<, J=17.0 Hz), 5.01 (dd, 1 H, H-4', J=9.5, 10.1 Hz), 5.21 (dd, 1 H, H-3', J=9.5, 10.9 Hz), 5.50 (s, 2 H, $BzlCH_2$) 5.98 (d, 1 H, H-1', J=3.5 Hz) 6.33 (s, 2 H, $NH_2$), 7.35 (cm, 1 H, p-ArH), 7.40 (cm, 2 H, m-ArH), 7.50 (cm, 2 H, o-ArH), 7.74 (s, 1 H, H-8), 8.44 (d, 1 H, CONH, J=9.1 Hz); $^{13}C$ NMR δ20.34 ($CH_3CO_2$), 20.35 ($CH_3CO_2$), 20.46 ($CH_3CO_2$), 20.86 ($CH_3CO_2$), 44.43 ($CH_2$<), 50.12 (C-2'), 61.32 (C-6'), 66.82 ($BzlCH_2$), 67.88 (C-4'), 69.08 (C-5'), 69.98 (C-3'), 89.61 (C-1'), 113.21 (C-5), 128.0 (p-Ar), 128.38 (2 o-Ar, 2 m-Ar), 136.66 (ipso-Ar), -140.66 (C-8), 154.60 (C-4), 159.60 (C-2), 159.96 (C-6), 167.26 (CONH), 169.12 ($CO_2CH_3$), 169.14 ($CO_2CH_3$), 170.00 ($CO_2CH_3$), 170.02 ($CO_2CH_3$); MS (+ve FAB) Calcd. m/z for $[C_{28}H_{32}N_6O_{11}+H]_+$: 629.2205. Found: 629.2190 (2 ppm error). Anal. Calcd. for $C_{28}H_{32}N_6O_{11}$: C, 53.50; H, 5.13; N, 13.37. Found: C, 53.12; H, 5.05; N, 13.21.

Ultraviolet absorption data for several of these compounds are presented in Table 1.

TABLE 1

Ultraviolet absorption data

| Example | Compound No. | formula[a] | acid[b] (0.1 HCl) | | neutral[c] (pH 6.9) | | alkaline (0.1N NaOH) | |
|---|---|---|---|---|---|---|---|---|
| | | | $\lambda_{max}$, nm | $10^{-4}\epsilon$ | $\lambda_{max}$, nm | $10^{-4}\epsilon$ | $\lambda_{max}$, nm | $10^{-4}\epsilon$ |
| 3b | 2-amino-6-benzyloxy-9-carboethoxymethylpurine | $C_{16}H_{17}N_5O_3$ | 244 | 0.740 | 248 | 0.953 | 251[d] | 0.830 |
| | | | 290 | 0.951 | 282 | 1.045 | 282 | 1.024 |
| 3a | 2-amino-6-benzyloxy-7-carboethoxymethylpurine | $C_{16}H_{17}N_5O_3 \cdot 1/2H_2O$ | 240 sh[e] | 0.707 | 240 sh | 0.763 | 242[d] sh | 0.777 |
| | | | 290 | 1.203 | 294 | 0.755 | 292 | 0.809 |
| 4b | 2-amino-6-benzyloxy-9-carbamoylmethylpurine | $C_{14}H_{14}N_6O_2$ | 243 | 0.762 | 249 | 0.937 | 249 | 0.905 |
| | | | 292 | 0.994 | 282 | 1.060 | 282 | 1.023 |
| 4a | 2-amino-6-benzyloxy-7-carbamoylmethylpurine | $C_{14}H_{14}N_6O_2 \cdot 1/2H_2O$ | 240 sh | 0.604 | 241 sh | 0.820 | 241 sh | 0.713 |
| | | | 290 | 1.144 | 293 | 0.848 | 293 | 0.762 |
| 5b | 2-amino-6-benzyloxy-9-(2-hydroxybutyl)purine | $C_{16}H_{19}N_5O_2$ | 243 | 0.774 | 250 | 0.769 | 250 | 0.760 |
| | | | 291 | 0.998 | 282 | 0.969 | 282 | 0.954 |
| 5a | 2-amino-6-benzyloxy-7-(2-hydroxybutyl)purine | $C_{16}H_{19}N_5O_2$ | 240 sh | 0.707 | 241 sh | 0.837 | 242 sh | 0.682 |
| | | | 290 | 1.138 | 292 | 0.845 | 292 | 0.707 |
| 6b | 2-amino-6-benzyloxy-9-cyanomethylpurine | $C_{14}H_{12}N_6O$ | 246 | 0.802 | 249 | 1.127 | 249 | 0.970 |
| | | | 290 | 0.941 | 282 | 1.122 | 282 | 1.062 |
| 6a | 2-amino-6-benzyloxy-7-cyanomethylpurine | $C_{14}H_{12}N_6O$ | 239 sh | 0.818 | 240 sh | 0.778 | 242 sh | 0.695 |
| | | | 290 | 1.228 | 294 | 0.745 | 294 | 0.729 |

[a]Satisfactory analytical data were obtained for all compounds (see example descriptions).
[b]Spectra recorded within 2 min after preparation of the acid solution.
[c]0.05M $KH_2PO_4$—$Na_2HPO_4$ buffer.
[d]This value is that for the carboxylate anion.
[e]An sh denotes shoulder.

H-5', J=2.2, 4.5, 9.9 Hz) 4.18 (dd, 1 H, $H_b$-6', J=4.5, 12.4 Hz), 4.64 (d, 1 H, $H_a$CHN<, J=16.9 Hz), 4.67 (d, 1 H, $H_b$CHN<, J=16.9 Hz), 4.89 (dd, 1 H, H-4', J=9.4, 9.9 Hz), 5.20 (dd, 1 H, H-3', J=9.4, 10.6 Hz), 5.50 (s, 2 H, $BzlCH_2$), 5.73 (d, 1 H, H-1', J=8.8 Hz), 6.33 (s, 2 H, $NH_2$); 7.35 (cm 1 H, p-ArH), 7.40 (cm, 2 H, m-ArH), 7.50 (cm, 2 H, o-ArH), 7.74 (s, 1 H, H-8), 8.34 (d, 1 H, NHCO, J=9.3 Hz); $^{13}C$ NMR δ20.27 ($CH_3CO_2$), 20.36 ($CH_3CO_2$), 20.45 ($CH_3O_3$), 20.48 ($CH_3CO_2$), 44.77 ($CH_2N<$), 52.09 (C-2'), 61.44 (C-6'), 66.82 ($BzlCH_2$), 68.07 (C-4'), 71.47 (C-5'), 71.90 (C-3'), 91.54 (C-1'), 113.28 (C-5), 128.0 (p-Ar), 128.38 (2 o-Ar, 2 m-Ar), 136.66 (ipso-Ar), 140.52 (C-8), 154.60 (C-4), 159.67 (C-2), 159.96 (C-6), 167.00 (CONH), 168.91 ($CO_2CH_3$), 169.20 ($CO_2CH_3$), 169.67 ($CO_2CH_3$), 169.97 ($CO_2CH_3$). $^1H$ NMR (for the α anomer) δ1.97 (s, 3 H, $CH_3CO_2$), 1.99 (s,

EXAMPLE 9

$O^6$-(p-Bromobenzyl)guanine

Sodium hydride (21 mmol), 4-bromobenzyl alcohol (21 mmol) and 1,4-dioxane (50 mL) were stirred at room temperature for 2 hr and at 40° C. until all NaH had reacted. 2-Amino-6-chloropurine (10 mmol) was then added and the mixture was refluxed for 20 hr. The solution was evaporated to dryness and the residue was suspended in 100 mL of $H_2O$. Insoluble material was filtered and washed with 50 mL of 1N NaOH. The pH of the combined filtrates was adjusted to pH 6 with glacial acetic acid and water was added to a final volume of 200 mL. The suspension was heated to boiling, treated with charcoal and filtered. On cooling a tan precipitate of crude product was filtered. This material was crystallized from ethanol/H$_2$O (1:3) and dried to afford analytically pure 9: yield, 0.43 g (13%); mp 235°–240° C. (dec.); UV (pH 1) $\lambda_{max}$ 226 nm (sh) ($\epsilon$=2.141×10$^4$), 288 nm ($\epsilon$=1.144×10$^4$), (pH 6.9) 226 nm (sh) ($\epsilon$=1.794×10$^4$), 244 nm (sh) ($\epsilon$=0.765×10$^4$), 282 nm ($\epsilon$=0.877×10$^4$), (pH 13) 248 nm (sh) ($\epsilon$=0.462×10$^4$), 285 nm ($\epsilon$=0.879×10$^4$); $^1$H NMR $\delta$5.47 (s, 2 H, BzlCH$_2$), 6.28 (s, 2 H, NH$_2$), 7.47 (d, 2 H, ArH), 7.59 (d, 2 H, ArH), 7.84 (s, 1 H, H-8), 12.48 (s, 1 H, >NH); $^{13}$C NMR $\delta$65.81 (ArCH$_2$), 121.08 (p-Ar), 128.49 (C-5), 130.50 (2 Ar), 130.83 (ipso-Ar), 131.25 (2 Ar), 136.22 (C-8), 138.4 (C-4), 159.3 (C-2), 159.52 (C-6); MS (EI) calcd m/z for C$_{12}$H$_{10}$N$_5$O$^{79}$Br 319.0068, found 319.0067; calcd m/z for C$_{12}$H$_{10}$N$_5$O$^{81}$Br 321.0048, found 321.0066; Anal. (C$_{12}$H$_{10}$N$_5$OBr) C, 45.02 H, 3.15 N, 21.88 Br, 24.96, found C, 45.05 H, 3.25 N, 21.30 Br, 24.86.

EXAMPLE 10

O$^6$- (p-Isopropylbenzyl)guanine (10a), O$^6$-(p-n-Butylbenzyl) guanine (10b), O$^6$- (p-Phenylbenzyl)guanine (10c), O$^6$-(3,5-Dimethylbenzyl)guanine (10d)

Compounds 10a, 10b, 10c, and 10d were prepared by reacting the sodium salts of 4-isopropylbenzyl oxide, 4-n-butylbenzyl oxide, 4-phenylbenzyl oxide, and 3,5-dimethylbenzyl oxide and 2-pyridylmethoxide (derived in each case by reaction of NaH with the respective alcohol) with 2-amino-6-chloropurine in 1,4-dioxane essentially as described for preparation of 9. After removal of the dioxane by evaporation, the solid residues were dissolved either 200 mL EtOH/H$_2$O (1:1) (for the case of 10a), 125 mL of EtOH/H$_2$O (4:6) (for the case of 10b), or 35 mL of EtOH/H$_2$O (3:7) (for the case of 10d). Crude product 10c was dissolved in aqueous 1N NaOH and was extracted with CH$_2$Cl$_2$. The pH of the resulting solutions of all crude products was then adjusted to pH 6 with glacial acetic acid. Crude 10c was recovered by filtration. The neutral suspensions of products 10a, 10b, and 10d were heated to boiling and treated with charcoal and filtered. After cooling or standing at room temperature overnight the precipitated products were collected by filtration. Compound 10a was crystallized from 50 mL of EtOH/H$_2$O (1:1). Yield: 1.2 g (45.5%); mp 99°–102° C.; UV (pH 1) $\lambda_{max}$ 239 nm (sh) ($\epsilon$=0.787×10$^4$), 287 nm ($\epsilon$=1.219×10$^4$), (pH 6.9) 240 nm ($\epsilon$=0.913×10$^4$), 282 nm ($\epsilon$=0.964×10$^4$), (pH 13) 250 nm (sh) ($\epsilon$=0.466×10$^4$), 286 nm ($\epsilon$=0.889×10$^4$); $^1$H NMR $\delta$1.20 (d, 6 H, CH$_3$, $^3$J=7.0 Hz), 2.89 (septet, 1 H, CH, $^3$J=6.9 Hz), 5.44 (s, 2 H, ArCH$_2$), 6.27 (s, 2 H, NH$_2$), 7.26 (d, 2 H, Ar-H), 7.43 (d, 2 H, Ar-H), 7.83 (s, 1 H, H-8), 12.45 (s, 1 H, >NH); $^{13}$C NMR $\delta$23.84 (2 CH$_3$), 33.19 (CH), 66.61 (ArCH$_2$), 110.25 (C-5), 126.25 (2 Ar), 127.02 (p-Ar), 128.88 (2 Ar), 134.12 (ipso-Ar), ~138 (bs, C-8), 148.29 (C-4), 159.61 (C-2, C-6); MS (EI) calcd m/z for C$_{15}$H$_{17}$N$_5$O 283.1431, found 283.1434; Anal. (C$_{15}$H$_{17}$N$_5$O) C, 63.59; H, 6.05.; N, 24.72. Found: C, 64.14; H, 6.03; N, 24.40. Product 10b was purified by crystallization from 50 mL of EtOH/H$_2$O (1:1). Yield: 0.7 g (28%); mp 122°–125° C.; UV (pH 1) $\lambda_{max}$ 239 nm (sh) ($\epsilon$=0.615×10$^4$), 288 nm ($\epsilon$=0.791×10$^4$), (pH 6.9) 240 nm ($\epsilon$=0.752×10$^4$), 285 nm ($\epsilon$=0.657×10$^4$), (pH 13) 247 nm (sh) ($\epsilon$=0.423×10$^4$), 287 nm ($\epsilon$=0.650×10$^4$); $^1$H NMR $\delta$0.89 (t, 3 H, CH$_3$, $^3$J=7.4 Hz), 1.30 (sextet, 2 H, Me—CH$_2$, $^3$J=7.4–7.5 Hz), 1.55 (m, 2 H, —CH$_2$—), 2.58 (t, 2 H, Ar—CH$_2$—, $^3$J=7.7 Hz), 5.43 (s, 2 H, ArCH$_2$O), 6.28 (s, 2 H, NH$_2$), 7.21 (d, 2 H, Ar-H), 7.40 (d, 2 H, Ar-H), 7.80 (s, 1 H, H-8), 12.40 (s, 1 H, >NH); $^{13}$C NMR $\delta$13.72 (CH$_3$), 21.67 (CH$_2$), 33.09 (CH$_2$), 34.51 (Ar—CH$_2$), 66.59 (ArCH$_2$O), 113.48 (C-5), 128.25 (2 Ar), 128.58 (2 Ar), 133.96 (p-At), 137.70 (ipso-Ar), 142.19 (C-8), 155.13 (C-4), 159.63 (C-2, C-6); MS (EI) calcd m/z for C$_{16}$H$_{19}$N$_5$O 297.1589, found 297.1576; Anal. (C$_{16}$H$_{19}$N$_5$O) C, H, N. Compound 10c was purified by crystallization from EtOH/H$_2$O (1:1) with charcoal treatment. Yield: 0.8 g (47%); mp 219°–220° C. (dec.); UV (pH 1) $\lambda_{max}$ 254 nm ($\epsilon$=1.870×10$^4$), 285 nm (sh) ($\epsilon$=1.154×10$^4$), (pH 6.9) 250 nm ($\epsilon$=1.518×10$^4$), 285 nm (sh) ($\epsilon$=0.921×10$^4$), (pH 13) 252 nm ($\epsilon$=1.965×10$^4$), 285 nm (sh) ($\epsilon$=1.062×10$^4$); $^1$H NMR: $\delta$5.54 (s, 2 , ArCH$_2$), 6.31 (s, 2 H, NH$_2$), 7.37 (t, 1 H, ArH), 7.47 (t, 2 H, ArH), 7.59 (d, 2 H, ArH), 7.68 (t, 4 H, ArH), 7.82 (s, 1 H, H-8), 12.43 (s, 1 H, >NH); $^{13}$C NMR: $\delta$66.34 (ArCH$_2$), 110.17 (C-5), 127.46 (p-Ar), 128.88 (4 Ar), 128.99 (4 Ar), 135.93 (ipso-Ar), 137.8 (C-8), 139.76 (2 ipso-Ar), 139.82 (C-4), 159.58 (C-2, C-6); MS (EI) calcd m/z for C$_{18}$H$_{15}$N$_5$O 317.1276, found 317.1261; Anal. (C$_{18}$H$_{15}$N$_5$O) C, H, N. Compound 10d was purified by crystallization from EtOH/H$_2$O (1:3). Yield: 0.8 g (29%); mp 175°–178° C. (waxes) >230° C. (dec.); UV (pH 1) $\lambda_{max}$ 237 nm (sh) ($\epsilon$=0.670×10$^4$), 288 nm ($\epsilon$=1.174×10$^4$), (pH 6.9) 241 nm ($\epsilon$=0.763×10$^4$), 282 nm ($\epsilon$=0.879×10$^4$), (pH 13) 247 nm (sh) ($\epsilon$=0.494×10$^4$), 285 nm ($\epsilon$=0.980×10$^4$); $^1$H NMR $\delta$2.28 (S, 6 H, CH$_3$), 5.40 (s, 2 H, ArCH$_2$), 6.29 (s, 2 H, NH$_2$), 6.97 (s, 1 H, ArH), 7.09 (s, 2 H, ArH), 7.81 (s, 1 H, H-8), 12.42 (s, 1 H, >NH); $^{13}$C NMR $\delta$20.84 (2 CH$_3$), 66.74 (ArCH$_2$), 113.48. (C-5), 126.06 (2 o-Ar), 129.30 (p-Ar), 136.49 (2 m-Ar), 137.35 (C-8), 137.72 (ipso-Ar), 155.1 (C-4), 159.59 (C-2), 159.8 (C-6); MS (EI) calcd m/z for C$_{14}$H$_{15}$N$_5$O 269.1276, found 269.1264.

EXAMPLE 11

O$^6$-(p-Hydroxymethylbenzyl)guanine 1,4-Benzenedimethanol (10 g) was melted under argon in a 100-mL round bottom flask in a 130° C. oil bath. Sodium (13 mmol) was added in portions, When all sodium had reacted with the 1,4-benzenedimethanol, the bath temperature was lowered to 110° C. and 2-amino-6-chloropurine (6.4 mmol) was added. The suspension was stirred for 24 hr at 110° C. At this time the solution was poured into H$_2$O (250 mL) with constant stirring for 30 min. Undissolved solid was removed by filtration and the filtrate was neutralized with glacial acetic acid. The precipitate that formed was collected by filtration and crystallized from 100 mL MeOH/H$_2$O (1:1) to produce analytically pure 11: yield 0.96 g (60%); mp 229°–231° C. (dec.); UV (pH 1) $\lambda_{max}$240 nm (sh) ($\epsilon$=0.481×10$^4$), 287 nm ($\epsilon$=1.165×10$^4$), (pH 6.9) 240 nm ($\epsilon$=0.761×10$^4$), 282 nm ($\epsilon$=0.864×10$^4$), (pH 13) 240 nm (sh) ($\epsilon$=0.474×10$^4$), 285 nm ($\epsilon$=0.919×10$^4$); $^1$H NMR $\delta$4.50 (d, 2 H, CH$_2$OH), 5.19 (t, 1 H, OH, exchanges with D$_2$O), 5.46 (s, 2 H, ArCH$_2$), 6.28 (br s, 2 H, NH$_2$, exchange with D$_2$O), 7.31–7.48 (m, 4 H, ArH), 7.80 (s, 1 H, H-8), 12.41 (br. s, 1 H, >NH, exchanges with D$_2$O); MS (EI) calcd m/z for C$_{13}$H$_{13}$N$_5$O$_2$ 271.1069, found 271.1063.

EXAMPLE 12

O$^6$-(p-Formylbenzyl)guanine

O$^6$-(p-Hydroxymethylbenzyl)guanine (3.6 mmol), sodium acetate (1.3 mmol) and pyridinium chlorochromate (5.6 mmol) were stirred in 15 mL anhydrous pyridine under argon for 20 hr at room temperature. Methanol (30 mL) was then added and the resulting mixture was stirred for 4 hours. Water (30 mL) was added and the deep brown precipitate that formed was collected by filtration. The filtrate was loaded on a 3×80 cm Sephadex LH-20 column eluted with methanol/H$_2$O (1:1) at 1 mL/min. Column eluent was continuously monitored at 280 nm and fractions (10 mL) were collected. That portion of the brown precipitate (see above) which was soluble in 60 mL of MeOH/H$_2$O (1:1) was chromatographed separately under identical conditions. The desired product together with some unreacted 11 eluted in fractions 80–110. Crystallization from methanol/$H_2O$ (1:1) with charcoal treatment of the material recovered from pooled fractions 80–110 afforded analytically pure 12: yield, 0.45 g (45%); mp>247° C. (dec.); UV (pH 1) $\lambda_{max}$ 254 nm ($\epsilon$=1.989×10$^4$), 287 nm (sh) ($\epsilon$=1.455×10$^4$), (pH 6.9) 250 nm ($\epsilon$=2.121×10$^4$), 277 nm (sh) ($\epsilon$=1.357×10$^4$), (pH 13) 256 nm ($\epsilon$=1.959×10$^4$), 279 nm (sh) ($\epsilon$=1.293×10$^4$); $^1$H NMR $\delta$5.61 (s, 2 H Ar$CH_2$), 6.29 (s, 2 H, $NH_2$, exchange with $D_2O$), 7.71 (d, 2 H, ArH), 7.86 (s, 1 H, H-8), 7.94 (d, 2 H, ArH) 10.02 (s, 1 H, CHO), 12.46 (br s, 1 H, >NH, exchanges with $D_2O$); MS (EI) calcd m/z for $C_{13}H_{11}N_5O_2$ 269.0913, found 269.0934.

EXAMPLE 13

9-Acetyl-O$^6$-benzylguanine

To 0.38 mL (4 mmol) of acetic anhydride in 0.65 mL of pyridine under argon at 0° C. was added 0.241 g (1 mmol) of O$^6$-benzylguanine. The reaction mixture was stirred at 0° C. for 30 min at which time the ice bath was removed and the reaction was allowed to proceed overnight at room temperature. At this point, a water-ice mixture (~5 ml) was added to the flask with vigorous stirring for 5 minutes. Compound 13 was collected as a white solid which was washed with $H_2O$ and dried under vacuum. Yield: 0.262 g (92.5%); mp 176°–177° C.; UV (pH 1) $\lambda_{max}$ 262 nm (sh) ($\epsilon$=0.723×10$^4$), 286 nm ($\epsilon$=0.996×10$^4$), (pH 6.9) 227 nm (sh) ($\epsilon$=1.117×10$^4$), 278 nm ($\epsilon$=1.174×10$^4$), (pH 13) (decomposes to O$^6$-benzylguanine); $^1$H NMR $\delta$2.83 (s, 3 H, $CH_3$), 5.51 (s, 2 H, Ar$CH_2$), 6.84 (s, 2 H, $NH_2$), 7.36 (m, 1 H, Ar), 7.41 (m, 2 H, Ar), 7.51 (m, 2 H, Ar), 8.31 (s, 1 H, H-8); $^{13}$C NMR $\delta$24.59 ($CH_3$), 67.09 (Ar$CH_2$), 114.47 (C-5), 128.11 (p-Ar), 128.41 (2 m-At), 128.46 (2 o-Ar), 136.32 (ipso-Ar), 136.66 (C-8), 153.32 (C-4), 160.35 (C-2), 160.42 (C-6), 168.25 (CO); MS (EI) calcd m/z for $C_{14}H_{13}N_5O_2$ 283.1069, found 283.1052.

EXAMPLE 14

O$^6$-Benzyl-7-methylguanine (14a) and O$^6$-Benzyl-9-methylguanine (14b)

To 0.24 g (1 mmol) of O$^6$-benzylguanine under argon was added 1 mL of a 1M solution of sodium ethoxide in ethanol. The solution was stirred 10 min and the ethanol was removed under vacuum. The remaining solid was dissolved in 2 mL of dry DMF. Iodomethane (1.2 mmol) was added to the stirring solution by syringe producing a slightly exothermic reaction that was allowed to proceed overnight. At this point, the reaction mixture was diluted with approximately 50 mL of H/O and the aqueous layer was washed with $CH_2Cl_1$. An oily residue was obtained by evaporation of the combined organic washes after drying with $MgSO_4$. Separation of the two isomers was achieved by dissolving the oil in a minimum volume of 10% ethanol in $CHCl_3$ and loading this onto a silica gel column (Davisil grade 633, 200–425 mesh, 60 Å, 2.5×35 cm). The 9-isomer eluted from the column with 10% EtOH in $CHCl_3$, while the 7-isomer eluted later with 15% EtOH in $CHCl_3$. The 7-isomer (14a) was obtained analytically pure upon drying at 110° C. under vacuum. The 9-isomer (14b) was further purified by precipitation from $CH_2Cl_2$ with hexane and drying at 110° C. under vacuum. O$^6$-Benzyl-7-methylguanine (14a): yield, 86 mg (33.6%); mp 175°–177° C.; UV (pH 1) $\lambda_{max}$ 240 nm (sh) ($\epsilon$=0.550×10$^4$), 290 nm ($\epsilon$=1.060×10$^4$), (pH 6.9) 241 nm (sh) ($\epsilon$=0.748×10$^4$), 291 nm ($\epsilon$=0.900×10$^4$), (pH 13) 241 nm (sh) ($\epsilon$=0.607×10$^4$), 291 nm ($\epsilon$=0.715×10$^4$); $^1$H NMR $\delta$3.83 (s, 3 H, $CH_3$), 5.50 (s, 2 H, Ar$CH_2$), 6.13 (s, 2 H, $NH_2$), 7.35 (m, 1 H, ArH), 7.41 (m, 2 H, ArH), 7.52 (m, 2 H, 2 ArH), 8.01 (s, 1 H, H-8); $^{13}$C NMR $\delta$33.43 ($CH_3$), 66.77 (Ar$CH_2$), 106.46 (C-5), 127.81 (2 o-Ar), 127.92 (p-Ar), 128.44 (2 m-Ar), 136.55 (ipso-Ar), 145.83 (C-8), 156.66 (C-6), 159.47 (C-2), 163.90 (C-4); MS (EI) calcd m/z for $C_{13}H_{13}N_5O$ 255.1120, found 255.1124. O$^6$-Benzyl-9-methylguanine (14b): yield, 75 mg (29.3%); mp 149°–151° C.; UV (pH 1) $\lambda_{max}$ 241 nm ($\epsilon$=0.740×10$^4$), 291 nm ($\epsilon$=0.907×10$^4$), (pH 6.9) 250 nm ($\epsilon$=0.753×10$^4$), 282 nm ($\epsilon$=0.951×10$^4$), (pH 13) 250 nm ($\epsilon$=0.829×10$^4$), 282 nm ($\epsilon$=1.056×10$^4$); $^1$H NMR $\delta$3.59 (s, 3 H, $CH_3$), 5.50 (s, 2 H, Ar$CH_2$), 6.45 (s, 2 H, $NH_2$), 7.35 (m, 1 H, ArH), 7.40 (m, 2 H, ArH), 7.50 (m, 2 H, ArH), 7.82 (s, 1 H, H-8); $^{13}$C NMR $\delta$29.18 ($CH_3$), 66.76 (Ar$CH_2$), 113.19 (C-5), 127.97 (p-Ar), 128.36 (2 m-Ar), 128.38 (2 o-Ar), 136.69 (ipso-Ar), 140.39 (C-8), 154.75 (C-4), 159.67 (C-2), 159.94 (C-6); MS (EI) calcd m/z for $C_{13}H_{13}N_5O$ 255.1120, found 255.1113.

EXAMPLE 15

O$^6$-Benzyl-9-(3-chloro-2-hydroxypropyl)guanine

O$^6$-Benzylguanine (2 mmol) was dissolved in 10 mL neat epichlorohydrin. The reaction mixture was heated nearly to boiling. When the solution began to turn yellow the heating was discontinued and the solution was allowed to cool to room temperature. The excess epoxide was removed under vacuum. The crude product was dissolved in a minimum of 10% ethanol in $CHCl_3$ and loaded on a 2.5×18 cm silica gel column (Davisil grade. 633, 200–425 mesh, 60 Å). The product was eluted from the column with 10% ethanol in $CHCl_3$. The recovered 15 was analytically pure after drying at 110° C. under vacuum. Yield, 240 mg (57%); mp 183°–185° C. (dec.); UV (pH 1) $\lambda_{max}$ 244 nm ($\epsilon$=0.681× 10$^4$), 292 nm ($\epsilon$=0.928×10$^4$), (pH 6.9) 250 nm ($\epsilon$=0.768× 10$^4$), 282 nm ($\epsilon$=0.943×10$^4$), (pH 13) 249 nm ($\epsilon$=0.950× 10$^4$), 282 nm ($\epsilon$=1.095×10$^4$); $^1$H NMR $\delta$3.56 (dd, 1 H, $H_a$CHCl, $^2$J=11.4 Hz, $^3$J=5.4 Hz), 3.65 (dd, 1 H, $H_b$CHCl, $^2$J=11.3 Hz, $^3$J=4.7 Hz), 4.00 (dd, 1 H, $H_a$CH<N, $^2$J=13.5 Hz, $^3$J=8.0 Hz), 4.11 (m, 1 H, CHOH), 4.16 (dd, 1 H, $H_b$CH<N, $^2$J=13.5 Hz, $^3$J=3.8 Hz), 5.50 (s, 2 H, Ar$CH_2$), 5.64 (d, 1 H, OH, $^3$J=5.4 Hz), 6.45 (s, 2 H, $NH_2$), 7.35 (t, 1 H, ArH), 7.40 (t, 2 H, ArH), 7.50 (d, 2 H, ArH), 7.79 (s, 1 H, H-8); $^{13}$C NMR $\delta$46.32 ($CH_2$Cl), 47.31 ($CH_2$N<), 66.76 (Ar$CH_2$), 68.17 (CHOH), 113.57 (C-5), 127.99 (p-Ar), 128.37 (2 m-Ar), 128.42 (2 o-Ar), 136.70 (ipso-Ar), 140.49 (C-8), 154.52 (C-4), 159.58 (C-2), 159.97 (C-6); MS (EI) calcd. m/z for $C_{15}H_{16}N_5O_2{}^{35}Cl$ 333.0992, found 333.0979; calcd. m/z for $C_{15}H_{16}N_5O_2{}^{37}Cl$ 335.0963, found 335.0939; Anal. ($C_{15}H_{16}N_5O_2Cl$) C, 53.98; H, 4.83; N, 20.98; Cl, 10.62. Found, C, 53.92; H, 4.90; N, 20.76 Cl, 11.28.

EXAMPLE 16

O$^6$-Benzyl-9-(2-hydroxy-S-isopropylaminopropyl)guanine

To a suspension of 100 mg (0.3 mmol) of 15 in 10 mL of dioxane was added 1 mL of isopropylamine. The resultant slurry was heated to reflux. The progress of the reaction was monitored by TLC (silica, 10% ethanol in chloroform). After 20 hours of reflux 1 mL more isopropylamine was added to the reaction mixture. Refluxing was continued. When the reaction was judged complete by TLC, solvent was removed under vacuum and the resulting solid was washed with 10% aqueous methanol to remove a yellow contaminant. Recrystallization of the remaining solid from 10 mL of 50% aqueous ethanol containing a few drops of isopropylamine afforded analytically pure 16: yield, 90 mg (82%); mp 206°–208° C.; UV (pH 1) $\lambda_{max}$ 244 nm ($\epsilon$=0.690×10$^4$), 292 nm ($\epsilon$=0.886×10$^4$), (pH 6.9) 250 nm ($\epsilon$=0.772×10$^4$), 282 nm ($\epsilon$=0.939×10$^4$), (pH 13) 250 nm ($\epsilon$=0.826×10$^4$), 282 nm ($\epsilon$=1.048×10$^4$); $^1$H NMR $\delta$0.96 (d, 6 H, (CH$_3$)$_2$, $^3$J=6.2 Hz), 1.58 (br s, 1 H), 2.45 (m, 2 H, CH$_2$NH), 2.65 (septet, 1 H, CHMe$_2$, $^3$J=6.2 Hz) 3.87 (m, 1 H, CHOH), 3.94 (dd, 1 H, H$_a$CH<N, $^2$J=13.8 Hz, $^3$J=7.7 Hz), 4.08 (dd, 1 H, H$_b$CH<N, $^2$J=13.7 Hz, $^3$J=3.8 Hz), 5.08 (br s, 1 H, OH), 5.48 (d, 1 H, ArH$_a$CH, $^2$J=13.3 Hz), 5.51 (d, 1 H, ArH$_b$CH, $^2$J=13.5 Hz), 6.43 (s, 2 H, NH$_2$), 7.35 (t, 1 H, ArH), 7.40 (t, 2 H, ArE), 7.50 (d, 2 H, ArH), 7.77 (s, 1 H, H-8); $^{13}$C NMR $\delta$22.88 (CH$_3$), 22.93 (CH$_3$), 47.07 (CH$_2$N<), 48.22 (CH$_2$NH), 50.54 (CHMe$_2$), 66.74 (ArCH$_2$), 68.13 (CHOH), 113.46 (C-5), 127.97 (p-Ar), 128.35 (2 m-Ar), 128.40 (2 o-Ar), 136.69 (ipso-Ar), 140.61 (C-8), 154.55 (C-4), 159.47 (C-2), 159.90 (C-6); MS (EI) calcd. m/z for C$_{18}$H$_{24}$N$_6$O$_2$ 356.1960, found 356.1970.

EXAMPLE 17

O$^6$-Benzyl-9-(3-t-butylamino-2-hydroxypropyl)guanine

To a 5-mL microflex flask fitted with a magnetic stirrer and sealed pressure value was added 80 mg (0.24 mmol) of 15, 1 mL of dioxane, 1 mL of t-butylamine and a few mg of potassium carbonate. The resulting suspension was heated in a 90° C. oil bath for 22 hr. Solvent was removed under vacuum, and the resulting solid was washed with 10% aqueous methanol to remove a yellow contaminant. O$^6$-Benzyl-9-(3-t-butylamino-2-hydroxypropyl)guanine (17) was purified by crystallization from 10 mL of 50% aqueous ethanol containing a few drops of t-butylamine. Yield, 84 mg (95%); mp 169°–170.5° C.; UV (pH 1) $\lambda_{max}$ 243 nm ($\epsilon$=0.686×10$^4$), 292 nm ($\epsilon$=0.917×10$^4$), (pH 6.9) 250 nm ($\epsilon$=0.782×10$^4$), 282 nm ($\epsilon$=0.952×10$^4$), (pH 13) 250 nm ($\epsilon$=0.766×10$^4$), 282 nm ($\epsilon$=0.974×10$^4$); $^1$H NMR $\delta$1.00 (s, 9 H, CH$_3$), 2.44 (m, 2 H, CH$_2$N-t-butyl), 3.84 (m, 1 H, CHOH), 3.95 (dd, 1 H, H$_a$CH<N, $^2$J=14.1 Hz, $^3$J=7.7 Hz), 4.09 (dd, 1 H, H$_b$CH<N, $^2$J=13.9 Hz, $^3$J=4.1 Hz), 5.06 (m, 1 H, OH), 5.48 (d, 1H, ArH$_a$CH, $^2$J=13.7 Hz), 5.50 (d, 1H, ArH$_b$CH, $^2$J=13.4 Hz), 6.43 (s, 2 H, NH$_2$), 7.35 (t, 1 H, ArH), 7.40 (t, 2 H, ArH), 7.50 (d, 2 H, ArH), 7.77 (s, 1 H, H-8); $^{13}$C NMR $\delta$28.70. (3 CH$_3$), 45.70 (CH$_2$NH), 47.03 (CH$_2$N<), 49.66 (CMe$_3$), 66.74 (ArCH$_2$), 68.54 (CHOH), 113.45 (C-5), 127.96 (p-Ar), 128.34 (2 m-Ar), 128.39 (2 o-Ar), 136.68 (ipso-Ar), 140.63 (C-8), 154.55 (C-4), 159.45 (C-2), 159.90 (C-6); MS (EI) calcd. m/z for C$_{19}$H$_{26}$N$_6$O$_2$ 370.2117, found 370.2122.

EXAMPLE 18

O$^6$-Benzyl-9-(2-hydroxy-3-isopropoxypropyl)guanine

O$^6$-Benzylguanine (1.25 mmol) and glycidyl isopropyl ether (3 mL, 24 mmol) were heated under argon on a 110° C. oil bath 2 hr. The excess glycidyl isopropyl ether was evaporated under vacuum. The resulting brown solid was dried under vacuum overnight and was purified by silica-gel column chromatography (Davisil grade 633, 200–425 mesh, 60 Å) using 7% EtOH in CHCl$_3$ as eluent to give a pale yellow solid. It was further purified by dissolving in dichloromethane (3 mL) and precipitating with hexane (6 mL). The white precipitate was collected by filtration to provide analytically pure 18: yield, 90 mg (20%); mp 193°–194° C.; UV (MeOH/H$_2$O, 1:1) $\lambda_{max}$ 251 nm ($\epsilon$=0.787×10$^4$), 283 ($\epsilon$=0.940×10$^4$); $^1$H NMR $\delta$1.08 (d, 6 H, CH$_3$), 3.25–3.40 (m, 2 H, OCH$_2$), 3.52 (septet, 1 H, CH(CH$_3$)$_2$), 3.86–4.02 (m, 2 H, CHOH+NCH$_a$H), 4.05–4.22 (m, 1 H, NCH$_b$H), 5.18 (br d, 1 H, OH, exchanges with D$_2$O), 5.50 (s, 2 H, ArCH$_2$), 6.41 (br s, 2 H, NH$_2$, exchange with D$_2$O), 7.32–7.54 (m, 5 H, ArH), 7.77 (s, 1 H, H-8); MS (EI) Calcd. m/z for C$_{18}$H$_{23}$N$_5$O$_3$ 357.1800, found 357.1797.

EXAMPLE 19

17$\beta$-Chloroacetoxy-4-androsten-3-one

Testosterone (5 mmol) was dissolved in anhydrous methylene chloride (7.0 mL) and triethylamine (5 mmol) under argon. The solution was stirred for 30 minutes in an ice-bath. Chloroacetyl chloride (10 mmol) dissolved in anhydrous methylene chloride (3 mL) was added at 0° C. and stirring was continued for 30 minutes. The reaction was then allowed to warm to room temperature and was stirred overnight. The solution was washed with 0.05N hydrochloric aqueous solution (2×10 mL) and water (2×10 mL) and dried over sodium sulfate. It was concentrated under reduced pressure to give a brown solid. It was purified by silica gel column chromatography (Davisil grade 633, 200–425 mesh, 60 Å) using chloroform/petroleum ether (2:1) as an eluent to give a white solid. Yield, 1.23 g (67%); mp 125°–126° C. (124°–125° C., Molen et al., *Steroids*, 6, 195–214 (1965)); UV (MeOH/H$_2$O, 1:1) $\lambda_{max}$ 246 nm ($\epsilon$=1.521×10$^4$); $^1$H NMR $\delta$0.81 (s, 3 H, CH$_3$-19), 1.15 (s, 3 H, CH$_3$-18), 0.82–2.50 (m, 19 H), 4.38 (d, 2 H, CH$_2$Cl), 4.63 (t, 1 H, H-17), 5.63 (s, 1 H, H-4); MS (EI) Calcd. m/z for C$_{21}$H$_{29}$O$_3$$^{35}$Cl 364.1805, found, 364.1804. Calcd. m/z for C$_{21}$H$_{29}$O$_3$$^{37}$Cl 366.1776, found, 366.1776.

EXAMPLE 20

O$^6$-Benzyl-9-(4-androsten-3-one-17$\beta$-oxycarbonylmethyl) guanine

O$^6$-Benzylguanine (3.0 mmol) was dissolved in 3 mL of a 1M solution of sodium ethoxide in ethanol under argon with stirring for 30 min. Ethanol was removed under reduced pressure and the resulting solid was redissolved in anhydrous DMF (4 mL). 17$\beta$-Chloroacetoxy-4-androsten-3-one (3.0 mmol) dissolved in anhydrous DMF (6 mL) was added to the solution with stirring for 1 hr at room temperature. The solvent was removed under reduced pressure to produce a brown hard foam. The product was purified by silica gel column chromatography (Davisil grade 633, 200–425 mesh, 60 Å) using 5% ethanol in CHCl$_3$ as eluent to give 20 as a pale yellow hard foam. Yield, 0.946 g (55%); mp 125°–127° C.; UV (MeOH/H$_2$O, 1:1) $\lambda_{max}$ 247 nm ($\epsilon$=2.495×10$^4$), 282 ($\epsilon$=0.959×10$^4$); $^1$H NMR $\delta$0.61 (s, 3 H, CHS-19'), 1.14 (s, 3 H, CH$_3$-18'), 0.8–2.40 (m, 19 H), 4.56 (t, 1 H, H-17'), 4.93 (d, 2 H, CH$_2$N), 5.51 (s, 2 H, ArCH$_2$), 5.62 (s, 1 H, H-4'), 6.50 (br s, 2 H, NH$_2$, exchange with D$_2$O), 7.30–7.55 (m, 5 H, ArH), 7.85 (s, 1 H, H-8); MS (Positive ion fast atom bombardment) Calcd. m/z for C$_{33}$H$_{39}$N$_5$O$_4$ 569.3001, found, 569.3006.

EXAMPLE 21

17$\beta$-Chloroacetoxy-5$\alpha$-androstan-3-one

Dihydrotestosterone (2.6 mmol) was dissolved in anhydrous methylene chloride (3 mL) and triethylamine (2.6 mmol) under argon. The solution was stirred at 0° C. for 30 minutes at which time chloroacetyl chloride (3.75 mmol) dissolved in anhydrous methylene chloride (2 mL) was added. The resulting mixture was stirred for an additional 30 min at 0° C. and at room temperature for 4 hr. The solution was diluted with CH$_2$Cl$_2$ (30 mL) and was washed with aqueous 0.05N hydrochloric acid (2×30 mL) and water (2×30 mL). The organic layer was dried over sodium sulfate and evaporated under vacuum to give crude product as a white solid. The product was purified by silica gel column chromatography (Davisil grade 633, 200–425 mesh, 60 Å) using CHCl$_3$ as eluent. Yield, 0.38 g (41%); mp 135°–136° C. (lit. Ferguson et al., *J. Chem. Soc., Perkin II*, 3, 267–272

(1978)), 138° C.); $^1$H NMR δ0.78 (s, 3 H, CH$_3$-19), 0.98 (s, 3 H, CH$_3$-18), 0.78–2.49 (m, 22 H), 4.37 (d, 2 H, CH$_2$Cl), 4.62 (t, 1 H, H-17); MS (EI) calcd m/z for C$_{21}$H$_{31}$O$_3$$^{35}$Cl 366.1961, found, 366.1932; calcd. m/z for C$_{21}$H$_{31}$O$_3$$^{37}$Cl 368.1932, found, 368.1911.

EXAMPLE 22

O$^6$-Benzyl-9-(5α-androstan-3-one-17β-oxycarbonylmethyl) guanine

O$^6$-Benzylguanine (1.0 mmol) was dissolved in 1 mL of a 1M solution of sodium ethoxide in ethanol with stirring for 30 min at room temperature. The ethanol was evaporated under reduced pressure. The solid residue was dissolved in anhydrous DMF (2 mL), and 17β-chloroacetoxy-5α-androstan-3-one (1.0 mmol) dissolved in anhydrous DMF (4 mL) was added. The solution was stirred for 2 hr at room temperature. The solvent was evaporated under the vacuum to give a brown hard foam. The product was purified by silica gel column chromatography (Davisil grade 633, 200–425 mesh, 60 Å) using 10% EtOH in CHCl$_3$ as eluent. Yield, 0.36 g (62%); mp 168°–170° C.; UV (MeOH/H$_2$O, 1:1) λ$_{max}$ 247 nm (0.843×10$^4$), 284 (0.997×10$^4$); $^1$H NMR δ0.57 (s, 3 H, CH$_3$-19'), 0.96 (s, 3 H, CH$_3$-18'), 0.57–2.47 (m, 22 H), 4.53 (t, 1 H, H-17'), 4.92 (d, 2H, CH$_2$N), 5.51 (s, 2 H, ArCH$_2$), 6.49 (br s, 2 H, NH$_2$, exchange with D$_2$O), 7.30–7.55 (m, 5 H, ArH), 7.85 (s, 1 H, H-8); MS (Positive ion fast atom bombardment) Calcd. m/z for C$_{33}$H$_{41}$N$_5$O$_4$, 571.3158, found, 571.3192.

EXAMPLE 23

The dose of various O$^6$-substituted guanine derivatives required to inhibit 50% of the AGT activity of cell-free extracts from human colon tumor cells HT29 and intact HT29 cells is shown in Tables 2 and 3.

TABLE 2

Depletion of alkyltransferase in HT29 cells and in HT29 cell-free extract[a]

| Example No. | Compound | ED$_{50}$ (μM) In cell-free extract | In cells |
|---|---|---|---|
| | O$^6$-benzylguanine | 0.2 | 0.05 |
| | O$^6$-(p-fluorobenzyl)guanine | 0.2 | 0.05 |
| | O$^6$-(p-chlorobenzyl)guanine | 0.2 | 0.08 |
| | O$^6$-(p-methylbenzyl)guanine | 0.2 | 0.08 |
| | O$^6$-benzyl-2'-deoxyguanosine | 2 | 0.5 |
| | O$^6$-(p-methylbenzyl)guanosine | 9 | 3 |
| | O$^6$-(p-chlorobenzyl)guanosine | 10 | 5 |
| | O$^6$-benzylguanosine | 11 | 2 |
| | O$^6$-allylguanine | 20 | 4 |
| 3b | 2-amino-6-benzyloxy-9-carboethoxymethylpurine | 30 | 3 |
| | 2-amino-6-benzyloxy-9-carboxymethylpurine, sodium salt | 157 | Inactive[b] |
| | 2 amino-6-benzyloxy-7-carboxymethylpurine, sodium salt | Inactive[b] | Inactive[b] |
| 3a | 2-amino-6-benzyloxy-7-carboethoxymethylpurine | Inactive[b] | Not tested |
| | O$^6$-methylguanine | 350 | 120 |

[a]The numbers indicate the effective dose required to produce 50% inactivation in cell free extracts upon incubation for 30 min or in cells upon incubation for 4 h.
[b]Compounds are described as inactive when there was no significant effect at the maximal concentration which could be used due to the compound's solubility.

TABLE 3

AGT-Inactivating Activity of O$^6$-Benzylguanine Derivatives

| Example No. | Compound | ED$_{50}$ (μM)[a] In HT29 cell-free extract | In HT29 cells |
|---|---|---|---|
| 9 | O$^6$-(p-bromobenzyl)guanine | 0.3 | 0.09 |
| 11 | O$^6$-(p-hydroxymethylbenzyl)guanine | 0.3 | 0.09 |
| 10c | O$^6$-(p-phenylbenzyl)guanine | 0.3 | 0.1 |
| 13 | 9-acetyl-O$^6$-benzylguanine | 0.4[b] | 0.1[b] |
| 10a | O$^6$-(p-isopropylbenzyl)guanine | 0.5 | 0.6 |
| 12 | O$^6$-(p-formylbenzyl)guanine | 0.5 | 0.7 |
| 10d | O$^6$-(3,5-dimethylbenzyl)guanine | 1.0 | 0.4 |
| 14b | O$^6$-benzyl-9 methylguanine | 2.6 | 0.4 |
| 7 | O$^6$-benzyl-9-(pivaloyloxymethyl)guanine | 3.1 | 0.3[c] |
| 10b | O$^6$-(p-n-butylbenzyl)guanine | 4.0 | 1.0 |
| 22 | O$^6$-benzyl-9-(5α-androstan-3-one-17β-oxycarbonylmethyl)guanine | 4.0 | 0.5 |
| 20 | O$^6$-benzyl-9-(4-androsten-3-one-17β-oxycarbonylmethyl)guanine | 5.0 | 0.5 |
| 18 | O$^6$-benzyl-9-(2-hydroxy-3-isopropoxypropyl)guanine | 7.0 | 0.8 |
| 15 | O$^6$-benzyl-9-(3-chloro-2-hydroxypropyl)guanine | 18 | 2 |
| | N$^2$-acetyl -O$^6$-benzylguanine | 24 | 2 |
| 14a | O$^6$-benzyl-7-methylguanine | 52 | 17 |

TABLE 3-continued

AGT-Inactivating Activity of O⁶-Benzylguanine Derivatives

| Example No. | Compound | ED$_{50}$ ($\mu$M)[a] | |
|---|---|---|---|
| | | In HT29 cell-free extract | In HT29 cells |
| | O⁶-(2-pyridylmethyl)guanine | 58 | 16 |
| 16 | O⁶-benzyl-9-(2-hydroxy-3-isopropylaminopropyl)guanine | 106 | 23 |
| 17 | O⁶-benzyl-9-(3-t-butylamino-2-hydroxypropyl) guanine | 106 | 26 |

[a]The effective dose required to produce 50% inactivation in cell-free extracts upon incubation for 30 min or in cells upon incubation for 4 hr. The corresponding values for O⁶-benzylguanine are 0.2 and 0.05, respectively (Moschel et al., J. Med. Chem., 35, 4486–4491 (1992)).
[b]Converted to O⁶-benzylguanine by hydrolysis in vitro and in cultures.
[c]Converted to O⁶-benzylguanine by esterases in cell cultures. The compound is stable in vitro.

It is expected that any agent which effectively depletes tumor cells of AGT activity will produce an enhancement in the cytotoxic response to chemotherapeutic alkylating agents such as chloroethylating nitrosoureas or other alkylating antineoplastic agents. This has been shown to be true with the weak AGT depleters O⁶-methylguanine (Dolan et al., Cancer Res., 46, pp. 4500–4504 (1986)) and the more potent benzylated derivatives O⁶-benzylguanine, O⁶-(p-chlorobenzyl)- and O⁶-(p-methylbenzyl)guanine (Dolan et al. Proc. Natl. Acad. Sci. USA, 87, 5368–5372 (1990); Dolan et al. Cancer Res., 51, pp. 3367–3372 (1991); Mitchell et al., Cancer Res., 52, pp. 1171–1175 (1992)).

The 9-substituted analogs described herein would also be expected to be effective in this capacity and it is likely that varying the structure of the substituent group attached to the 9-position of these analogs can be used to alter the biodistribution of these compounds by changing their solubility, by causing them to be recognized by receptors specific to certain tumor types, and/or by altering their cellular transport mechanisms. For example, the 2'-deoxyribonucleoside and ribonucleoside analogs described above are far more water soluble than the corresponding benzylated guanine bases and these nucleosides may be taken up in certain cell types by nucleoside transport systems rather than enter by simple passive diffusion. Additionally, a glucose or amino acid moiety attached to position 9 of an O⁶-benzylated or O⁶-allylguanine derivative may enhance transport into tumors with glucose or amino acid transporters. For example, Streptozotocin, a 2-deoxy-D-glucose derivative of methylnitrosourea, has been shown to be selectively destructive to pancreatic beta cells and this agent is used clinically against islet cell carcinoma of the pancreas (Broder and Carter, Ann. Intern. Med., 79, pp. 108–118 (1973)). Also, a glucose derivative of O⁶-benzylguanine such as the non-acetylated analog of 2-amino-6-benzyloxy-9-{N-[2-deoxy-2-(1,3,4, 6-tetra-O-acetyl)-D-glucopyranosyl]carbamoylmethyl}purine (Example 8) may be useful in selectively depleting AGT in pancreatic tumors. Linkage of an O⁶-benzylated guanine derivative to the hydroxyl group at position 17 of a steroid such as estradiol may permit specific accumulation of the AGT depleter in estradiol receptor containing tumor cells such as estradiol receptor-positive mammary carcinomas. Nitrosourea linked estradiols have been quite effective in initial studies against these tumor types (Brix et al., J. Cancer Res. Clin. Oncol., 116, pp. 538–549, (1990); Eisenbrand et al., Anticancer Drug Design, 2, pp. 351–359 (1988); Zeller et al., Arneimetterforschung, 39, 1577–1579 (1989)).

Thiouracil, an aromatic heterocycle, accumulates readily in active melanin producing cells such as melanoma cells (Fairchild et al., Int. J. Radiat. Oncol. Biol. Phys., 17, pp. 337–343 (1989); Wilson, Pigment Cell Research, 2, pp. 297–303 (1989)). Therefore, linkage of an O⁶-benzylated guanine or an O⁶-allylguanine derivative to thiouracil by reaction with a reactive thiouracil derivative such as a 5-halomethyl-2-thiouracil might provide an agent that could selectively deplete AGT in malignant melanoma cells.

The ability of O⁶-benzylguanine to deplete AGT activity in brain tumor xenografts and thereby increase the sensitivity of these tumors to 1,3-bis(2-chloroethyl)-1-nitrosourea (BCNU) was studied. In toxicity studies, pretreatment of athymic mice with O⁶-benzylguanine increased the toxicity of BCNU significantly. After i.p. injection of O⁶-benzylguanine into athymic mice carrying subcutaneous (sc) D341MED, a human medulloblastoma xenograft with a high AGT activity, the AGT activity of the tumors dropped from its pretreatment level to undetectable within 1 hour and remained depleted until 36 hours. In sc xenografts of D341MED, treatment with O⁶-benzylguanine followed 1 hour later by BCNU produced a significantly greater effect than was seen with either the same or a higher dose of BCNU alone. A lower pretreatment dose of O⁶-benzylguanine produced a significantly lesser therapeutic effect. Delaying the administration of BCNU until 36 hours after O⁶-benzylguanine resulted in a greatly reduced effect that was not significantly different than that produced by control or BCNU alone. In athymic mice with intracranial (ic) xenografts of D341MED, pretreatment with O⁶-benzylguanine followed 1 hour later by BCNU produced a significantly increased survival as compared to that of control, BCNU alone, O⁶-benzylguanine alone and O⁶-benzylguanine followed 36 hours later by BCNU. In experiments with sc xenografts of D245MG, a human glioma xenograft with undetectable AGT activity by our assay, pretreatment with O⁶-benzylguanine 1 hour prior to BCNU produced a significantly greater effect than was seen with BCNU treatment alone. Again, higher doses of O⁶-benzylguanine produced a greater therapeutic effect. None of the combination regimens, however, were as effective as an equitoxic dose of BCNU alone. These studies suggest that O⁶-benzylguanine may be a useful adjuvant to nitrosourea therapy in human malignancies that exhibit a range of AGT activities, and that dose and timing are important variables in achieving therapeutic success. Additionally, these data suggest that therapeutic potentiation of BCNU by O⁶-benzylguanine can be achieved in intracranial tumors, and this approach may therefore be useful in the chemotherapy of human neoplasms of the brain and central nervous system. (Selker et al., Cancer Chemother. Pharmacol., 32, pp. 471–476 (1993); Friedman et al., JNCI, 84, pp. 1926–1931 (1992)).

The anti-tumor effect of BCNU in the treatment of prostate cancer was enhanced by pretreatment with $O^6$-benzylguanine When rats bearing prostate tumors were treated with $O^6$-benzylguanine one hour prior to the treatment with BCNU, there was a regression in tumor growth which was not observed in animals treated with an equal dose of BCNU alone. (Dolan et al., *Cancer Chemother. Pharmacol.*, 32, pp. 221–225 (1993)).

These descriptions are provided as examples of how an $O^6$-substituted guanine derivative as represented by formulas 1–4 can lead to depletion of AGT in tumors and produce enhanced killing of these cells by chloroethylating nitrosoureas or other alkylating anti-neoplastic agents. As the examples herein illustrate, the range of useful guanine derivatives is indeed broad and the examples are in no way limiting of the invention.

The $O^6$-substituted guanine derivatives disclosed in the present invention may be made into pharmaceutical compositions by accommodation with appropriate pharmaceutically acceptable excipients or carriers or diluents, and may be formulated into preparations in solid, semi-solid, liquid or gaseous forms such as tablets, capsules, powders, granules, ointments, solutions, suppositories, injections, inhalants, and aerosols in the usual ways for their respective route of administration. The following methods and excipients are merely exemplary and are in no way limiting.

In pharmaceutical dosage forms, the $O^6$-benzylguanine derivatives or $O^6$-allylguanine derivatives in the present invention may be used in the form of their pharmaceutically acceptable salts, and also may be used alone or in appropriate association, as well as in combination with other pharmaceutically active compounds.

In the case of oral preparations, the $O^6$-substituted guanine derivatives of the present invention may be used alone or in combination with appropriate additives to make tablets, powders, granules, or capsules, e.g. with conventional additives such as lactose, mannitol, corn starch or potato starch; with binders such as crystalline cellulose, cellulose derivatives, acacia, corn starch or gelatins, with sodium carboxymethylcellulose; with lubricants such as talc or magnesium stearate; and if desired, with diluents, buffering agents, moistening agents, preservatives and flavoring agents.

Furthermore, the $O^6$-substituted guanine derivatives employed in the present invention may be made into suppositories by mixing with a variety of bases such as emulsifying bases or water-soluble bases.

The $O^6$-substituted guanine derivatives disclosed in the present invention also may be formulated into preparations for injections by dissolving, suspending or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In the cases of inhalations or aerosol preparations, the $O^6$-substituted guanine derivatives employed in the present invention in the form of a liquid or minute powder may be filled up in an aerosol container with gas or liquid spraying agents, and if desired, together with conventional adjuvants such as humidifying agents. They may also be formulated as pharmaceuticals for non-pressured preparations such as a nebulizer or an atomizer.

The amount of $O^6$-substituted guanine derivative employed in the present invention to be used varies according to the degree of the effective amount required for treating tumor cells. A suitable dosage is that which will result in a concentration of $O^6$-substituted guanine derivative in the tumor cells to be treated which results in the depletion of AGT activity, e.g. about 1–2000 mg/kg prior to chemotherapy and preferably 10–800 mg/kg prior to chemotherapy.

Unit dosage forms for oral administration such as syrups, elixiers, and suspensions wherein each dosage unit (e.g., teaspoonful or tablespoonful) contains a predetermined amount of $O^6$-benzylguanine derivative employed in the present invention can be combined with a pharmaceutically acceptable carrier, such as Steril Water for Injection, USP, or normal saline.

The $O^6$-substituted guanine derivatives employed in the present invention also can be administered rectally via a suppository. The supposity can include vehicles such as cocoa butter, carbowaxes and polyethylene glycols, which melt at body temperature, yet are solidified at room temperature.

$O^6$-Substituted guanine derivatives employed in the present invention may be administered transdermally in an appropriate vehicle or salt or converted to a salt. Adsorption may be aided by the use of an electric current or field.

The $O^6$-substituted guanine derivatives employed in the present invention also may be administered with an appropriate vehicle for buccal or sublingual administration, if so desired.

The $O^6$-substituted guanine derivatives employed in the present invention also can be utilized in aerosol formulations to be administered via inhalation. The $O^6$-substituted derivatives can be formulated into pressurized acceptable propellants such as dichlorodifluoromethane, propane, nitrogen and the like.

The term "unit dosage form" as used herein generally refers to physically discrete units suitable as unitary dosages for human and animal subjects, each unit containing a predetermined quantity of at least one $O^6$-benzyl- or allyl-guanine derivative calculated in an amount sufficient to produce the desired effect in association with a pharmaceutically acceptable diluent, carrier, excipient or vehicle. The specifications for the novel unit dosage forms of the present invention depend on the particular compound employed and the effect to be achieved, and the pharmacodynamics associated with each compound in the host.

The pharmaceutically acceptable excipients, for example, vehicles, adjuvants, carriers or diluents are readily available to the public.

Any necessary adjustments in dose can be readily made to meet the chemotherapeutic treatment requirements and adjusted accordingly by the skilled practitioner.

Alkylating agents, such as chloroethylating agents, may be administered using conventional techniques such as those described in Wasserman et al., *Cancer*, 36, pp. 1258–1268 (1975); and *Physicians' Desk Reference*, 44th ed., Edward R. Barnhart publisher (1990). For example, 1,3-bis(2-chloroethyl)-1-nitrosourea (carmustine or BCNU, Bristol-Myers, Evansville, Ind.) may be administered intravenously at a dosage of from about 150 to 200 mg/m² every six weeks. Another alkylating agent, 1-(2-chloroethyl)-3-cyclohexyl-1-nitrosourea (lomustine or CCNU, Bristol-Myers), may be administered orally at a dosage of about 130 mg/m² every six weeks. Other alkylating agents may be administered in appropriate dosages via appropriate routes of administration known to skilled medical practitioners.

The invention being thus described, it will be obvious that the same may be varied in many ways. Such variations are

What is claimed:

1. A compound of the formula:

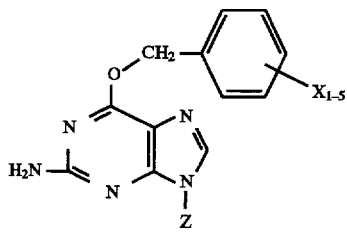

wherein each of $X_1$–$X_5$ is selected from the group consisting of hydrogen, halogen, hydroxy, aryl, a $C_1$–$C_8$ alkyl substituted aryl, nitro, a polycyclic aromatic alkyl containing 2–4 aromatic rings wherein the alkyl is a $C_1$–$C_6$, a $C_3$–$C_8$ cycloalkyl, a $C_2$–$C_6$ alkenyl, a $C_2$–$C_6$ alkynyl, a $C_1$–$C_6$ hydroxyalkyl, a $C_1$–$C_8$ alkoxy, a $C_2$–$C_8$ alkoxyalkyl, aryloxy, acyloxy, an acyloxyalkyl wherein the alkyl is $C_1$–$C_6$, amino, a monoalkylamino wherein the alkyl is $C_1$–$C_6$, a dialkylamino wherein the alkyl is $C_1$–$C_6$, acylamino, ureido, thioureido, carboxy, a carboxyalkyl wherein the alkyl is $C_1$–$C_6$, cyano, a cyanoalkyl wherein the alkyl is $C_1$–$C_6$, C-formyl, C-acyl, a dialkoxymethyl wherein the alkoxy is $C_1$–$C_6$, an aminoalkyl wherein the alkyl is $C_1$–$C_6$, and $SO_nR_1$ wherein n=0, 1, 2 or 3, $R_1$ is H, a $C_1$–$C_6$ alkyl or aryl; and wherein Z is selected from the group consisting of aryl, a substituted aryl wherein the aryl substituents are selected from the group consisting of $C_1$–$C_6$ alkyls, nitro and halo, a polycyclic aromatic alkyl containing 2–4 aromatic rings, $C_2$–$C_6$ alkenyl, $C_6$ alkynyl, halomethyl, $C_1$–$C_3$ hydroxyalkyl, $C_1$–$C_6$ halohydroxy alkyl, acyloxy, pivaloyloxymethyl, carboxy, the acid and salt forms of carboxyalkyl wherein the alkyl is $C_1$–$C_6$, $C_1$–$C_8$ alkoxy, carbonyl, carbamoyl, a carbamoylalkyl wherein the alkyl is $C_1$–$C_6$, hydrazinocarbonyl, chlorocarbonyl, cyano, $C_2$–$C_9$ cyanoalkyl, C-formyl, a dialkoxymethyl wherein the alkoxy is $C_1$–$C_6$, C-acyl, an alkoxy hydroxyalkyl wherein the alkyl and the alkoxy are $C_1$–$C_4$, carboxymethyl thio, a carboalkoxy alkyl wherein the alkoxy and alkyl are $C_1$–$C_6$, a monoalkylamino hydroxyalkyl wherein the alkyl is $C_1$–$C_6$, a dialkylamino hydroxyalkyl wherein the alkyl is $C_1$–$C_6$, amino hydroxyalkyl wherein the alkyl is $C_1$–$C_6$, a peptide, a monosaccharide selected from the group consisting of aldotetroses and aldohexoses, a polysaccharide selected from the group consisting of sucrose, lactose, maltose and cellobiose, a nucleic acid segment, asteroid selected from the group consisting of testosterone, nortestosterone, and dihydrotestosterone, and $SO_nR_1$ wherein n is 0, 1, 2, or 3 and $R_1$ is H, $C_1$–$C_6$ alkyl or aryl.

2. A compound of the formula:

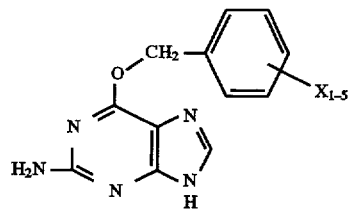

wherein each of $X_1$–$X_5$ is selected from the group consisting of $C_2$–$C_8$ alkoxyalkyl, aryloxy, acyloxy, an acyloxyalkyl wherein the alkyl is $C_1$–$C_3$, hydrazino, hydroxyamino, acylamino, or nitro at o and m-positions, m-methyl, $C_1$–$C_3$ hydroxy alkyl, $C_2$–$C_6$ alkyl, C-formyl, and aryl.

3. A compound of the formula:

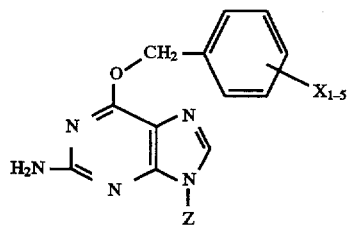

wherein Z is 1-β-D-ribofuranoside or 1-β-D-2-deoxy ribofuranoside and wherein $X_1$–$X_5$ is selected from the group consisting of $C_2$–$C_8$ alkoxyalkyl, aryloxy, acyloxy, and an acyloxyalkyl wherein the alkyl is $C_1$–$C_6$, acylamino.

4. A compound of the formula:

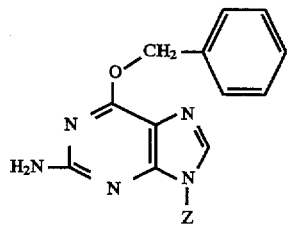

wherein Z is carboethoxymethyl, a conjugate acid form of a carboxymethyl group, a carboxylate anion of a carboxymethyl group as sodium salt, carbamoyl methyl, 2-hydroxybutyl, cyanomethyl, pivaloyloxymethyl, 3-amino-2-hydroxypropyl, 3-alkylamino-2-hydroxypropyl, and 3-dialkylamino-2-hydroxypropyl.

5. A compound of the formula:

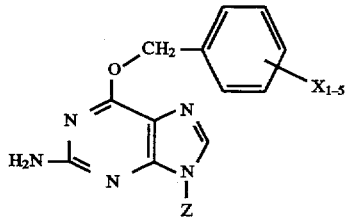

wherein each of $X_1$–$X_5$ is selected from the group consisting of halogen, hydroxy, aryl, a $C_1$–$C_8$ alkyl substituted aryl, nitro, a polycyclic aromatic alkyl containing 2–4 aromatic rings wherein the alkyl is a $C_1$–$C_6$, a $C_3$–$C_8$ cycloalkyl, a $C_2$–$C_6$ alkenyl, a $C_2$–$C_6$ alkynyl, a $C_1$–$C_6$ hydroxyalkyl, a $C_1$–$C_8$ alkoxy, a $C_2$–$C_8$ alkoxyalkyl, aryloxy, acyloxy, an acyloxyalkyl wherein the alkyl is $C_1$–$C_6$, amino, a monoalkylamino wherein the alkyl is $C_1$–$C_6$, a dialkylamino wherein the alkyl is $C_1$–$C_6$, acylamino, ureido, thioureido, carboxy, a carboxyalkyl wherein the alkyl is $C_1$–$C_6$, cyano, a cyanoalkyl wherein the alkyl is $C_1$–$C_6$, C-formyl, C-acyl, a dialkoxymethyl wherein the alkoxy is $C_1$–$C_6$, an aminoalkyl wherein the alkyl is $C_1$–$C_6$, and $SO_nR_1$ wherein n=0, 1, 2 or 3, $R_1$ is H, a $C_1$–$C_6$ alkyl or aryl; and wherein Z is selected from the group consisting of methyl, aryl, a substituted aryl wherein the aryl substituents are selected from the group consisting of $C_1$–$C_6$ alkyls, nitro and halo, a polycyclic aromatic alkyl containing 2–4 aromatic rings, $C_1$–$C_6$ alkyl, $C_2$–$C_6$ alkenyl, $C_6$ alkynyl, halomethyl, $C_3$–$C_6$ haloalkyl, $C_1$–$C_3$ hydroxyalkyl, $C_1$–$C_6$ halohydroxy alkyl, acyloxy, an acyloxyalkyl wherein the alkyl is $C_1$–$C_3$, carboxy, the acid and salt forms of carboxyalkyl wherein the alkyl is $C_1$–$C_6$, $C_1$–$C_8$ alkoxy, carbonyl, carbamoyl, a carbamoylalkyl wherein the alkyl is $C_1$–$C_6$, hydrazinocarbonyl, chlorocarbonyl, cyano, $C_2$–$C_9$ cyanoalkyl, C-formyl, a dialkoxymethyl wherein the alkoxy is $C_1$–$C_6$, C-acyl, an alkoxy hydroxyalkyl wherein the alkyl and the alkoxy are $C_1$–$C_4$, carboxymethyl thio, a carboalkoxy alkyl wherein the alkoxy and alkyl are $C_1$–$C_6$, a monoalkylamino hydroxyalkyl wherein the alkyl is $C_1$–$C_6$, a dialkylamino hydroxyalkyl wherein the alkyl is $C_1$–$C_6$, amino hydroxyalkyl wherein the alkyl is $C_1$–$C_6$, a peptide, a monosaccharide selected from the group consisting of aldotetroses and aldohexoses, a polysaccharide selected from the group consisting of sucrose, lactose, maltose and cellobiose, a nucleic acid segment, asteroid selected from the group consisting of testosterone, nortestosterone, and dihydrotestosterone, and $SO_nR_1$ wherein n is 0, 1, 2, or 3 and $R_1$ is H, $C_1$–$C_6$ alkyl or aryl.

6. A pharmaceutical composition comprising a compound of claim 5 and a pharmaceutically acceptable excipient.

7. The pharmaceutical composition of claim 6, further comprising an anti-neoplastic alkylating agent.

8. The compound of claim 1, wherein said compound is selected from the group consisting of $O^6$-benzyl-9-acetylguanine, $O^6$-benzyl-9-(pivaloyloxymethyl) guanine, $O^6$-benzyl-9-(3-chloro-2-hydroxypropyl) guanine, $O^6$-benzyl-9-(2-hydroxy-3-isopropylaminopropyl) guanine, $O^6$-benzyl-9-(3-t-butylamino-2-hydroxypropyl) guanine, $O^6$-benzyl-9-(2-hydroxy-3-isopropoxypropyl) guanine, $O^6$-benzyl-9-(4-androstan-3-one-17β-oxycarbonylmethyl) guanine and $O^6$-benzyl-9-(5α-androstan-3-one-17β-oxycarbonylmethyl)guanine.

9. The compound of claim 2 wherein said compound is selected from the group consisting of $O^6$-(p-isopropylbenzyl) guanine, $O^6$-(p-n-butylbenzyl)guanine, $O^6$-(p-phenylbenzyl) guanine, $O^6$-(3,5-dimethylbenzyl) guanine, $O^6$-(p-hydroxymethylbenzyl)guanine, and $O^6$-(p-formylbenzyl) guanine.

10. The compound of claim 2 wherein said compound $O^6$-(p-bromobenzyl)guanine.

11. A pharmaceutical composition comprising a compound of the formula:

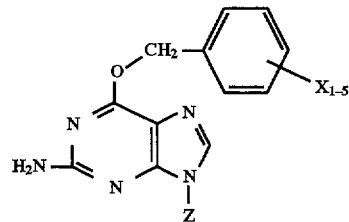

wherein each of $X_1$–$X_5$ is selected from the group consisting of hydrogen, halogen, hydroxy, aryl, a $C_1$–$C_8$ alkyl substituted aryl, nitro, a polycyclic aromatic alkyl containing 2–4 aromatic rings wherein the alkyl is a $C_1$–$C_6$, a $C_3$–$C_8$ cycloalkyl, a $C_2$–$C_6$ alkenyl, a $C_2$–$C_6$ alkynyl, a $C_1$–$C_6$ hydroxyalkyl, a $C_1$–$C_8$ alkoxy, a $C_2$–$C_8$ alkoxyalkyl, aryloxy, acyloxy, an acyloxyalkyl wherein the alkyl is $C_1$–$C_6$, amino, a monoalkylamino wherein the alkyl is $C_1$–$C_6$, a dialkylamino wherein the alkyl is $C_1$–$C_6$, acrylamino, ureido, thioureido, carboxy, a carboxyalkyl wherein the alkyl is $C_1$–$C_6$, cyano, a cyanoalkyl wherein the alkyl is $C_1$–$C_6$, C-formyl, C-acyl, a dialkoxymethyl wherein the alkoxy is $C_1$–$C_6$, an aminoalkyl wherein the alkyl is $C_1$–$C_6$, and $SO_nR_1$ wherein n=0, 1, 2, or 3, $R_1$ is H, a $C_1$–$C_6$ alkyl or aryl; and wherein Z is selected from the group consisting of methyl, aryl, a substituted aryl wherein the aryl substitutents are selected from the group consisting of $C_1$–$C_6$ alkyls, nitro and halo, a polycyclic aromatic alkyl containing 2–4 aromatic rings, $C_1$–$C_6$ alkyl, $C_2$–$C_6$ alkenyl, $C_6$ alkynyl, halomethyl, $C_3$–$C_6$ haloalkyl, $C_1$–$C_3$ hydroxyalkyl, $C_1$–$C_6$ halohydroxy alkyl, acyloxy, an acyloxyalkyl wherein the alkyl is $C_1$–$C_3$, carboxy, the acid and salt forms of carboxyalkyl wherein the alkyl is $C_1$–$C_6$, $C_1$–$C_8$ alkoxy, carbonyl, carbamoyl, a carbamoylalkyl wherein the alkyl is $C_1$–$C_6$, hydrazinocarbonyl, a carbamoylalkyl wherein the alkyl is $C_1$–$C_6$, hydrazinocarbonyl, chlorocarbonyl, cyano, $C_2$–$C_9$ cyanoalkyl, C-formyl, a dialkoxymethyl wherein the alkoxy is $C_1$–$C_6$, C-acyl, an alkoxy hydroxyalkyl wherein the alkyl and the alkoxy are $C_1$–$C_4$, carboxymethyl thio, a carboalkoxy alkyl wherein the alkoxy and alkyl are $C_1$–$C_6$, a monoalkylamino hydroxylalkyl wherein the alkyl is $C_1$–$C_6$, a dialkylamino hydroxyalkyl wherein the alkyl is $C_1$–$C_6$, amino hydroxyalkyl wherein the alkyl is $C_1$–$C_6$, a peptide, a monosaccharide selected from the group consisting of aldotetroses and aldohexoses, a polysaccharide selected from the group consisting of sucrose, lactose, maltose and cellobiose, a nucleic acid segment, a steroid selected from the group consisting of testosterone, nortestosterone, and dihydrotestosterone, and $SO_nR_1$ wherein n is 0, 1, 2, or 3 and $R_1$ is H, $C_1$–$C_6$ alkyl or aryl, and a pharmaceutically acceptable excipient.

12. A pharmaceutical composition comprising a compound of the formula:

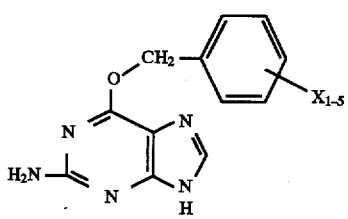

wherein each of $X_1$–$X_5$ is selected from the group consisting of $C_2$–$C_8$ alkoxyalkyl, aryloxy, acyloxy, an acyloxyalkyl wherein the alkyl is $C_1$–$C_3$, hydrazino, hydroxyamino, acylamino, or nitro at o and m-positions, m-methyl, $C_1$–$C_3$ hydroxy alkyl, $C_2$–$C_6$ alkyl, C-formyl, and aryl, and a pharmaceutically acceptable excipient.

13. A pharmaceutical composition comprising a compound of the formula:

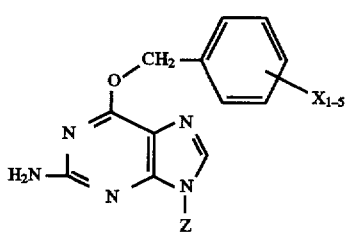

wherein Z is 1-β-D-ribofuranoside or 1-β-D-2-deoxy ribofuranoside and wherein each of $X_1$–$X_5$ is selected from the group consisting of $C_2$–$C_8$ alkoxyalkyl, aryloxy, acyloxy, an acyloxyalkyl wherein the alkyl is $C_1$–$C_6$, acylamino, and nitro, and a pharmaceutically acceptable excipient.

14. A pharmaceutical composition comprising a compound of the formula:

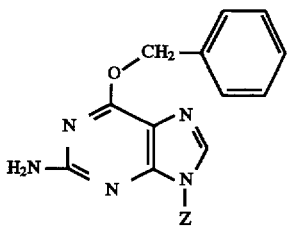

wherein Z is carboethoxymethyl, a conjugate acid form of a carboxymethyl group, a carboxylate anion of a carboxymethyl group as sodium salt, carbamoyl methyl, 2-hydroxybutyl, cyanomethyl, pivaloyloxymethyl, 3-amino-2-hydroxypropyl, 3-alkylamino-2-hydroxypropyl, and 3-dialkylamino-2-hydroxypropyl, and a pharmaceutically acceptable excipient.

15. A method of enhancing the chemotherapeutic treatment of tumor cells in a host comprising administering to the host a chemotherapeutic treatment amount of an $O^6$-substituted guanine compound of claim 5 and an anti-neoplastic alkylating agent whose mechanism of action involves modification of the $O^6$ position of DNA-guanine residue.

16. The method of claim 15, wherein said tumor is selected from the group consisting of colon tumor, brain tumor, prostate tumor, pancreatic tumor and skin tumor.

17. The method of claim 15, wherein said anti-neoplastic alkylating agent is selected from the group consisting of 1,3-bis (2-chloroethyl)-1-nitrosourea, 1-(2-chloroethyl)-3-cyclohexyl-1-nitrosourea, 1-(2-chloroethyl)-3-(4-methylcyclohexyl)-1-nitrosourea, 1-(2-chloroethyl)-3-(4-amino-2-methyl-5-pyrimidinyl) methyl-1-nitrosourea, 1-(2-chloroethyl)-3-(2-hydroxyethyl)-1-nitrosourea, 2-chloroethylmethylsulfonylmethanesulfonate, 1-ethylphosphonic acid diethyl ester, 2-deoxy-2-(3-methyl-3-nitrosoureido)-D-glucopyranose, N-(1-methylethyl)-4-benzamide, 8-carbamoyl-3-methylimidazo-1,2,3,5-tetrazin-4-(3H)-one and 5-(3,3-dimethyl-1-triazenyl)-1H-imidazole-4-carboxamide.

18. The pharmaceutical composition of claim 11 wherein said compound is selected from the group consisting of $O^6$-benzyl-9-acetylguanine, $O^6$-benzyl-9-methylguanine, $O^6$-benzyl-9-(pivaloyloxymethyl)guanine, $O^6$-benzyl-9-(3-chloro-2-hydroxypropyl)guanine, $O^6$-benzyl-9-(2-hydroxy-3-isopropylaminopropyl)guanine, $O^6$-benzyl-9-(3-t-butylamino-2-hydroxypropyl)guanine, $O^6$-benzyl-9-(2-hydroxy-3-isopropoxypropyl)guanine, $O^6$-benzyl-9-(4-androstan-3-one-17β-oxycarbonylmethyl)guanine and $O^6$-benzyl-9-(5α-androstan-3-one-17β-oxycarbonylmethyl)guanine, and a pharmaceutically acceptable excipient.

19. The pharmaceutical composition of claim 12 wherein said compound is selected from the group consisting of $O^6$-(p-bromobenzyl)guanine, $O^6$-(p-isopropylbenzyl) guanine, $O^6$-(p-n-butylbenzyl)guanine, $O^6$-(p-phenylbenzyl) guanine, $O^6$-(3,5-dimethylbenzyl)guanine, $O^6$-(p-hydroxymethylbenzyl)guanine, and $O^6$-(p-formylbenzyl) guanine, and a pharmaceutically acceptable excipient.

20. The pharmaceutical composition of claim 11 which further comprises an anti-neoplastic alkylating agent.

21. The pharmaceutical composition of claim 12 which further comprises an anti-neoplastic alkylating agent.

22. The pharmaceutical composition of claim 13 which comprises an anti-neoplastic alkylating agent.

23. The pharmaceutical composition of claim 14 which comprises an anti-neoplastic alkylating agent.

24. A compound of the formula:

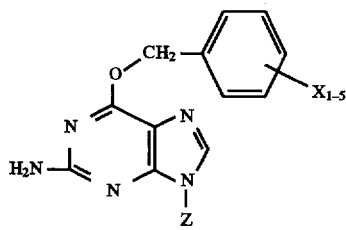

wherein each of $X_1$–$C_5$ is selected from the group consisting of hydroxy, aryl, a $C_1$–$C_8$ alkyl substituted aryl, a polycyclic aromatic alkyl containing 2–4 aromatic rings wherein the alkyl is a $C_1$–$C_6$, a $C_3$–$C_8$ cycloalkyl, a $C_2$–$C_6$ alkenyl, a $C_2$–$C_6$ alkynyl, a $C_1$–$C_6$ hydroxyalkyl, a $C_2$–$C_8$ alkoxyalkyl, aryloxy, acyloxy, an acyloxyalkyl wherein the alkyl is $C_1$–$C_6$, amino, a monoalkylamino wherein the alkyl is $C_1$–$C_6$, a dialkylamino wherein the alkyl is $C_1$–$C_6$, acylamino, ureido, thioureido, carboxy, a carboxyalkyl wherein the alkyl is $C_1$–$C_6$, cyano, a cyanoalkyl wherein the alkyl is $C_1$–$C_6$, C-formyl, C-acyl, a dialkoxyethyl wherein the alkoxy is $C_1$–$C_6$, an aminoalkyl wherein the alkyl is $C_1$–$C_6$, and $SO_nR_1$ wherein n=0, 1, 2 or 3, $R_1$ is H, a $C_1$–$C_6$ alkyl or aryl; and wherein Z is selected from the group consisting of aryl, a substituted aryl wherein the aryl substituents are selected from the group consisting of $C_1$–$C_6$ alkyls, nitro and halo, a polycyclic aromatic alkyl containing 2–4 aromatic rings, $C_2$–$C_6$ alkenyl, $C_6$ alkynyl, halomethyl, $C_1$–$C_3$ hydroxyalkyl, $C_1$–$C_6$ halohydroxy alkyl, acyloxy, pivaloyloxyethyl, carboxy, the acid and salt forms of carboxyalkyl wherein the alkyl is $C_1$–$C_6$, $C_1$–$C_8$ alkoxy, carbonyl, carboyl, a carbamoylalkyl wherein the alkyl is $C_1$–$C_6$, hydrazinocarbonyl, chlorocarbonyl, cyano, $C_2$–$C_9$ cyanoalkyl, C-formyl, a dialkoxyethyl wherein the alkoxy is $C_1$–$C_6$, C-acyl, an alkoxy hydroxyalkyl wherein the alkyl and the alkoxy are $C_1$–$C_4$, carboxyethyl thio, a carboalkoxy alkyl wherein the alkoxy and alkyl are $C_1$–$C_6$, a monoalkylamino hydroxyalkyl wherein the alkyl is $C_1$–$C_6$, a dialkylamino hydroxyalkyl wherein the alkyl is $C_1$–$C_6$, amino hydroxyalkyl wherein the alkyl is $C_1$–$C_6$, a peptide, a monosaccharide selected from the group consisting of aldotetroses, aldopentoses and aldohexoses, a polysaccharide selected from the group consisting of sucrose, lactose, maltose and cellobiose, a nucleic acid segment, asteroid selected from the group consisting of testosterone, nortestosterone, and dihydrotestosterone, and $SO_nR_1$ wherein n is 0, 1, 2, or 3 and $R_1$ is H, $C_1$–$C_6$ alkyl or aryl.

25. A compound of the formula:

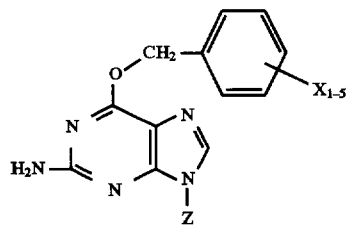

wherein Z is 1-β-D-2-deoxyribofuranoside and wherein $X_1$–$X_5$ is selected from the group consisting of $C_2$–$C_8$ alkoxyalkyl, aryloxy, acyloxy, an acyloxyalkyl wherein the alkyl is $C_1$–$C_6$, acylamino, and nitro.

26. A compound of the formula:

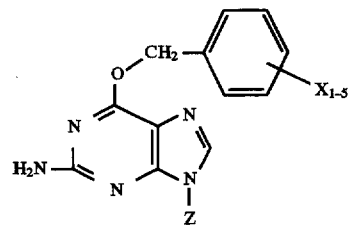

wherein each of $X_1$–$X_5$ is selected from the group consisting of hydroxy, aryl, a $C_1$–$C_8$ alkyl substituted aryl, a polycyclic aromatic alkyl containing 2–4 aromatic rings wherein the alkyl is a $C_1$–$C_6$, a $C_3$–$C_8$ cycloalkyl, a $C_2$–$C_6$ alkenyl, a $C_2$–$C_6$ alkynyl, a $C_1$–$C_6$ hydroxyalkyl, a $C_1$–$C_8$ alkoxy, a $C_2$–$C_8$ alkoxyalkyl, aryloxy, acyloxy, an acyloxyalkyl wherein the alkyl is $C_1$–$C_6$, amino, a monoalkylamino wherein the alkyl is $C_1$–$C_6$, a dialkylamino wherein the alkyl is $C_1$–$C_6$, acylamino, ureido, thioureido, carboxy, a carboxyalkyl wherein the alkyl is $C_1$–$C_6$, cyano, a cyanoalkyl wherein the alkyl is $C_1$–$C_6$, C-formyl, C-acyl, a dialkoxymethyl wherein the alkoxy is $C_1$–$C_6$, an aminoalkyl wherein the alkyl is $C_1$–$C_6$, and $SO_nR_1$ wherein n=0, 1, 2 or 3, $R_1$ is H, a $C_1$–$C_6$ alkyl or aryl; and wherein Z is selected from the group consisting of methyl, aryl, a substituted aryl wherein the aryl substituents are selected from the group consisting of $C_1$–$C_6$ alkyls, nitro and halo, a polycyclic aromatic alkyl containing 2–4 aromatic rings, $C_1$–$C_6$ alkyl, $C_2$–$C_6$ alkenyl, $C_6$ alkynyl, halomethyl, $C_3$–$C_6$ haloalkyl, $C_1$–$C_3$ hydroxyalkyl, $C_1$–$C_6$ halohydroxy alkyl, acyloxy, an acyloxyalkyl wherein the alkyl is $C_1$–$C_3$, carboxy, the acid and salt forms of carboxyalkyl wherein the alkyl is $C_1$–$C_6$, $C_1$–$C_8$ alkoxy, carbonyl, carbamoyl, a carbamoylalkyl wherein the alkyl is $C_1$–$C_6$, hydrazinocarbonyl, chlorocarbonyl, cyano, $C_2$–$C_9$ cyanoalkyl, C-formyl, a dialkoxymethyl wherein the alkoxy is $C_1$–$C_6$, C-acyl, an alkoxy hydroxyalkyl wherein the alkyl and the alkoxy are $C_1$–$C_4$, carboxymethyl thio, a carboalkoxy alkyl wherein the alkoxy and alkyl are $C_1$–$C_6$, a monoalkylamino hydroxylalkyl wherein the alkyl is $C_1$–$C_6$, a dialkylamino hydroxyalkyl wherein the alkyl is $C_1$–$C_6$, amino hydroxyalkyl wherein the alkyl is $C_1$–$C_6$, a peptide, a monosaccharide selected from the group consisting of aldotetroses, aldopentoses and aldohexoses, a polysaccharide selected from the group consisting of sucrose, lactose, maltose and cellobiose, a nucleic acid segment, asteroid selected from the group consisting of testosterone, nortestosterone, and dihydrotestosterone, and $SO_nR_1$ wherein n is 0, 1, 2, or 3 and $R_1$ is H, $C_1$–$C_6$ alkyl or aryl.

27. The pharmaceutical composition of claim 18 which comprises an anti-neoplastic alkylating agent.

28. The pharmaceutical composition of claim 19 which comprises an anti-neoplastic alkylating agent.

29. A method for treating tumor cells in a host which comprises administering to the host an amount effective to reduce AGT activity in the host of a compound selected from the group consisting of (a) a compound of the formula:

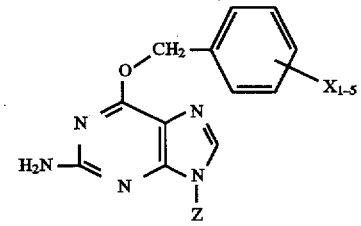

wherein $X_1$–$X_5$ are selected from the group consisting of hydrogen, halogen, hydroxy, aryl, a $C_1$–$C_8$ alkyl substituted aryl, nitro, a polycyclic aromatic alkyl containing 2–4 aromatic rings wherein the alkyl is a $C_1$–$C_6$, a $C_3$–$C_8$ cycloalkyl, a $C_2$–$C_6$ alkenyl, a $C_2$–$C_6$ alkynyl, a $C_1$–$C_6$ hydroxyalkyl, a $C_1$–$C_8$ alkoxy, a $C_2$–$C_8$ alkoxyalkyl, aryloxy, acyloxy, an acyloxyalkyl wherein the alkyl is $C_1$–$C_6$, amino, a monoalkylamino wherein the alkyl is $C_1$–$C_6$, a dialkylamino wherein the alkyl is $C_1$–$C_6$, acylamino, ureido, thioureido, carboxy, a carboxyalkyl wherein the alkyl is $C_1$–$C_6$, cyano, a cyanoalkyl wherein the alkyl is $C_1$–$C_6$, C-formyl, C-acyl, a dialkoxymethyl wherein the alkoxy is $C_1$–$C_6$, an aminoalkyl wherein the alkyl is $C_1$–$C_6$, and $SO_nR_1$ wherein n=0, 1, 2 or 3, $R_1$ is H, a $C_1$–$C_6$ alkyl or aryl; and wherein Z is selected from the group consisting of methyl, aryl, a substituted aryl wherein the aryl substituents are selected from the group consisting of $C_1$–$C_6$ alkyls, nitro and halo, a polycyclic aromatic alkyl containing 2–4 aromatic rings, $C_1$–$C_6$ alkyl, $C_2$–$C_6$ alkenyl, $C_6$ alkynyl, halomethyl, $C_3$–$C_6$ haloalkyl, $C_1$–$C_3$ hydroxyalkyl, $C_1$–$C_6$ halohydroxy alkyl, acyloxy, an acyloxyalkyl wherein the alkyl is $C_1$–$C_3$, carboxy, the acid and salt forms of carboxyalkyl wherein the alkyl is $C_1$–$C_6$, $C_1$–$C_8$ alkoxy, carbonyl, carbamoyl, a carbamoylalkyl wherein the alkyl is $C_1$–$C_6$, hydrazinocarbonyl, chlorocarbonyl, cyano, $C_2$–$C_9$ cyanoalkyl, C-formyl, a dialkoxymethyl wherein the alkoxy is $C_1$–$C_6$, C-acyl, an alkoxy hydroxyalkyl wherein the alkyl and the alkoxy are $C_1$–$C_4$, carboxymethyl thio, a carboalkoxy alkyl wherein the alkoxy and alkyl are $C_1$–$C_6$, a monoalkylamino hydroxylalkyl wherein the alkyl is $C_1$–$C_6$, a dialkylamino hydroxyalkyl wherein the alkyl is $C_1$–$C_6$, amino hydroxyalkyl wherein the alkyl is $C_1$–$C_6$, a peptide, a monosaccharide selected from the group consisting of aldotetroses, aldopentoses and aldohexoses, a polysaccharide selected from the group consisting of sucrose, lactose, maltose and cellobiose, a nucleic acid segment selected from the group consisting of 5'-d(AACAGCCATATG*GCCC)-3', 5'-d(GTGGGCGCTG*GAGGCG)-3', 5'-d(GTGGGCGCTGG*GAGGCG)-3', and 5'-d(GTGGGCGCTG*G*AGGCG)-3' wherein G* is $O^6$-benzyl-2'-deoxyguanosine residue, a steroid selected from the group consisting of testosterone, nortestosterone, and dihydrotestosterone, and $SO_nR_1$ wherein n is 0, 1, 2, or 3 and $R_1$ is H, $C_1$–$C_6$ alkyl or aryl;

(b) a compound of the formula:

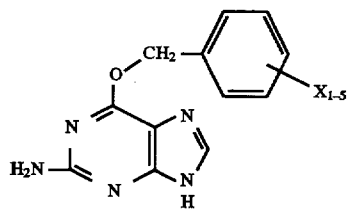

wherein each of $X_1$–$X_5$ is selected from the group consisting of $C_2$–$C_8$ alkoxyalkyl, aryloxy, acyloxy, an acyloxyalkyl wherein the alkyl is $C_1$–$C_3$, hydrazino, hydroxyamino, acylamino, or nitro at o and m-positions, m-methyl, $C_1$–$C_4$ hydroxy alkyl, $C_2$–$C_6$ alkyl, C-formyl, and aryl;

(c) a compound of the formula:

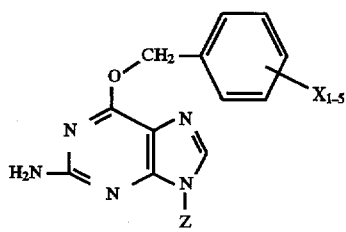

wherein Z is 1-β-D-ribofuranoside or 1-β-D-2-deoxy ribofuranoside and wherein each of $X_1$–$X_5$ is selected from the group consisting of $C_2$–$C_8$ alkoxyalkyl, aryloxy, acyloxy, an acyloxyalkyl wherein the alkyl is $C_1$–$C_6$, acylamino, and nitro;

(d) a compound of the formula:

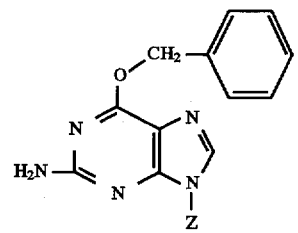

wherein Z is carboethoxymethyl, a conjugate acid form of a carboxymethyl group, a carboxylate anion of a carboxymethyl group as sodium salt, carbamoyl methyl, 2-hydroxybutyl, cyanomethyl, pivaloyloxymethyl, 3-amino-2-hydroxypropyl, 3-alkylamino-2-hydroxypropyl, or 3-dialkylamino-2-hydroxypropyl;

(e) a compound represented by the formula

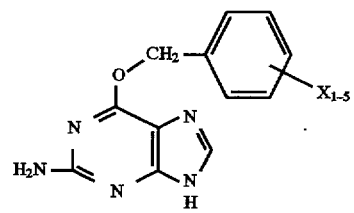

wherein each of $X_1$–$X_5$ is selected from the group consisting of halogen, nitro, phenyl, $C_1$–$C_4$ alkyl substituted phenyl, a $C_1$–$C_4$ alkyl, a $C_1$–$C_4$ alkoxy, a $C_2$–$C_4$ alkenyl, a $C_2$–$C_4$ alkynyl, an amino, a $C_1$–$C_4$ monoalkylamino, a $C_1$–$C_4$ dialkylamino, a trifluoromethyl, hydroxy, hydroxymethyl, and $SO_nR_1$ wherein n is 0, 1, 2, or 3 and $R_1$ is hydrogen, a $C_1$–$C_4$ alkyl, phenyl, or a $C_1$–$C_4$ alkyl substituted phenyl; and (f) a compound of the formula

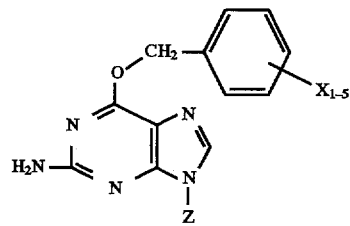

wherein Z is 1-β-D-riobofuranoside or 1-β-D-2-deoxyriobofuranoside, and $X_1$–$X_5$ is each selected from the group consisting of halogen, nitro, phenyl, $C_1$–$C_4$ alkyl, $C_1$–$C_4$ alkoxy, $C_2$–$C_4$ alkenyl, $C_2$–$C_4$ alkynyl, amino, $C_1$–$C_4$ monoalkylamino, $C_1$–$C_4$ dialkylamino, trifluoromethyl, hydroxy, hydroxymethyl, and $SO_nR_1$ wherein n is 0, 1, 2, or 3, and $R_1$ is hydrogen, $C_1$–$C_4$ alkyl, or phenyl.

30. A method of enhancing the chemotherapeutic treatment of tumor cells in a host comprising administering to the host a chemotherapeutic treatment amount of an $O^6$-substituted guanine compound selected from the group consisting of (a) a compound of of the formula:

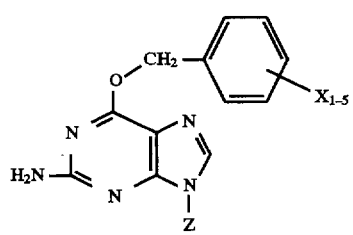

wherein each of $X_1$–$X_5$ is selected from the group consisting of hydrogen, halogen, hydroxy, aryl, a $C_1$–$C_8$ alkyl substituted aryl, nitro, a polycyclic aromatic alkyl containing 2–4 aromatic rings wherein the alkyl is a $C_1$–$C_6$, a $C_3$–$C_8$ cycloalkyl, a $C_2$–$C_6$ alkenyl, a $C_2$–$C_6$ alkynyl, a $C_1$–$C_6$ hydroxyalkyl, a $C_1$–$C_8$ alkoxy, a $C_2$–$C_8$ alkoxyalkyl, aryloxy, acyloxy, an acyloxyalkyl wherein the alkyl is $C_1$–$C_6$, amino, a monoalkylamino wherein the alkyl is $C_1$–$C_6$, a dialkylamino wherein the alkyl is $C_1$–$C_6$, acylamino, ureido, thioureido, carboxy, a carboxyalkyl wherein the alkyl is $C_1$–$C_6$, cyano, a cyanoalkyl wherein the alkyl is $C_1$–$C_6$, C-formyl, C-acyl, a dialkoxymethyl wherein the alkoxy is $C_1$–$C_6$, an aminoalkyl wherein the alkyl is $C_1$–$C_6$, and $SO_nR_1$ wherein n=0, 1, 2 or 3, $R_1$ is H, a $C_1$–$C_6$ alkyl or aryl; and wherein Z is selected from the group consisting of methyl, aryl, a substituted aryl wherein the aryl substituents are selected from the group consisting of $C_1$–$C_6$ alkyls, nitro and halo, a polycyclic aromatic alkyl containing 2–4 aromatic rings, $C_1$–$C_6$ alkyl, $C_2$–$C_6$ alkenyl, $C_6$ alkynyl, halomethyl, $C_3$–$C_6$ haloalkyl, $C_1$–$C_3$ hydroxyalkyl, $C_1$–$C_6$ halohydroxy alkyl, acyloxy, an acyloxyalkyl wherein the alkyl is $C_1$–$C_3$, carboxy, the acid and salt forms of carboxyalkyl wherein the alkyl is $C_1$–$C_6$, $C_1$–$C_8$ alkoxy, carbonyl, carbamoyl, a carbamoylalkyl wherein the alkyl is $C_1$–$C_6$, hydrazinocarbonyl, chlorocarbonyl, cyano, $C_2$–$C_9$ cyanoalkyl, C-formyl, a dialkoxymethyl wherein the alkoxy is $C_1$–$C_6$, C-acyl, an alkoxy hydroxyalkyl wherein the alkyl and the alkoxy are $C_1$–$C_4$, carboxymethyl thio, a carboalkoxy alkyl wherein the alkoxy and alkyl are $C_1$–$C_6$, a monoalkylamino hydroxylalkyl wherein the alkyl is $C_1$–$C_6$, a dialkylamino hydroxyalkyl wherein the alkyl is $C_1$–$C_6$, amino hydroxyalkyl wherein the alkyl is $C_1$–$C_6$, a peptide, a monosaccharide selected from the group consisting of aldotetroses, aldopentoses and aldohexoses, a polysaccharide selected from the group consisting of sucrose, lactose, maltose and cellobiose, a nucleic acid segment selected from the group consisting of 5'-d(AACAGCCATATG*GCCC)-3', 5'-d(GTGGGCGCTG*GAGGCG)-3', 5'-d(GTGGGCGCTGG*GAGGCG)-3', and 5'-(GTGGGCGCTG*G*AGGCG)-3' wherein G* is $O^6$-benzyl 2-deoxyguanosine residue, a steroid selected from the group consisting of testosterone, nortestosterone, and dihydrotestosterone, and $SO_nR_1$ wherein n is 0, 1, 2, or 3 and $R_1$ is H, $C_1$–$C_6$ alkyl or aryl;

(b) a compound of the formula:

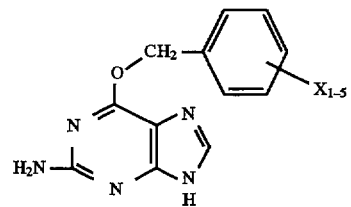

wherein each of $X_1$–$X_5$ is selected from the group consisting of $C_2$–$C_8$ alkoxyalkyl, aryloxy, acyloxy, an acyloxyalkyl wherein the alkyl is $C_1$–$C_3$, hydrazino, hydroxyamino, acylamino, or nitro at o and m-positions, m-methyl, $C_1$–$C_3$ hydroxy alkyl, $C_2$–$C_6$ alkyl, C-formyl, and aryl;

(c) a compound of of the formula:

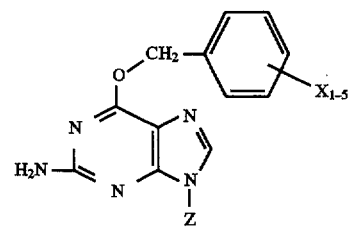

wherein Z is 1-β-D-ribofuranoside or 1-β-D-2-deoxy ribofuranoside and wherein each of $X_1$–$X_5$ is selected from the group consisting of $C_2$–$C_8$ alkoxyalkyl, aryloxy, acyloxy, an acyloxyalkyl wherein the alkyl is $C_1$–$C_6$, acylamino, and nitro.

(d) a compound of the formula:

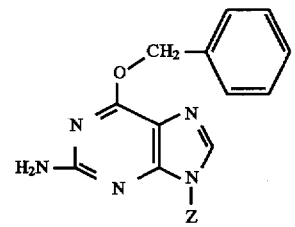

wherein Z is carboethoxymethyl, a conjugate acid form of a carboxymethyl group, a carboxylate anion of a carboxymethyl group as sodium salt, carbamoyl methyl, 2-hydroxybutyl, cyanomethyl, pivaloyloxymethyl, 3-amino-2-hydroxypropyl, 3-alkylamino-2-hydroxypropyl, and 3-dialkylamino-2-hydroxypropyl;

(e) a compound represented by the formula

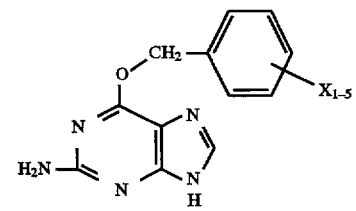

wherein each of $X_1$–$X_5$ is selected from the group consisting of halogen, nitro, phenyl, $C_1$–$C_4$ alkyl substituted phenyl, a $C_1$–$C_4$ alkyl, a $C_1$–$C_4$ alkoxy, a $C_2$–$C_4$ alkenyl, a $C_2$-$C_4$ alkynyl, an amino, a $C_1$-$C_4$ monoalkylamino, a $C_1$-$C_4$ dialkylamino, a trifluoromethyl, hydroxy, hydroxymethyl, and $SO_nR_1$ wherein n is 0, 1, 2, or 3 and $R_1$ is hydrogen, a $C_1$-$C_4$ alkyl, phenyl, or a $C_1$-$C_4$ alkyl substituted phenyl; and (f) a compound of the formula

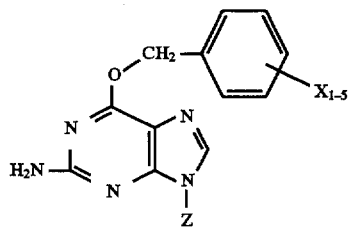

wherein Z is 1-β-D-riobofuranoside or 1-β-D-2-deoxyriobofuranoside, and $X_1$-$X_5$ is each selected from the group consisting of halogen, nitro, phenyl, $C_1$-$C_4$ alkyl, $C_1$-$C_4$ alkoxy, $C_2$-$C_4$ alkenyl, $C_2$-$C_4$ alkynyl, amino, $C_1$-$C_4$ monoalkylamino, $C_1$-$C_4$ dialkylamino, trifluoromethyl, hydroxy, hydroxymethyl, and $SO_nR_1$ wherein n is 0, 1, 2, or 3, and $R_1$ is hydrogen, $C_1$-$C_4$ alkyl, or phenyl, and an anti-neoplastic alkylating agent whose mechanism of action involves modification of the $O^6$ position of DNA-guanine residue.

31. The method of claim 30, wherein said $O^6$-substituted guanine compound is a compound of of the formula:

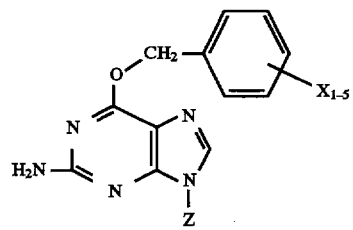

wherein each of $X_1$-$X_5$ is selected from the group consisting of hydrogen, halogen, hydroxy, aryl, a $C_1$-$C_8$ alkyl substituted aryl, nitro, a polycyclic aromatic alkyl containing 2-4 aromatic rings wherein the alkyl is a $C_1$-$C_6$, a $C_3$-$C_8$ cycloalkyl, a $C_2$-$C_6$ alkenyl, a $C_2$-$C_6$ alkynyl, a $C_1$-$C_6$ hydroxyalkyl, a $C_1$-$C_8$ alkoxy, a $C_2$-$C_8$ alkoxyalkyl, aryloxy, acyloxy, an acyloxyalkyl wherein the alkyl is $C_1$-$C_6$, amino, a monoalkylamino wherein the alkyl is $C_1$-$C_6$, a dialkylamino wherein the alkyl is $C_1$-$C_6$, acylamino, ureido, thioureido, carboxy, a carboxyalkyl wherein the alkyl is $C_1$-$C_6$, cyano, a cyanoalkyl wherein the alkyl is $C_1$-$C_6$, C-formyl, C-acyl, a dialkoxymethyl wherein the alkoxy is $C_1$-$C_6$, an aminoalkyl wherein the alkyl is $C_1$-$C_6$, and $SO_nR_1$ wherein n=0, 1, 2 or 3, $R_1$ is H, a $C_1$-$C_6$ alkyl or aryl; and wherein Z is selected from the group consisting of methyl, aryl, a substituted aryl wherein the aryl substituents are selected from the group consisting of $C_1$-$C_6$ alkyls, nitro and halo, a polycyclic aromatic alkyl containing 2-4 aromatic rings, $C_1$-$C_6$ alkyl, $C_2$-$C_6$ alkenyl, $C_6$ alkynyl, halomethyl, $C_3$-$C_6$ haloalkyl, $C_1$-$C_3$ hydroxyalkyl, $C_1$-$C_6$ halohydroxy alkyl, acyloxy, an acyloxyalkyl wherein the alkyl is $C_1$-$C_3$, carboxy, the acid and salt forms of carboxyalkyl wherein the alkyl is $C_1$-$C_6$, $C_1$-$C_8$ alkoxy, carbonyl, carbamoyl, a carbamoylalkyl wherein the alkyl is $C_1$-$C_6$, hydrazinocarbonyl, chlorocarbonyl, cyano, $C_2$-$C_9$ cyanoalkyl, C-formyl, a dialkoxymethyl wherein the alkoxy is $C_1$-$C_6$, C-acyl, an alkoxy hydroxyalkyl wherein the alkyl and the alkoxy are $C_1$-$C_4$, carboxymethyl thio, a carboalkoxy alkyl wherein the alkoxy and alkyl are $C_1$-$C_6$, a monoalkylamino hydroxyalkyl wherein the alkyl is $C_1$-$C_6$, a dialkylamino hydroxyalkyl wherein the alkyl is $C_1$-$C_6$, amino hydroxyalkyl wherein the alkyl is $C_1$-$C_6$, a peptide, a monosaccharide selected from the group consisting of aldotetroses, aldopentoses and aldohexoses, a polysaccharide selected from the group consisting of sucrose, lactose, maltose and cellobiose, a nucleic acid segment selected from the group consisting of 5'-d (AACAGCCATATG*GCCC)-3', 5'-(GTGGGCGCTG*GAGGCG)-3', 5'-(GTGGGCGCTGG*GAGGCG)-3', and 5'-d (GTGGGCGCTG*G*AGGCG)-3' wherein G* is $O^6$-benzyl 2-deoxyguanosine residue, a steroid selected from the group consisting of testosterone, nortestosterone, and dihydrotestosterone, and $SO_nR_1$ wherein n is 0, 1, 2, or 3 and $R_1$ is H, $C_1$-$C_6$ alkyl or aryl.

32. The method of claim 30, wherein said $O^6$-substituted guanine compound is a compound of the formula:

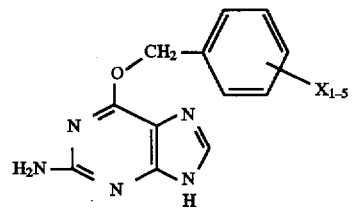

wherein each of $X_1$-$X_5$ is selected from the group consisting of $C_2$-$C_8$ alkoxyalkyl, aryloxy, acyloxy, an acyloxyalkyl wherein the alkyl is $C_1$-$C_3$, hydrazino, hydroxyamino, acylamino, or nitro at o and m-positions, m-methyl, $C_1$-$C_3$ hydroxy alkyl, $C_2$-$C_6$ alkyl, C-formyl, and aryl.

33. The method of claim 30, wherein said $O^6$-substituted guanine compound is a compound of of the formula:

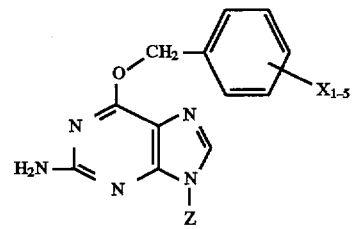

wherein Z is 1-β-D-ribofuranoside or 1-β-D-2-deoxy ribofuranoside and wherein each of $X_1$-$X_5$ is selected from the group consisting of $C_2$-$C_8$ alkoxyalkyl, aryloxy, acyloxy, an acyloxyalkyl wherein the alkyl is $C_1$-$C_6$, acylamino, and nitro.

34. The method of claim 30, wherein said $O^6$-substituted guanine compound is a compound of the formula:

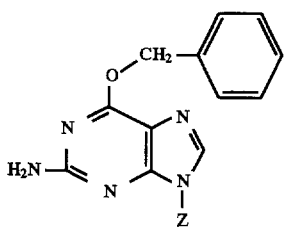

wherein Z is carboethoxymethyl, a conjugate acid form of a carboxymethyl group, a carboxylate anion of a carboxymethyl group as sodium salt, carbamoyl methyl, 2-hydroxybutyl, cyanomethyl, pivaloyloxymethyl, 3-amino-2-hydroxypropyl, 3-alkylamino-2-hydroxypropyl, and 3-dialkylamino-2-hydroxypropyl.

35. The method of claim 30 wherein said $O^6$-substituted guanine compound is a compound represented by the formula

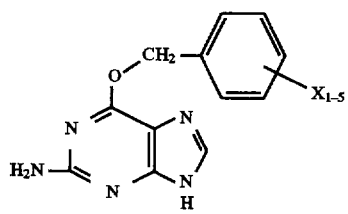

wherein each of $X_1$–$X_5$ is selected from the group consisting of halogen, nitro, phenyl, $C_1$–$C_4$ alkyl substituted phenyl, a $C_1$–$C_4$ alkyl, a $C_1$–$C_4$ alkoxy, a $C_2$–$C_4$ alkenyl, a $C_2$–$C_4$ alkynyl, an amino, a $C_1$–$C_4$ monoalkylamino, a $C_1$–$C_4$ dialkylamino, a trifluoromethyl, hydroxy, hydroxymethyl, and $SO_nR_1$ wherein n is 0, 1, 2, or 3 and $R_1$ is hydrogen, a $C_1$–$C_4$ alkyl, phenyl, or a $C_1$–$C_4$ alkyl substituted phenyl.

36. The method of claim 30 wherein said $O^6$-substituted guanine compound is a compound of the formula

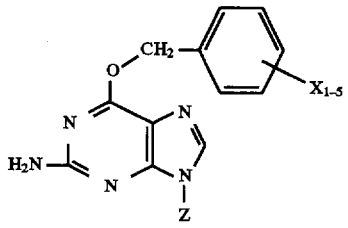

wherein Z is 1-β-D-riobofuranoside or 1-β-D-2-deoxyriobofuranoside, and $X_1$–$X_5$ is each selected from the group consisting of halogen, nitro, phenyl, $C_1$–$C_4$ alkyl, $C_1$–$C_4$ alkoxy, $C_2$–$C_4$ alkenyl, $C_2$–$C_4$ alkynyl, amino, $C_1$–$C_4$ monoalkylamino, $C_1$–$C_4$ dialkylamino, trifluoromethyl, hydroxy, hydroxymethyl, and $SO_nR_1$ wherein n is 0, 1, 2, or 3, and $R_1$ is hydrogen, $C_1$–$C_4$ alkyl, or phenyl, and an anti-neoplastic alkylating agent whose mechanism of action involves modification of the $O^6$ position of DNA-guanine residue.

37. The method of claim 30 wherein said tumor is selected from the group consisting of colon tumor, brain tumor, prostate tumor, pancreatic tumor and skin tumor.

38. The method of claim 30 wherein said anti-neoplastic alkylating agent is selected from the group consisting of 1,3-bis(2-chloroethyl)-1-nitrosourea, 1-(2-chloroethyl)-3-cyclohexyl-1-nitrosourea, 1-(2-chloroethyl)-3-(4-methylcyclohexyl)-1-nitrosourea, 1-(2-chloroethyl)-3-(g4-amino-2-methyl-5-pyrimidinyl)methyl-1-nitrosourea, 1-(2-chloroethyl)-3-(2-hydroxyethyl)-1-nitrosourea, 2-chloroethylmethylsulfonylmethanesulfonate, 1-[N-(2-chloroethyl)-N-nitrosoureido]ethylphosphonic acid diethyl ester, 2-deoxy-2-(3-methyl-3-nitrosoureido)-D-glucopyranose, N-(1-methylethyl)-4-[(2-methylhydrazino)methyl]benzamide, 8-carbamoyl-3-methylimidazo[5,1-d]-1,2,3,5-tetrazin-4-(3H)-one and 5-(3, 3-dimethyl-1-triazenyl)-1H-imidazole-4-carboxamide.

39. The method of claim 31 wherein said tumor is selected from the group consisting of colon tumor, brain tumor, prostate tumor, pancreatic tumor and skin tumor.

40. The method of claim 31 wherein said anti-neoplastic alkylating agent is selected from the group consisting of 1,3-bis(2-chloroethyl)-1-nitrosourea, 1-(2-chloroethyl)-3-cyclohexyl-1-nitrosourea, 1-(2-chloroethyl)-3-(4-methylcyclohexyl)-1-nitrosourea, 1-(2-chloroethyl)-3-(4-amino-2-methyl-5-pyrimidinyl)methyl-1-nitrosourea, 1-(2-chloroethyl)-3-(2-hydroxyethyl)-1-nitrosourea, 2-chloroethylmethylsulfonylmethanesulfonate, 1-[N-(2-chloroethyl)-N-nitrosoureido]ethylphosphonic acid diethyl ester, 2-deoxy-2-(3-methyl-3-nitrosoureido)-D-glucopyranose, N-(1-methylethyl)-4-[(2-methylhydrazino)methyl]benzamide, 8-carbamoyl-3-methylimidazo[5,1-d]-1,2,3,5-tetrazin-4-(3H)-one and 5-(3, 3-dimethyl-1-triazenyl)-1H-imidazole-4-carboxamide.

41. The method of claim 32 wherein said tumor is selected from the group consisting of colon tumor, brain tumor, prostate tumor, pancreatic tumor and skin tumor.

42. The method of claim 32 wherein said anti-neoplastic alkylating agent is selected from the group consisting of 1,3-bis(2-chloroethyl)-1-nitrosourea, 1-(2-chloroethyl)-3-cyclohexyl-1-nitrosourea, 1-(2-chloroethyl)-3-(4-methylcyclohexyl)-1-nitrosourea, 1-(2-chloroethyl)-3-(4-amino-2-methyl-5-pyrimidinyl) methyl-1-nitrosourea, 1-(2-chloroethyl)-3-(2-hydroxyethyl)-1-nitrosourea, 2-chloroethylmethylsulfonylmethanesulfonate, 1-[N-(2-chloroethyl)-N-nitrosoureido]ethylphosphonic acid diethyl ester, 2-deoxy-2-(3-methyl-3-nitrosoureido)-D-glucopyranose, N-(1-methylethyl)-4-[(2-methylhydrazino) methyl]benzamide, 8-carbamoyl-3-methylimidazo [5,1-d]-1,2,3,5-tetrazin-4-(3H)-one and 5-(3, 3-dimethyl-1-triazenyl)-1H-imidazole-4-carboxamide.

43. The method of claim 33 wherein said tumor is selected from the group consisting of colon tumor, brain tumor, prostate tumor, pancreatic tumor and skin tumor.

44. The method of claim 33 wherein said anti-neoplastic alkylating agent is selected from the group consisting of 1,3-bis(2-chloroethyl)-1-nitrosourea, 1-(2-chloroethyl)-3-cyclohexyl-1-nitrosourea, 1-(2-chloroethyl)-3-(g4-methylcyclohexyl)-1-nitrosourea, 1-(2-chloroethyl)-3-(4-amino-2-methyl-5-pyrimidinyl)methyl-1-nitrosourea, 1-(2-chloroethyl)-3-(2-hydroxyethyl)-1-nitrosourea, 2-chloroethylmethylsulfonylmethanesulfonate, 1-[N-(2-chloroethyl)-N-nitrosoureido]ethylphosphonic acid diethyl ester, 2-deoxy-2-(3-methyl-3-nitrosoureido)-D-glucopyranose, N-(1-methylethyl)-4-[(2-methylhydrazino) methyl]benzide, 8-carbamoyl-3-methylimidazo [5,1-d]-1,2, 3,5-tetrazin-4-(3H)-one and 5-(3, 3-dimethyl-1-triazenyl)-1H-imidazole-4-carboxamide.

45. The method of claim 34 wherein said tumor is selected from the group consisting of colon tumor, brain tumor, prostate tumor, pancreatic tumor and skin tumor.

46. The method of claim 34 wherein said anti-neoplastic alkylating agent is selected from the group consisting of 1,3-bis(2-chloroethyl)-1-nitrosourea, 1-(2-chloroethyl)-3-cyclohexyl-1-nitrosourea, 1-(2-chloroethyl)-3-(4-methylcyclohexyl)-1-nitrosourea, 1-(2-chloroethyl)-3-(4-amino-2-methyl-5-pyrimidinyl) methyl-1-nitrosourea, 1-(2-chloroethyl)-3-(2-hydroxyethyl)-1-nitrosourea, 2-chloroethylmethylsulfonylmethanesulfonate, 1-[N-(2-chloroethyl)-N-nitrosoureido]ethylphosphonic acid diethyl ester, 2-deoxy-2-(3-methyl-3-nitrosoureido)-D-glucopyranose, N-(1-methylethyl)-4-[(2-methylhydrazino)methyl]benzamide, 8-carbamoyl-3-methylimidazo [5,1-d]-1,2,3,5-tetrazin-4-(3H)-one and 5-(3, 3-dimethyl-1-triazenyl)-1H-imidazole-4-carboxamide.

47. The method of claim 29 wherein said compound is selected from the group consisting of $O^6$-benzyl 9-acetyl guanine, $O^6$-benzyl-9 methyl guanine, $O^6$-benzyl-(pivaloyloxymethyl) guanine, $O^6$-benzyl-9-(3-chloro-2-hydroxypropyl) guanine, $O^6$-benzyl-9 -(2-hydroxy-3-isopropylaminopropyl) guanine, $O^6$-benzyl-9 -(3-t-butylamino-2-hydroxypropyl) guanine, $O^6$-benzyl-9 -(2-hydroxy-3-isopropoxypropyl) guanine, $O^6$-benzyl-9 -(4-androstan-3-one-17β-oxycarbonylmethyl-guanine and $O^6$-benzyl-9-(5α-androstan-3-one-17β-oxycarbonylmethyl) guanine.

48. The method of claim 30 wherein said $O^6$-substituted guanine compound is selected from the group consisting of $O^6$-benzyl 9-acetyl guanine, $O^6$-benzyl-9 methyl guanine, $O^6$-benzyl-9 (pivaloyloxymethyl) guanine, $O^6$-benzyl-9 -(3-chloro-2-hydroxypropyl)guanine, $O^6$-benzyl-9-(2-hydroxy-3-isopropylaminopropyl)guanine, $O^6$-benzyl-9-(3-t-butylamino-2-hydroxypropyl) guanine, $O^6$-benzyl-9-(2-hydroxy-3-isopropoxypropyl) guanine, $O^6$-benzyl-9-(4-androstan-3-one-17β-oxycarbonylmethyl-guanine and $O^6$-benzyl-9-(5α- androstan-3-one-17β-oxycarbonylmethyl)guanine.

49. The method of claim 48 wherein said tumor is selected from the group consisting of colon tumor, brain tumor, prostate tumor, pancreatic tumor and skin tumor.

50. A method of claim 48 wherein said anti-neoplastic alkylating agent is selected from the group consisting of 1,3-bis (2-chloroethyl)-1-nitrosourea, 1-(2-chloroethyl)-3-cyclohexyl-1-nitrosourea, 1-(2-chloroethyl)-3-(4-methylcyclohexyl)-1-nitrosourea, 1-(2-chloroethyl)-3-(4-amino-2-methyl-5-pyrimidinyl) methyl-1-nitrosourea, 1-(2-chloroethyl)-3-(2-hydroxyethyl)-1-nitrosourea, 2-chloroethylmethylsulfonylmethanesulfonate, 1-[N-(2-chloroethyl)-N-nitrosoureido]ethylphosphonic acid diethyl ester, 2-deoxy-2-(3-methyl-3-nitrosoureido)-D-glucopyranose, N- (1-methylethyl)-4-[(2-methylhydrazino) methyl]benzamide, 8-carbamoyl-3-methylimidazo [5,1-d]-1,2,3,5-tetrazin-4-(3H)-one and 5-(3, 3-dimethyl-1-triazenyl)-1H-imidazole-4-carboxamide.

51. The method of claim 29 wherein said compound is selected from the group consisting of $O^6$-(p-bromobenzyl) guanine, $O^6$-(p-isopropylbenzyl)guanine, $O^6$-(p-n-butylbenzyl) guanine, $O^6$-(p-phenylbenzyl)guanine, $O^6$-(3,5-dimethylbenzyl)guanine, $O^6$-(p-hydroxymethylbenzyl) guanine, and $O^6$-(p-formylbenzyl)guanine.

52. The method of claim 32 wherein said $O^6$-substituted guanine compound is selected from the group consisting of $O^6$-(p-bromobenzyl)guanine, $O^6$-(p-isopropylbenzyl) guanine, $O^6$-(p-n-butylbenzyl)guanine, $O^6$-(p-phenylbenzyl) guanine, $O^6$-(3,5-dimethylbenzyl)guanine, $O^6$-(p-hydroxymethylbenzyl)guanine, and $O^6$-(p-formylbenzyl)guanine.

53. The method of claim 52 wherein said tumor is selected from the group consisting of colon tumor, brain tumor, prostate tumor, pancreatic tumor and skin tumor.

54. The method of claim 52 wherein said anti-neoplastic alkylating agent is selected from the group consisting of 1,3-bis (2-chloroethyl)-1-nitrosourea, 1-(2-chloroethyl)-3-cyclohexyl-1-nitrosourea, 1-(2-chloroethyl)-3-(4-methylcyclohexyl)-1-nitrosourea, 1-(2-chloroethyl)-3-(4-amino-2-methyl-5-pyrimidinyl) methyl-1-nitrosourea, 1-(2-chloroethyl)-3-(2-hydroxyethyl)-1-nitrosourea, 2-chloroethylmethyl sulfonylmethanesulfonate, 1-[N-(2-chloroethyl)-N-nitrosoureido]ethylphosphonic acid diethyl ester, 2-deoxy-2-(3-methyl-3-nitrosoureido)-D-glucopyranose, N- (1-methylethyl)-4-[(2-methylhydrazino) methyl]benzamide, 8-carbamoyl-3-methylimidazo [5,1-d]-1,2,3,5- tetrazin-4- (3H) -one and 5-(3, 3 -dimethyl-1-triazenyl)-1H-imidazole-4-carboxamide.

55. The compound of claim 1, wherein $X_1$-$X_5$ are selected from the group consisting of hydrogen, halogen, hydroxy, aryl, a $C_1$-$C_6$ alkyl substituted aryl, nitro, a polycyclic aromatic alkyl containing 2 aromatic rings wherein the alkyl is a $C_1$-$C_6$, a $C_3$-$C_6$ cycloalkyl, a $C_2$-$C_6$ alkenyl, a $C_2$-$C_6$ alkynyl, a $C_1$-$C_6$ hydroxyalkyl, a $C_1$-$C_6$ alkoxy, a $C_2$-$C_8$ alkoxyalkyl, aryloxy, acyloxy, acyloxyalkyl where the alkyl is $C_1$-$C_6$, amino, a monoalkylamino wherein the alkyl is $C_1$-$C_6$, a dialkylamino wherein the alkyl is $C_1$-$C_6$, acylamino, nitro, ureido, thioureido, carboxy, a carboxyalkyl wherein the alkyl is $C_1$-$C_6$, cyano, a cyanoalkyl wherein the alkyl is $C_1$-$C_6$, C-formyl, C-acyl, a dialkoxymethyl wherein the alkoxy is $C_1$-$C_6$, an aminoalkyl wherein the alkyl is $C_1$-$C_6$, and $SO_nR_1$ wherein n=0, 1, 2 or 3, $R_1$ is H, $C_1$-$C_6$ alkyl or aryl; and wherein Z is selected from the group consisting of methyl, aryl, a substituted aryl wherein the aryl substituents are selected from the group consisting of $C_1$-$C_6$ alkyl, nitro and halo, a polycyclic aromatic alkyl containing 2 aromatic rings and $C_1$-$C_6$ alkyl, a $C_2$-$C_6$ alkenyl, $C_6$ alkynyl, halomethyl, a $C_4$-$C_6$ haloalkyl, a $C_1$-$C_2$ hydroxyalkyl, a $C_1$-$C_6$ halohydroxy alkyl, acyloxy, an acyloxyalkyl wherein alkyl is $C_1$-$C_2$, carboxy, the acid and salt forms of carboxyalkyl wherein the alkyl is $C_1$-$C_6$, a $C_1$-$C_8$ alkoxy carbonyl, carbamoyl, a carbamoylalkyl wherein the alkyl is $C_1$-$C_6$, hydrazinocarbonyl, chlorocarbonyl, cyano, $C_2$-$C_9$ cyanoalkyl, C-formyl, a dialkoxymethyl wherein the alkoxy is $C_1$-$C_6$, C-acyl, an alkoxy hydroxyalkyl wherein alkyl and alkoxy are $C_1$-$C_4$, a carboxymethyl thio, carboalkoxy alkyl wherein the alkoxy and alkyl are $C_1$-$C_6$, a monoalkylamino hydroxylalkyl wherein the alkyl is $C_1$-$C_6$, a dialkylamino hydroxyalkyl wherein the alkyl is $C_1$-$C_6$, an amino hydroxyalkyl wherein the alkyl is $C_1$-$C_6$, a monosaccharide selected from the group consisting of aldotetrose, aldopentose and aldohexose, a polysaccharide selected from the group consisting of sucrose, lactose, maltose and cellobiose, a nucleic acid segment selected from the group consisting of 5'-d(AACAGCCATATG*GCCC)-3', 5'-d(GTGGGCGCTG*GAGGCG)-3', 5'-d(GTGGGCGCTGG*GAGGCG)-3', and 5'-d (GTGGGCGCTGG*AGGCG)-3' wherein G* is $O^6$-benzyl-2'-deoxyguanosine residue, and a steroid selected from the group consisting of testosterone, nortestosterone, and dihydrotestosterone, and $SO_nR_1$ wherein n is 0, 1, 2, or 3 and $R_1$ is H, $C_1$-$C_6$ alkyl or aryl.

56. A pharmaceutical composition comprising a compound of claim 55, and a pharmaceutically acceptable excipient.

57. The pharmaceutical composition of claim 56 which comprises an anti-neoplastic alkylating agent.

58. A method for treating tumor cells in a host which comprises administering to the host an amount effective to reduce AGT activity in the host of a compound of claim 55.

59. A method of enhancing the chemotherapeutic treatment of tumor cells in a host comprising, administering to the host chemotherapeutic treatment amount of an $O^6$-substituted guanine compound of claim and an anti-neoplastic alkylating agent whose mechanism of action involves modification of the $O^6$ position of DNA-guanine residue.

60. The method of claim 59 wherein said tumor is selected from the group consisting of colon tumor, brain tumor, prostate tumor, pancreatic tumor and skin tumor.

61. The method of claim 59 wherein said anti-neoplastic alkylating agent is selected from the group consisting of 1,3-bis(2-chloroethyl)-1-nitrosourea, 1-(2-chloroethyl)-3-cyclohexyl-1-nitrosourea, 1-(2-chloroethyl)-3-(4-methylcyclohexyl)-1-nitrosourea, 1-(2-chloroethyl)-3-(4-amino-2-methyl-5-pyrimidinyl)methyl-1-nitrosourea, 1-(2-chloroethyl)-3-(2-hydroxyethyl)-1-nitrosourea, 2-chloroethylmethylsulfonylmethanesulfonate, 1-[N-(2-chloroethyl)-N-nitrosoureido]ethylphosphonic acid diethyl ester, 2-deoxy-2-(3-methyl-3-nitrosoureido)-D-glucopyranose, N-(1-methylethyl)-4-[(2-methylhydrazino) methyl]benzamide, 8-carbamoyl-3-methylimidazo [5,1-d]-1,2,3,5-tetrazin-4-(3H)-one and 5-(3, 3-dimethyl-1-triazenyl)-1H-imidazole-4-carboxamide.

62. The method of claim 35 wherein said tumor is selected from the group consisting of colon tumor, brain tumor, prostate tumor, pancreatic tumor and skin tumor.

63. The method of claim 35 wherein said anti-neoplastic alkylating agent is selected from the group consisting of 1,3-bis(2-chloroethyl)-1-nitrosourea, 1-(2-chloroethyl)-3-cyclohexyl-1-nitrosourea, 1-(2-chloroethyl)-3-(4-methylcyclohexyl)-1-nitrosourea, 1-(2-chloroethyl)-3-(4-amino-2-methyl-5-pyrimidinyl) methyl-1-nitrosourea, 1-(2-chloroethyl)-3-(2-hydroxyethyl)-1-nitrosourea, 2-chloroethylmethylsulfonylmethanesulfonate, 1-[N-(2-chloroethyl)-N-nitrosoureido]ethylphosphonic acid diethyl ester, 2-deoxy-2-(3-methyl-3-nitrosoureido)-D-glucopyranose, N-(1-methylethyl)-4-[(2-methylhydrazino) methyl]benzamide, 8-carbamoyl-3-methylimidazo [5,1-d]-1,2,3,5-tetrazin-4-(3H)-one and 5-(3, 3-dimethyl-1-triazenyl)-1H-imidazole-4-carboxamide.

64. The method of claim 35 wherein said anti-neoplastic alkylating agent is selected from the group consisting of 1,3-bis(2-chloroethyl)-1-nitrosourea, 1-(2-chloroethyl)-3-cyclohexyl-1-nitrosourea, and 2-chloroethylmethylsulfonylmethanesulfonate.

65. The method of claim 36 wherein said tumor is selected from the group consisting of colon tumor, brain tumor, prostate tumor, pancreatic tumor and skin tumor.

66. The method of claim 39 wherein said anti-neoplastic alkylating agent is selected from the group consisting of 1,3-bis(2-chloroethyl)-1-nitrosourea, 1-(2-chloroethyl)-3-cyclohexyl-1-nitrosourea, 1-(2-chloroethyl)-3-(4-methylcyclohexyl)-1-nitrosourea, 1-(2-chloroethyl)-3-(4-amino-2-methyl-5-pyrimidinyl)methyl-1-nitrosourea, 1-(2-chloroethyl)-3-(2-hydroxyethyl)-1-nitrosourea, 2-chloroethylmethylsulfonylmethanesulfonate, 1-[N-(2-chloroethyl)-N-nitrosoureido]ethylphosphonic acid diethyl ester, 2-deoxy-2-(3-methyl-3-nitrosoureido)-D-glucopyranose, N-(1-methylethyl)-4-[(2-methylhydrazino) methyl]benzamide, 8-carbamoyl-3-methylimidazo [5,1-d]-1,2,3,5-tetrazin-4-(3H)-one and 5-(3, 3-dimethyl-1-triazenyl)-1H-imidazole-4-carboxamide.

67. A method for treating tumor cells in a host which comprises administering to the host an amount effective to reduce AGT activity in the host of a compound of claim 5.

68. A compound of the formula:

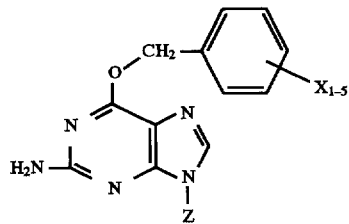

wherein each of $X_1$–$X_5$ is selected from the group consisting of hydroxy, aryl, a $C_1$–$C_8$ alkyl substituted aryl, a polycyclic aromatic alkyl containing 2–4 aromatic rings wherein the alkyl is a $C_1$–$C_6$, a $C_3$–$C_8$ cycloalkyl, a $C_2$–$C_6$ alkenyl, a $C_2$–$C_6$ alkynyl, a $C_1$–$C_6$ hydroxyalkyl, a $C_1$–$C_8$ alkoxy, a $C_2$–$C_8$ alkoxyalkyl, aryloxy, acyloxy, an acyloxyalkyl wherein the alkyl is $C_1$–$C_6$, amino, a monoalkylamino wherein the alkyl is $C_1$–$C_6$, a dialkylamino wherein the alkyl is $C_1$–$C_6$, acylamino, ureido, thioureido, carboxy, a carboxyalkyl wherein the alkyl is $C_1$–$C_6$, cyano, a cyanoalkyl wherein the alkyl is $C_1$–$C_6$, C-formyl, C-acyl, a dialkoxymethyl wherein the alkoxy is $C_1$–$C_6$, an aminoalkyl wherein the alkyl is $C_1$–$C_6$, and $SO_nR_1$ wherein n=0, 1, 2 or 3, $R_1$ is H, a $C_1$–$C_6$ alkyl or aryl; and wherein Z is selected from the group consisting of methyl, aryl, a substituted aryl wherein the aryl substituents are selected from the group consisting of $C_1$–$C_6$ alkyls, nitro and halo, a polycyclic aromatic alkyl containing 2–4 aromatic rings, $C_1$–$C_6$ alkyl, $C_2$–$C_6$ alkenyl, $C_6$ alkynyl, halomethyl, $C_3$–$C_6$ haloalkyl, $C_1$–$C_3$ hydroxyalkyl, $C_1$–$C_6$ halohydroxy alkyl, acyloxy, an acyloxyalkyl wherein the alkyl is $C_1$–$C_3$, carboxy, the acid and salt forms of carboxyalkyl wherein the alkyl is $C_1$–$C_6$, $C_1$–$C_8$ alkoxy, carbonyl, carbamoyl, a carbamoylalkyl wherein the alkyl is $C_1$–$C_6$, hydrazinocarbonyl, chlorocarbonyl, cyano, $C_2$–$C_9$ cyanoalkyl, C-formyl, a dialkoxymethyl wherein the alkoxy is $C_1$–$C_6$, C-acyl, an alkoxy hydroxyalkyl wherein the alkyl and the alkoxy are $C_1$–$C_4$, carboxymethyl thio, a carboalkoxy alkyl wherein the alkoxy and alkyl are $C_1$–$C_6$, a monoalkylamino hydroxyalkyl wherein the alkyl is $C_1$–$C_6$, a dialkylamino hydroxyalkyl wherein the alkyl is $C_1$–$C_6$, amino hydroxyalkyl wherein the alkyl is $C_1$–$C_6$, a peptide, a monosaccharide selected from the group consisting of aldotetroses, aldopentoses, and aldohexoses, a polysaccharide selected from the group consisting of sucrose, lactose, maltose and cellobiose, a nucleic acid segment, asteroid selected from the group consisting of testosterone, nortestosterone, and dihydrotestosterone, and $SO_nR_1$ wherein n is 0, 1, 2, or 3 and $R_1$ is H, $C_1$–$C_6$ alkyl or aryl.

69. A pharmaceutical composition comprising a compound of claim 24 and a pharmaceutically acceptable excipient.

70. A pharmaceutical composition comprising a compound of claim 25 and a pharmaceutically acceptable excipient.

71. A pharmaceutical composition comprising a compound of claim 26 and a pharmaceutically acceptable excipient.

72. A pharmaceutical composition comprising a compound of claim 68 and a pharmaceutically acceptable excipient.

73. A method for treating tumor cells in a host which comprises administering to the host an amount effective to reduce AGT activity in the host of a compound of claim 24.

74. A method for treating tumor cells in a host which comprises administering to the host an amount effective to reduce AGT activity in the host of a compound of claim 25.

75. A method for treating tumor cells in a host which comprises administering to the host an amount effective to reduce AGT activity in the host of a compound of claim 26.

76. A method for treating tumor cells in a host which comprises administering to the host an amount effective to reduce AGT activity in the host of a compound of claim 68.

* * * * *

UNITED STATES PATENT AND TRADEMARK OFFICE
CERTIFICATE OF CORRECTION

| | | |
|---|---|---|
| PATENT NO. | : 5,691,307 | Page 1 of 1 |
| APPLICATION NO. | : 08/255190 | |
| DATED | : November 25, 1997 | |
| INVENTOR(S) | : Moschel et al. | |

It is certified that error appears in the above-identified patent and that said Letters Patent is hereby corrected as shown below:

IN THE TITLE PAGE:

Item (73) Assignees: "The United States of America as represented by the Department of Health and Human Services, Washington, DC (US)" should read --Government of the United States of America, represented by the Secretary, Department of Health and Human Services, Rockville, MD (US)--.

At column 1, line 18 immediately before "FIELD OF INVENTION," please add the following statement:

--STATEMENT REGARDING
FEDERALLY SPONSORED RESEARCH AND DEVELOPMENT

This invention was also made with Government support under Grant Number CA18137 and CA47728 awarded by the National Cancer Institute of the National Institutes of Health. The Government may have certain rights in this invention.--

Signed and Sealed this

Fifth Day of June, 2007

JON W. DUDAS
*Director of the United States Patent and Trademark Office*